(12) United States Patent
Kayyem et al.

(10) Patent No.: US 7,381,525 B1
(45) Date of Patent: *Jun. 3, 2008

(54) AC/DC VOLTAGE APPARATUS FOR DETECTION OF NUCLEIC ACIDS

(75) Inventors: Jon Faiz Kayyem, Pasadena, CA (US); Stephen D. O'Connor, Pasadena, CA (US)

(73) Assignee: Clinical Micro Sensors, Inc., Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/873,597

(22) Filed: Jun. 12, 1997

Related U.S. Application Data

(60) Provisional application No. 60/040,155, filed on Mar. 7, 1997.

(51) Int. Cl.
- C12Q 1/68 (2006.01)
- C12M 1/36 (2006.01)
- C07H 21/04 (2006.01)
- G01N 15/06 (2006.01)

(52) U.S. Cl. ............... 435/6; 435/283.1; 435/287.2; 536/23.1; 422/68.1

(58) Field of Classification Search ............ 435/6, 435/174; 422/50, 68.1; 536/22.1, 23.1, 24.1, 536/24.3, 24.33, 25.3; 436/501; 438/283.1
See application file for complete search history.

(56) References Cited

U.S. PATENT DOCUMENTS

| | | | |
|---|---|---|---|
| 4,704,193 A | 11/1987 | Bowers et al. | |
| 4,707,352 A | 11/1987 | Stavrianopoulos | |
| 4,707,440 A | 11/1987 | Stavrianopoulos | ............. 435/6 |
| 4,711,955 A | 12/1987 | Ward et al. | |
| 4,755,458 A | 7/1988 | Rabbani et al. | |
| 4,787,963 A | 11/1988 | Mac Connell | |
| 4,840,893 A | 6/1989 | Hill et al. | ................. 435/6 |
| 4,849,513 A | 7/1989 | Smith et al. | ................. 536/27 |
| 4,868,103 A | 9/1989 | Stavrianopoulos et al. | |
| 4,894,325 A | 1/1990 | Englehardt et al. | |
| 4,943,523 A | 7/1990 | Stavrianopoulos | |
| 4,945,045 A | 7/1990 | Forrest et al. | |
| 4,952,685 A | 8/1990 | Stavrianopoulos | |
| 4,994,373 A | 2/1991 | Stavrianopoulos | |
| 5,002,885 A | 3/1991 | Stavrianopoulos | |
| 5,013,831 A | 5/1991 | Stavrianopoulos | |
| 5,082,830 A | 1/1992 | Brakel et al. | |
| 5,089,112 A | 2/1992 | Skotheim et al. | |
| 5,175,269 A | 12/1992 | Stavrianopoulos | |
| 5,180,968 A | 1/1993 | Bruckenstein et al. | |
| 5,241,060 A | 8/1993 | Engelhardt et al. | |
| 5,242,828 A | 9/1993 | Bergstrom et al. | |
| 5,278,043 A | 1/1994 | Bannwarth et al. | ......... 536/23.1 |
| 5,312,527 A | 5/1994 | Mikkelsen et al. | ..... 204/153.12 |
| 5,328,824 A | 7/1994 | Ward et al. | |
| 5,356,786 A | 10/1994 | Heller et al. | |
| 5,391,272 A | 2/1995 | O'Daly | |
| 5,403,451 A | 4/1995 | Riviello et al. | ............ 204/153.1 |
| 5,434,049 A * | 7/1995 | Okano et al. | ................... 435/6 |
| 5,436,161 A | 7/1995 | Bergstrom et al. | |
| 5,443,701 A | 8/1995 | Willner et al. | |
| 5,449,767 A | 9/1995 | Ward et al. | |
| 5,472,881 A | 12/1995 | Beebe et al. | .................. 436/94 |
| 5,476,928 A | 12/1995 | Ward et al. | |
| 5,552,270 A | 9/1996 | Khrapko et al. | |
| 5,565,552 A | 10/1996 | Magda et al. | ................. 534/11 |
| 5,571,568 A | 11/1996 | Ribi et al. | |
| 5,573,906 A | 11/1996 | Bannwarth et al. | ............. 435/6 |
| 5,591,578 A | 1/1997 | Meade et al. | ................... 435/6 |
| 5,595,908 A | 1/1997 | Fawcett et al. | ................ 534/11 |
| 5,601,982 A | 2/1997 | Sargent et al. | ................ 435/6 |
| 5,620,850 A | 4/1997 | Bamdad et al. | ............ 530/300 |
| 5,632,957 A | 5/1997 | Heller et al. | |
| 5,700,667 A | 12/1997 | Marble et al. | |
| 5,705,348 A | 1/1998 | Meade et al. | |
| 5,741,700 A | 4/1998 | Ershov et al. | |
| 5,756,050 A | 5/1998 | Ershov et al. | |
| 5,770,369 A | 6/1998 | Meade et al. | |
| 5,770,721 A | 6/1998 | Ershov et al. | |
| 5,776,672 A | 7/1998 | Hashimoto et al. | |
| 5,780,234 A | 7/1998 | Meade et al. | |
| 5,795,453 A | 8/1998 | Gilmartin | |
| 5,824,473 A | 10/1998 | Meade et al. | |
| 5,837,859 A | 11/1998 | Teoule et al. | |

(Continued)

FOREIGN PATENT DOCUMENTS

| | | |
|---|---|---|
| CA | 2 090904 | 9/1993 |
| EP | 0 63879 | 11/1982 |
| EP | 0 234938 | 2/1987 |
| EP | 0 229943 | 7/1987 |
| EP | 0 599337 | 1/1994 |
| EP | 0515615 | 9/1996 |

(Continued)

OTHER PUBLICATIONS

Alleman, K.S., et al., "Electrochemical Rectification at a Monolayer-Modified Electrode," *J. Phys. Chem.*, 100:17050-17058 (1996).

Arkin et al. "Evidence for Photoelectron Transfer Through DNA Intercalation," *J. Inorganic Biochem. Abstracts*, 6th International Conference on Bioinorganic Chemistry, 51(1) & (2):526 (1993).

Barisci, et al., "Conducting Polymer Sensors," *TRIP*, 4(9):307-311 (1996).

Baum, R. M., "Views on Biological; Long-Range Electron Transfer Stir Debate," *C&EN*, pp. 20-23 (1993).

(Continued)

*Primary Examiner*—B J Forman
(74) *Attorney, Agent, or Firm*—Morgan Lewis & Bockius LLP; Robin M. Silva

(57) ABSTRACT

The invention relates to nucleic acids covalently coupled to electrodes via conductive oligomers. More particularly, the invention is directed to the site-selective modification of nucleic acids with electron transfer moieties and electrodes to produce a new class of biomaterials, and to methods of making and using them.

15 Claims, 28 Drawing Sheets

U.S. PATENT DOCUMENTS

| | | | |
|---|---|---|---|
| 5,849,486 A * | 12/1998 | Heller et al. | 435/6 |
| 5,851,772 A | 12/1998 | Mirzabekov et al. | |
| 5,952,172 A | 9/1999 | Meade et al. | 435/6 |
| 5,976,802 A | 11/1999 | Ansorge et al. | |
| 6,060,327 A | 5/2000 | Keen | |
| 6,071,699 A | 6/2000 | Meade et al. | |
| 6,087,100 A | 7/2000 | Meade et al. | |
| 6,090,933 A | 7/2000 | Kayyem et al. | |
| 6,096,273 A * | 8/2000 | Kayyem et al. | 422/68.1 |
| 6,096,825 A | 8/2000 | Garnier | |
| 6,107,080 A | 8/2000 | Lennox | |
| 6,177,250 B1 | 1/2001 | Meade et al. | |
| 6,180,352 B1 | 1/2001 | Meade et al. | |
| 6,197,515 B1 | 3/2001 | Bamdad et al. | |
| 6,200,761 B1 | 3/2001 | Meade et al. | |
| 6,203,758 B1 | 3/2001 | Marks et al. | |
| 6,207,369 B1 | 3/2001 | Wohlstadter et al. | |
| 6,221,583 B1 | 4/2001 | Kayyem et al. | |
| 6,232,062 B1 | 5/2001 | Kayyem et al. | |
| 6,238,870 B1 | 5/2001 | Meade et al. | |
| 6,248,229 B1 * | 6/2001 | Meade | 205/777.5 |
| 6,258,545 B1 | 7/2001 | Meade et al. | |
| 6,265,155 B1 | 7/2001 | Meade et al. | |
| 6,268,149 B1 | 7/2001 | Meade et al. | |
| 6,268,150 B1 | 7/2001 | Meade et al. | |
| 6,277,576 B1 | 8/2001 | Meade et al. | |
| 6,290,839 B1 | 9/2001 | Kayyem et al. | |
| 6,291,188 B1 | 9/2001 | Meade et al. | |
| 6,306,584 B1 | 10/2001 | Bamdad | |
| 6,322,979 B1 | 11/2001 | Bamdad et al. | |
| 6,432,723 B1 | 8/2002 | Plaxco et al. | |
| 6,479,240 B1 | 11/2002 | Kayyem et al. | |
| 6,495,323 B1 | 12/2002 | Kayyem et al. | |
| 6,528,266 B2 | 3/2003 | Meade et al. | |
| 6,686,150 B1 | 2/2004 | Blackburn et al. | |
| 6,740,518 B1 | 5/2004 | Duong et al. | |
| 7,014,992 B1 * | 3/2006 | Kayyem et al. | 435/6 |
| 2001/0034033 A1 | 10/2001 | Meade et al. | |
| 2001/0046679 A1 | 11/2001 | Meade et al | |

FOREIGN PATENT DOCUMENTS

| | | |
|---|---|---|
| JP | 238166.0 | 10/1988 |
| JP | 6-41183 | 2/1994 |
| WO | WO86/05815 | 3/1985 |
| WO | 90/05732 | 5/1990 |
| WO | 9 210 757 | 6/1992 |
| WO | 9 310 267 | 5/1993 |
| WO | 93/22678 | 11/1993 |
| WO | 93/23425 | 11/1993 |
| WO | 9 515 971 | 6/1995 |
| WO | 9 640712 | 12/1996 |
| WO | 97/01646 | 1/1997 |
| WO | WO98/57159 | 6/1997 |
| WO | WO97/27329 | 7/1997 |
| WO | WO97/31256 | 8/1997 |
| WO | 97/44651 | 11/1997 |
| WO | WO97/41425 | 11/1997 |
| WO | WO97/46568 A1 | 12/1997 |
| WO | WO98/12539 A1 | 3/1998 |
| WO | WO98/20162 | 5/1998 |
| WO | WO98/27229 | 6/1998 |
| WO | WO98/28444 | 7/1998 |
| WO | WO98/31839 A2 | 7/1998 |
| WO | WO98/35232 | 8/1998 |
| WO | WO98/51823 | 11/1998 |
| WO | WO99/14596 | 3/1999 |
| WO | WO99/29711 | 6/1999 |
| WO | WO99/37819 A2 | 7/1999 |
| WO | WO99/57317 A1 | 11/1999 |
| WO | WO99/57319 | 11/1999 |
| WO | WO99/67425 | 12/1999 |

OTHER PUBLICATIONS

Bechtold, R., et al., "Ruthenium-Modified Horse Heart Cytochrome c: Effect of pH and Ligation on the Rate of Intramolecular Electron Transfer between Ruthenium(II) and Heme(III)," *J. Phys. Chem.*, 90(16):3800-3804 (1986).

Bidan, "Electroconducting conjugated polymers: new sensitive matrices to build up chemical or electrochemical sensors. A Review.," *Sensors and Actuators*, B6:45-56 (1992).

Biotechnology and Genetics: Genetic Screening Integrated Circuit, *The Economist* (Feb. 25-Mar. 3, 1995).

Boguslavsky, L. et al., "Applications of redox polymers in biosensors," *Solid State Ionics*, 60:189-197 (1993).

Bowler, B. E., et al., "Long-Range Electron Transfer in Donor (Spacer) Acceptor Molecules and Proteins," *Progress in Inorganic Chemistry: Bioinorganic Chemistry*, 38:259-322 (1990).

Brun, A. M., et al., "Photochemistry of Intercalated Quaternary Diazaaromatic Salts," *J. Am. Chem. Soc.*, 113:8153-8159 (1991).

Bumm, et al., "Are single Molecular Wires Conducting?," *Science* 271:1705-1707 (1996).

Cantor, C.R. et al., "Report on the Sequencing by Hybridization Workshop," *Genomics*, 13:1378-1383 (1992).

Chang, I-Jy, et al., "High-Driving-Force Electron Transfer in Metalloproteins: Intramolecular Oxidation of Ferrocytochrome c by Ru(2,2'-bpy)$_2$(im) (His-33)$^{3+}$," *J. Am. Chem. Soc.*, 113:7056-7057 (1991).

Chidsey, C.E.D., et al., "Free Energy and Temperature Dependence of Electron Transfer at the Metal Electrolyte Interface," *Science*, 251:919-923 (1991).

Chidsey, et al., "Coadsorption of Ferrocene-Terminated and Unsubstituted Alkanethiols on Gold" Electroactive Self-Assembled Monolayers, *J. Am. Chem. Soc.*, 112:4301-4306 (1990).

Chrisey, et al., "Covalent attachment of synthetic DNA to self-assembled monolayer films," *Nucleic Acids Research*, 24(15):3031-3039 (1996).

Clery, "DNA Goes Electric," *Science*, 267:1270 (1995).

*Commerce Business Daily* Issue of Sep. 26, 1996 PSA#1688.

Database WPI, Derwent Publications Ltd., London, GB; AN 88-320199 & JP, A, 53 238 166 (Mitsubishi Denki KK), Oct. 4, 1988.

Davis, L. M., et al., "Electron Donor Properties of the Antitumour Drug Amsacrine as Studied by Fluorescence Quenching of DNA-Bound Ethidium," *Chem.-Biol. Interactions*, 62:45-58 (1987).

Davis, L. M., et al., "Elements of biosensor construction," *Enzyme Microb. Technol.* 17:1030-1035 (1995).

Degani et al., "Direct Electrical Communication between Chemically Modified Enzymes and Metal Electrodes. 2. Methods for Bonding Electron-Transfer Relays to Glucose Oxidase and D-Amino-Acid Oxidase," *J. Am. Chem. Soc.* 110:2615-2620 (1988).

Degani, Y., et al., "Electrical Communication between Redox Centers of Glucose Oxidase and Electrodes via Electrostatically and Covalently Bound Redox Polymers," *J. Am. Chem. Soc.*, 111:2357-2358 (1989).

Degani, Y., et al., "Direct Electrical Communication between Chemically Modified Enzymes and Metal Electrodes. 1. Electron Transfer from Glucose Oxidase to Metal Electrodes via Electron Relays, Bound Covalently to the Enzyme," *J. Phys. Chem.*, 91(6):1285-1288 (1987).

Deinhammer, R.S., et al., "Electronchemical Oxidation of Amine-containing compounds: A Route to the Surface Modification of glassy carbon electrodes" *Langmuir*, 10:1306-1313 (1994).

Dreyer, G. B., et al., "Sequence-specific cleavage of single-stranded DNA: Oligodeoxynucleotide-EDTA-Fe(II)," *Proc. Natl. Acad. Sci. USA*, 82:968-972 (1985).

Durham, B., et al., "Photoinduced Electron-Transfer Kinetics of Singly Labeled Ruthenium Bis(bipyridin) Dicarboxybipyridine Cytochrome c Derivatives," *Biochemistry*, 28:8659-8665 (1989).

Durham, B., et al., "Electron-Transfer Kinetics of Singly Labeled Ruthenium(II) Polypyridine Cytochrome c Derivatives," *American Chemical Society*, pp. 181-193 (1990).

Elias, H., et al., "Electron-Transfer Kinetics of Zn-Substituted Cytochrome c and Its Ru(NH₃)₅(Histidine-33) Derivative," *J. Am. Chem. Soc.*, 110:429-434 (1988).

Farver, O., et al., "Long-range intramolecular electron transfer in azurins," *Proc. Natl. Acad. Sci. USA*, 86:6968-6972 (1989).

Fox, L. S., et al., "Gaussian Free-Energy Dependence of Electron-Transfer Rates in Iridium Complexes," *Science*, 247:1069-1071 (1990).

Fox, M. A., et al., "Light-Harvesting Polymer Systems," *C&EN*, pp. 38-48 (Mar. 15, 1993).

Francois, J-C., et al., "Periodic Cleavage of Poly(dA) by Oligothymidylates Covalently Linked to the 1,10-Phenanthroline-Copper Complex," *Biochemistry*, 27:2272-2276 (1988).

Friedman, A. E., et al., "Molecular 'Light Switch' for DNA: Ru(bpy)₂(dppz)²⁺, " *J. Am. Chem. Soc.*, 112:4960-4962 (1990).

Fromherz, P., et al., "Photoinduced Electron Transfer in DNA Matrix from Intercalated Ethidium to Condensed Methylviologen," *J. Am. Chem. Soc.*, 108:5361-5362 (1986).

Gardner, et al., "Application of conducting polymer technology in microsystems," *Sensors and Actuators*, A51:57-66 (1995).

Gregg, B. A., et al., "Cross-linked redox gels containing glucose oxidase for amperometric biosensor applications," *Anal. Chem.*, 62:258-263 (1990).

Gregg, B. A., et al., "Redox Polymer Films Containing Enzymes. 1. A Redox-Conducting Epoxy Cement: Synthesis, Characterization, and Electrocatalytic Oxidation of Hydroquinone," *J. Phys. Chem.*, 95:5970-5975 (1991).

Hashimoto, et al., "Sequence-Specific Gene Detection with a Gold Electrode Modified with DNA Probes and an Electrochemically Active Dye," *Anal. Chem.* 66:3830-3833 (1994).

Hegner, et al., "Immobilizing DNA on gold via thiol modification for atomic force microscopy imaging in buffer solutions," *FEBS* 336(3):452-456 (1993).

Heller, A., et al., "Amperometric biosensors based on three-dimensional hydrogel-forming epoxy networks," *Sensors and Actuators*, 13-14:180-183 (1993).

Heller, A., "Electrical Wiring of Redox Enzymes," *Acc. Chem. Res.*, 23:128-134 (1990).

Heller et al., "Fluorescent Energy Transfer Oligonucleotide Probes," *Fed. Proc.* 46(6):1968 (1987) Abstract No. 248.

Ho "DNA-Mediated Electron Transfer and Application to 'Biochip'Development," *Abstract. Office of Naval Research* (Report Date: Jul. 25, 1991) 1-4, RR04106.

Hobbs et al., "Polynucleotides Containing 2'-Amino-2'deoxyribose and 2'-Azido-2'-deoxyriose," *Biochemistry*, 12(25):5138-5145 (1973).

Hsung, et al., "Synthesis and Characterization of Unsymmetric Ferrocene-Terminated Phenylethynyl Oligomers," *Organometallics*, 14:4808-4815 (1995).

Hsung, et al., "Thiophenol Protecting Groups for the Palladium-Catalyzed Heck Reaction: Efficient Syntheses of Conjugated Arylthiols," *Tetrahedron Letters*. 36(26):4525-4528 (1995).

Jenkins et al., A Sequence-Specific Molecular Light Switch: Tebhering of an Oligonucleotide to a Dipyridophenazine Complex of Ruthenium (II), *J. Am. Chem. Soc.*, 114:8736-8738 (1992).

Katritzky, et al., "Pyridyethylation—A New Protection Method for Active Hydrogen Compounds," *Tetrahedron Letters*,25(12):1223-1226 (1984).

Kelley, S.O. and J.K. Barton, "Electrochemistry of Methylene Blue Bound to a DNA-Modified Electrode," *Bioconjugate Chem.*, 8:31-37 (1997).

Kojima et al., "A DNA Probe of Ruthenium Bipyridine Complex Using Photocatalytic Activity," *Chemistry Letter*, pp. 1889-1982 (1989).

Laviron, E., "A.C. Polarography and Faradaic Impedance of Strongly Adsorbed Electroactive Species. Part I: Theoretical and Experimental Study of a Quasi-Reversible Reaction in the Case of a Langmuir Isotherm," *J. Electroanal. Chem.*, 97:135-149 (1979).

Laviron, E., "A.C. Polarography and Faradaic Impedance of Strongly Adsorbed Electroactive Species. Part III: Theoretical Complex Plane Analysis for a Surface Redox Reaction," *J. Electroanal. Chem.*, 105:35-42 (1979).

Lee, et al., "Direct Measurement of the Forces Between Complementary Strands of DNA," *Science*, 266:771-773 (1994).

Lenhard, J.R., et al., "Part VII Covalent Bonding of a Reversible-Electrode Reactanbt to Pt Electrodes Using an organosilane Reagent" *J. Electronal. Chem.*, 78:195-201 (1977).

Lipkin "Identifying DNA by the Speed of Electrons," *Science News*, 147(8):117 ( 1995).

Maskos, et al., "Oligonucleotide hybridisations on glass supports: a novel linker for oligonucleotide synthesis and hybridisation properties of oligonucleotides synthesised in situ," *Nucleic Acids Research*, 20(7):1679-1684 (1992).

Mazzocchi, Ph.H. and G. Fritz, "Photolysis of N-(2-Methyl-2-Propenyl)phthalimide in Methanol. Evidence Supporting Radical-Radical Coupling of a Photochemically Generated Radical Ion Pair," *Journal of the American Chemical Society*, 108(18):5361-5362 (1986).

McGee et al., "2'-Amino-2'-deoxyuridine via an Intramolecular Cyclization of a Trichloroacetimidate," *J. Org. Chem.*, 61:781-785 (1996).

Meade, T. J., "Driving-Force Effects on the Rate of Long-Range Electron Transfer in Ruthenium-Modified Cytochrome c," *J. Am. Chem. Soc.*, 111:4353-4356 (1989).

Meade, T. J., et al., "Electron Transfer through DNA: Site-Specific Modification of Duplex DNA with Ruthenium Donors and Acceptors," *Angew Chem. Int. Ed. Engl.*, 34:352 (1995).

Mestel, "'Electron Highway' Points to Identity of DNA," *New Scientist*, p. 21 (1995).

Millan, et al., "Voltammetric DNA Biosensor for Cystic Fibrosis Based on a Modified Carbon Paste Electrode," *Anal. Chem.*, 66:2943-2948 (1994).

Millan, K.M., et al., "Covalent Immobilization of DNA onto Glassy Carbon Electrodes," *Electroanalysis*, 4:929-932 (1992).

Millan, K.M. and Mikkelsen, S.R., "Sequence-Selective Biosensor for DNA Based on Electroactive Hybridization Indicators," *Anal. Chem.*, 65:2317-2323 (1993).

Miller, C., "Absorbed ω-Hydroxy Thiol Monolayers on Gold Electrodes: Evidence for Electron Tunneling to Redox Species in Solution," *J. Phys. Chem.*, 95:877-886 (1991).

Murphy, C. J., et al., "Long-Range Photoinduced Electron Transfer Through a DNA Helix," *Science*, 262:1025-1029 (1993).

Orellana, G., et al., "Photoinduced Electron Transfer Quenching of Excited Ru(II) Polypyridyls Bound to DNA: The Role of the Nucleic Acid Double Helix," *Photochemistry and Photobiology*, 54(4):499-509 (1991).

Palecek, "From Polarography of DNA to Microanalysis with Nucleic Acid-Modified Electrodes," *Electroanalysis*, 8(1):7-14 (1996).

Paterson, "Electric Genes: Current Flow in DNA Could Lead to Faster Genetic Testing," *Scientific American*, 33-34 (May 1995).

Purugganan, M. D., et al., Accelerated Electron Transfer Between Metal Complexes Mediated by DNA, *Science*, 241:1645-1649 (1988).

Rhodes, D. And A. Klug, "Helical Periodicity of DNA Determined by Enzyme Digestion," *Nature*, 286:573-578 (1980).

Risser, S. M., et al., "Electron Transfer in DNA: Predictions of Exponential Growth and Decay of Coupling with Donor-Acceptor Distance," *J. Am. Chem. Soc.*, 115(6):2508-2510 (1993).

Sato, Y., et al., "Unidirectional Electron Transfer at Self-Assembled Monolayers of 11-Ferrocenyl-1-undecanethiol on Gold," *Bull. Chem. Soc. Jpn.*, 66(4):1032-1037 (1993).

Satyanarayana, S., et al., "Neither Δ- nor Λ-Tris(phenanthroline)ruthenium(II) Binds to DNA by Classical Intercalation," *Biochemistry*, 31(39):9319-9324 (1992).

Schreiber, et al., "Bis(purine) Complexes of *trans*-$a_2Pt^{II}$: Preparation and X-ray Structures of Bis(9-methyladenine) and Mixed 9-Methyladenine, 9-Methylguanine Complexes and Chemistry Relevant to Metal-Modified Nucelobase Triples and Quartets," *J. Am. Chem. Soc.* 118:4124-4132 (1996).

Schuhmann, W., et al., "Electron Transfer between Glucose Oxidase and Electrodes via Redox Mediators Bound with Flexible Chains to the Enzyme Surface," *J. Am. Chem. Soc.*, 113:1394-1397 (1991).

Schumm, et al., "Iterative Divergent/Convergent Approach to Linear Conjugated Oligomers by Successive Doubling of the Molecular Length: A Rapid Route to a 128 Å-Long Potential Molecular Wire," *Angew. Chem. Int. Ed. Engl.*, 33(11):1360-1363 (1994).

Sigal et al., "A Self-Assembled Monolayer for the Binding and Study of Histidine-Tagged Proteins by Surface Plasmon Resonance," *Anal. Chem.*, 68(3):490-497 (1996).

Southern, et al., "Arrays of complementary oligonucleotides for analysing the hybridisation behaviour of nucleic acids," *Nucleic Acids Research*, 22(8):1368-1373 (1994).

Strobel, S. A., et al., "Site-Specific Cleavage of a Yeast Chromosome by Oligonucleotide-Directed Triple-Helix Formation," *Science*, 249:73-75 (1990).

Su, et al., "Interfacial Nucleic Acid Hybridization Studied by Random Primer $^{32}P$ Labelling and Liquid-Phase Acoustic Network Analysis," *Analytical Chemistry*, 66(6):769-777 (1994).

Telser, J., et al., "DNA Duplexes Covalently Labeled at Two Sites: Synthesis and Characterization by Steady-State and Time-Resolved Optical Spectroscopies," *J. Am. Chem. Soc.*, 111:7226-7232 (1989).

Telser, J., et al., "DNA Oligomers and Duplexes Containing a Covalently Attached Derivative of Tris(2,2'-bipyridine)ruthenium(II): Synthesis and Characterization by Thermodynamic and Optical Spectroscopic Measurements," *J. Am. Chem. Soc.*, 111:7221-7226 (1989).

Tour, "Conjugated Macromolecules of Precise Length and Constitution. Organic Synthesis for the Construction of Nanoarchitectures," *Chem. Rev.*, 96:537-553 (1996).

Tour, et al., "Self-Assembled Monolayers and Multilayers of Conjugated Thiols, α-107 -Dithiols, and Thioacetyl-Containing Adsorbates. Understanding Attachments between Potential Molecular Wires and Gold Surfaces," *J. Am. Chem. Soc.*, 117:9529-9534 (1995).

Tullius, T.D. and B.A. Dombroski, "Iron(II) EDTA Used to Measure the Helical Twist Along Any DNA Molecule," *Science*, 230:679-681 (1985).

Turro, N., et al. "Photoelectron Transfer Between Molecules Adsorbed in Restricted Spaces," *Photochem. Convers. Storage Sol. Energy, Proc. Int. Conf.*, 8th, pp. 121-139 (1990).

Turro, N. J., et al., "Molecular Recognition and Chemistry in Restricted Reaction Spaces. Photophysics and Photoinduced Electron Transfer on the Surfaces of Micelles, Dendrimers, and DNA," *Acc. Chem. Res.*, 24:332-340 (1991).

Uosake, K., et al., "A Self-Assembled Monolayer of Ferrocenylalkane Thiols on Gold as an Electron Mediator for the Reduction of Fe(III)-EDTA in Solution," *Electrochemica Acta.*, 36(11/12):1799-1801 (1991).

Van Ness, J., et al., "A Versatile Solid Support System for Oligodeoxynucleotide Probe-Based Hybridization Assays," *Nucleic Acids Research*, 19(12):3345-3349 (1991).

Weber, et al., "Voltammetry of Redox-Active Groups Irreversibly Adsorbed onto Electrodes. Treatment Using the Marcus Relation between Rate and Overpotential," *Anal. Chem.*, 66:3164-3172 (1994).

Williams, et al., "Studies of oligonucleotide interactions by hybridisation to arrays: the influence of dangling ends on duplex yield," *Nucleic Acids Research*, 22(8):1365-1367 (1994).

Winkler, J. R., et al., "Electron Transfer in Ruthenium-Modified Proteins," *Chem. Rev.*, 92:369-379 (1992).

Xu, et al., "Immobilization of DNA on an Aluminum(III) alkaneobisphosphonate Thin Film with Electrogenerated Chemiluminescent Detection," *J. Am. Chem. Soc.*, 116:8386-8387 (1994).

Xu, et al., "Immobilization and Hybridization of DNA on an Aluminum(III) Alkanebisphosphonate Thin Film with Electrogenerated Chemiluminescent Detection," *J. Am. Chem. Soc.*, 117:2627-2631 (1995).

Yang, et al., "Growth and Characterization of Metal(II) Alkaneobisphosphonate Multilayer Thin Films on Gold Surfaces," *J. Am. Chem. Soc.*, 115:11855-11862 (1993).

Zhou, et al., "Fluorescent Chemosensors Based on Energy Migration in Conjugated Polymers: The Molecular Wire Approach to Increased Sensitivity," *J. Am. Chem. Soc.*, 117:12593-12602 (1995).

Mucic et al., "Synthesis and Characterization of DNA with Ferrocenyl Groups Attached to their 5'-Termini: Electrochemical Characterization of a Redox-Active Nucleotide Monolayer," *Chem. Commun.*, pp. 555-557 (1996).

Carr et al., "Novel Electrochemical Sensors for Neutral Molecules," *Chem. Commun.*, 1649-1650 (1997).

Carter et al., "Voltammetric Studies of the Interaction of Metal Chelates with DNA. 2. Tris-Chelated Complexes of Cobalt(III) and Iron(II) with 10-Phenanthroline and 2,2'-Bipyridine," *J. Am. Chem. Soc.*, 11:8901-8911 (1989).

Johnston et al., "Trans-Dioxorhenium(V)-Mediated Electrocatalytic Oxidation of DNA at Indium Tin-Oxide Electrodes: Voltammetric Detection of DNA Cleavage in Solution," *Inorg. Chem.*, 33:6388-6390 (1994).

Aizawa et al., "Integrated Molecular Systems for Biosensors," *Sensors and Actuators B*, B@$ (Nos. 1/3) Part 1:1-5 (Mar. 1995).

Albers et al., "Design of Novel Molecular Wires for Realizing Long-Distance Electron Transfer," *Biochemistry and Bioenergetics*, 42:25-33 (1997).

Drobyshev, A. et al., "Sequence Analysis by Hybridization with Oligonucleotide Microchip: Identification of β-thalassemia Mutations," *Gene*, 188:45-52 (1997).

Dubiley, S. et al., "Fractionation, phosphorylation and Ligation on Oligonucleotide Microchips to Enhance Sequencing by Hybridization," *Nucleic Acids Research*, 25(12):2259-2265 (1997).

Elghanian et al., "Selective Colorimetric Detection of Polynucleotides Based on the Distance-Dependent Optical Properties of Gold Nanoparticles," *Science*, 277:1078-1081 (1997).

Fotin, A. et al., "Parallel Thermodynamic Analysis of Duplexes on Oligodeoxyribonucleotide Microchips," *Nucleic Acids Research*, 216(6):1515-1521 (1998).

Guschin, D. et al., "Manual Manufacturing of Oligonucleotide, DNA, and Protein Microchips," *Analytical Biochemistry*, 250:203-211 (1997).

Guschin, D. et al., "Oligonucleotide Microchips as Genosensors for Determinative and Environmental Studies in Microbiology," 63(6):2397-2402 (1997).

Kamat et al., J. Phys. chem., 93(4):1405-1409 (1989).

Korri-Youssoufi et al., "Toward Bioelectronics: Specific DNA Recognition Based on an Oligonucleotide-Functionalized Polypyrrole," *J. Am. Chem. Soc.*, 119(3):7388-7389 (1997).

Lincoln et al., "Shorting Circuiting the Molecular Wire," *J. Am. Chem. Soc.*, 119(6)1454-1455 (1997).

Livshits, M. et al., "Theoretical Analysis of the Kinetics of DNA Hybridization with Gel-Immobilized Oligonucleotides," *Biophysical Journal*, 71:2795-2801 (1996).

Mirkin et al., "A DNA-based Method for Ratioally Assembling Nonoparticles into Macroscopic Materials," *Nature*, 382:607-609 (1996).

Mirzabekov, A. et al., "Dna Sequencing by Hybridization—a Megasequencing Method and a Diagnostic Tool," *Tibtech*, 12:27-32 (1994).

Mitchell et al., "Programmed Assembly of DNA Functionalized Quantum Dots," *J. Am. Chem. Soc.*, 121:8122-8123 (1999).

Parinov, S., DNA Sequencing by Hybridization to Microchip octa- and Decanucleotides Extended by Stacked Pentanucleotides, *Nucleic Acids Research*, 24(15):2998-3004 (1996).

Proudnikov, D. "Immobilization of DNA in Polyacrylamide Gel for the manufacture of DNA and DNA-Oligonucleotide Microchips," *Analytical Biochemistry*, 259:34-41 (1998).

Proudnikov, D. et al., "Chemical Methods of DNA and RNA Fluorescent Labeling," *Nucleic Acids Research*, 24(22):4535-4542 (1996).

Reimers et al., "Toward Efficient Molecular Wires and Switches: the Brooker Ions," *Biosystems*, 35:107-111 (1995).

Sloop et al., "Metalloorganic labels for DNA sequencing and mapping," *New J. Chem.*, 18: 317-326 (1994).

Storhoff et al., "One-Pot Colorimetric Differentiation of Polynucleotides with Single Base Imperfections Using Gold Nanoparticles Probes," *J. Am. Chem. Soc.*, 120:1959-1964 (1998).

Timofeev, E. et al., "Regioselective Immobilization of Short Oligonucleotides to Acrylic Copolymer Gel," *Nucleic Acids Research*, 24(16): 3142-3148 (1996).

Timofeev, E. et al., "Methidium Intercalator Inserted into Synthetic Oligonucleotides," *Tetrahedron Letters*, 37(47):8467-8470 (1996).

Velev et al., "In Situ Assembly of Colloidal Particles into Miniaturized Biosensors," The ACS Journal of Surfaces and Colloids, Langmuir, 15(11):3693-3698 (1999).

Watson et al., "Hybrid Nanoparticles with Block Copolymer Shell Structures," J. Am. Chem. Soc., 121:462-463 (1999).

Yershov, G. et al., "DNA Analysis and Diagnostics on Oligonucleotide Microchips," Proc. Natl. Acad. Sci. USA, 93:4913-4918 (1996).

Bain et al., "Formation of Monolayers by the Coadsorption of Thiols on Gold: Variation in the Length of the Alkyl Chain," J. Am. Chem. Soc. 111:7164-7175 (1989).

Bamdad, C. "A DNA self-assembled monolayer for the specific attachment of unmodified double—or single stranded DNA," Biophysical Journal, 75:1997-2003 (1988).

Beattie et al., "Genosensor Technology," Clinical Chemistry, 39(4): 719-722 (1993).

Hess et al., "Base Paiting Properties of Novel Transition Metal PNA Conjugates," Journal of Inorganic Biochemistry, 74: (199).

Ihara et al., "Gene sensor using ferrocenyl oligonucleotide," Chem. Commun., 1609-1610 (1997).

Yu et al. "Uridine-conjugated-ferrocene DNA oligonucleotides for electronic detection of nucleic acids," Abstracts of Papers. ACS Ntational Meeting, 217(1): 76 (1999).

\* cited by examiner

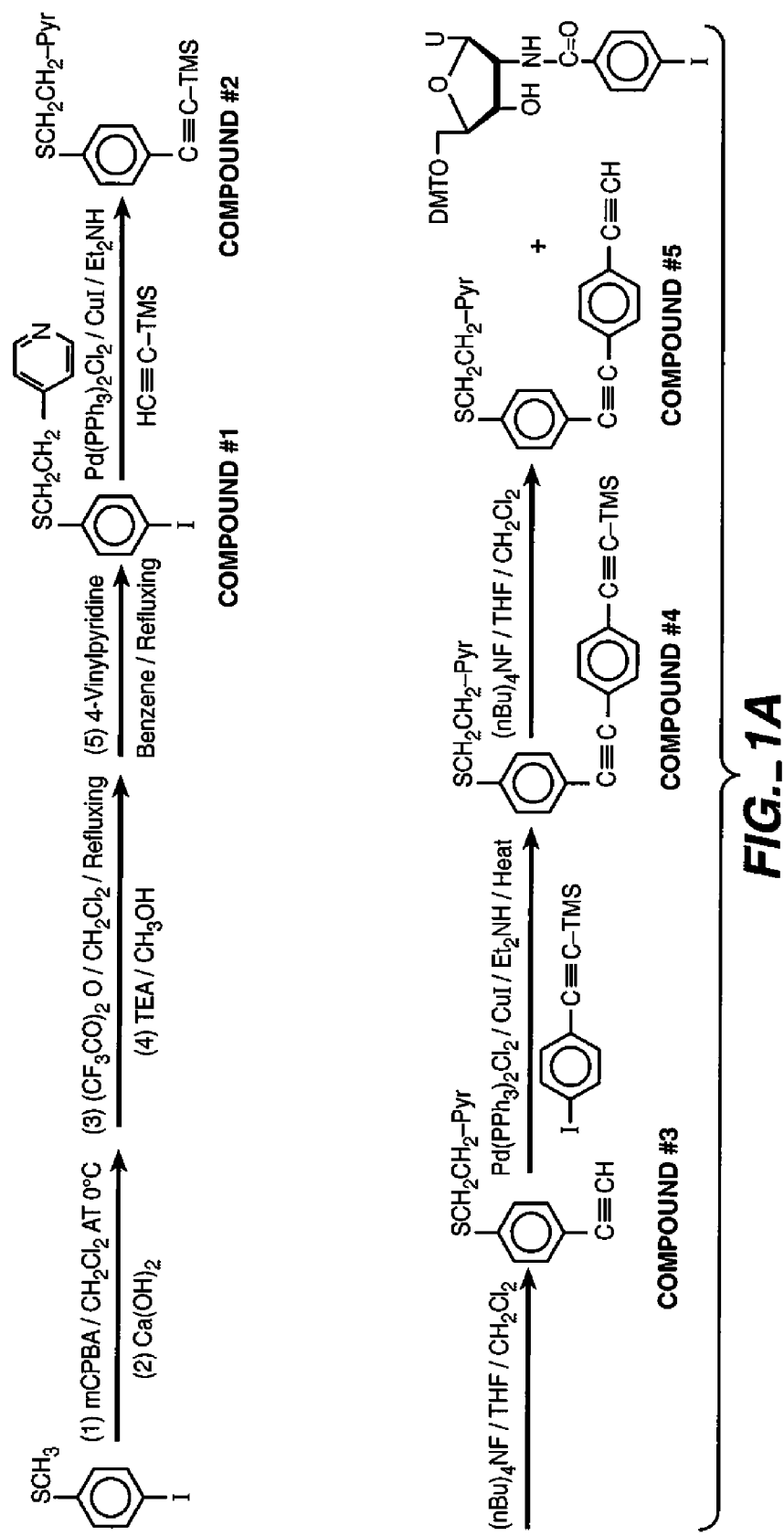
FIG._1A

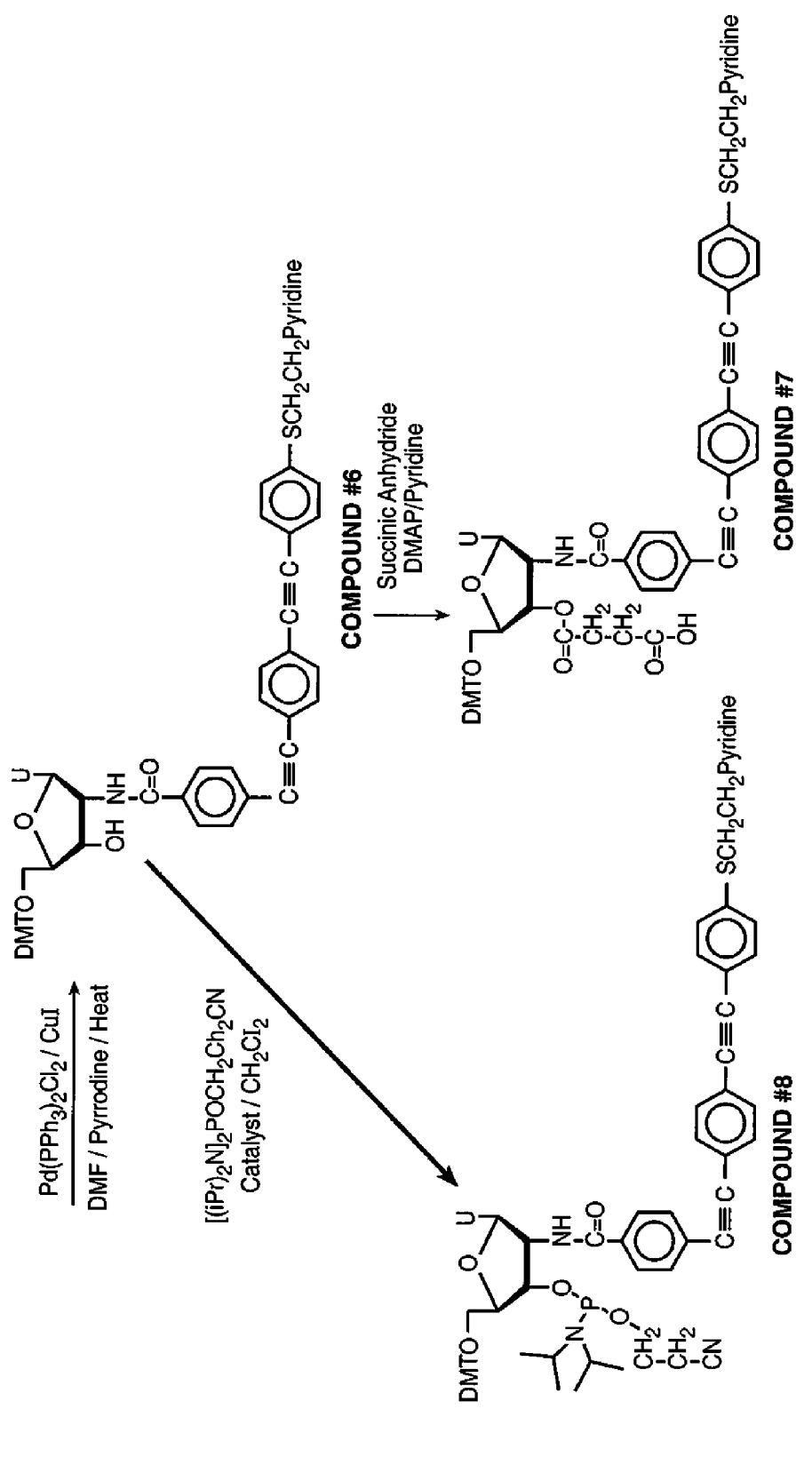
FIG._1B

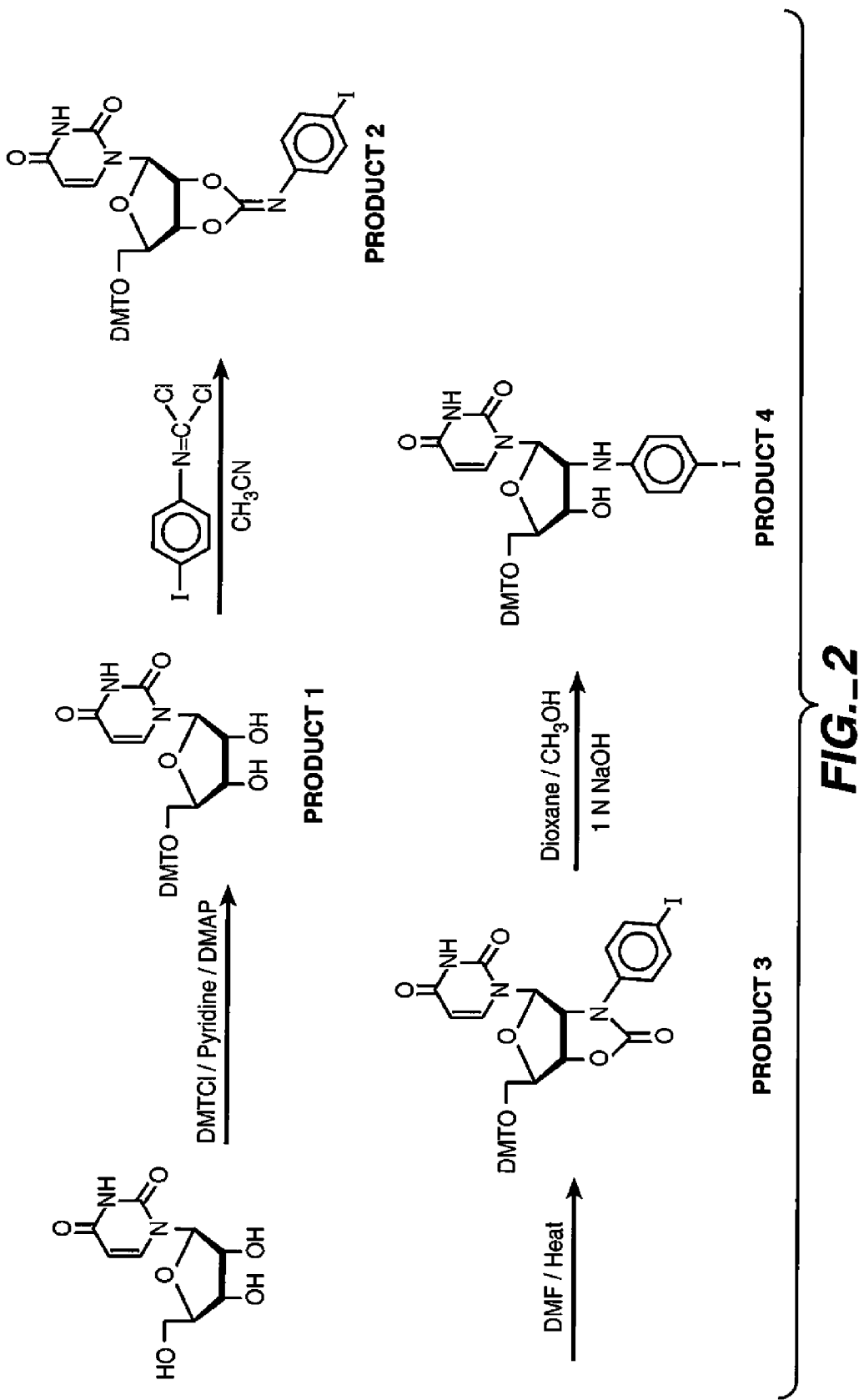
FIG._2

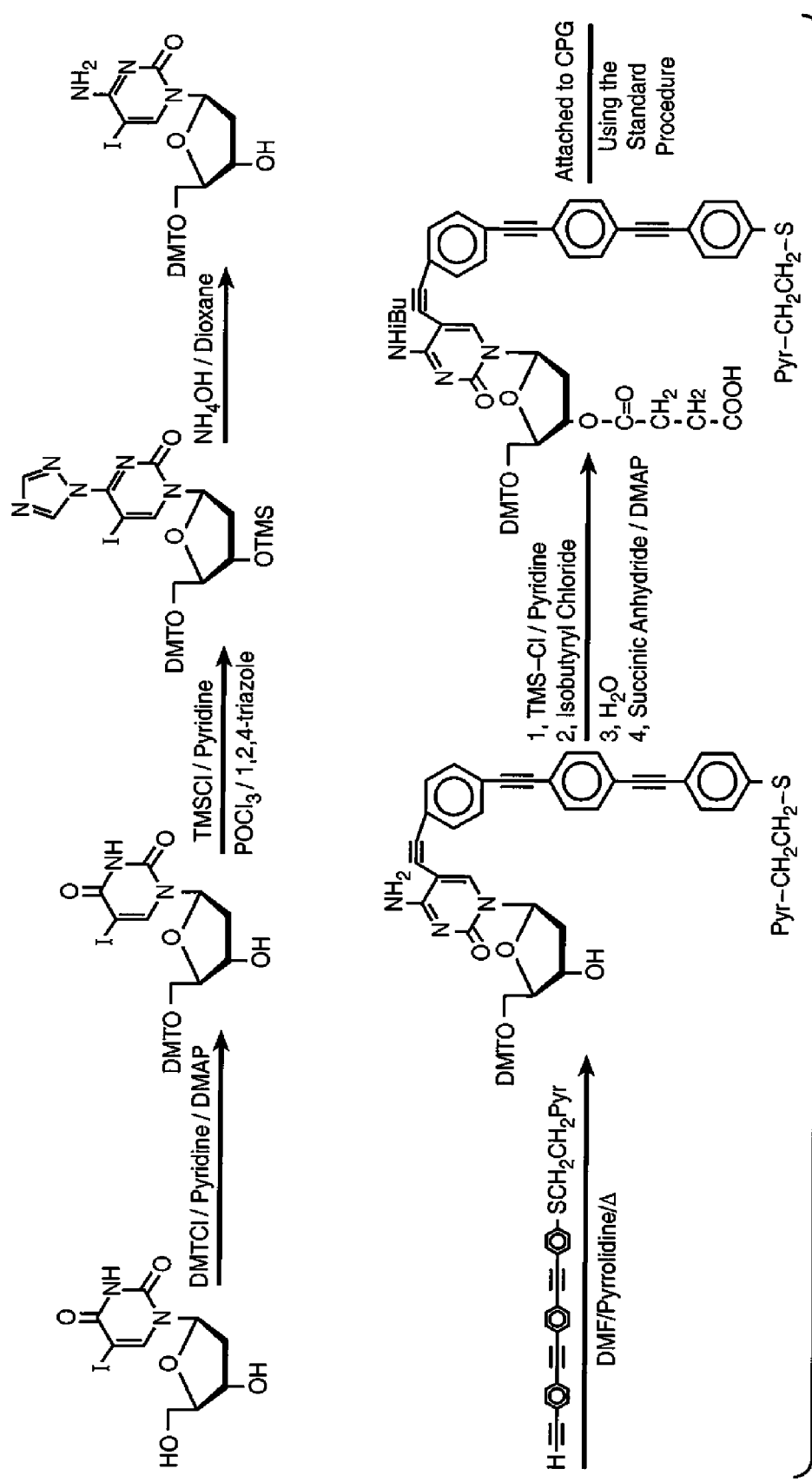
FIG._3

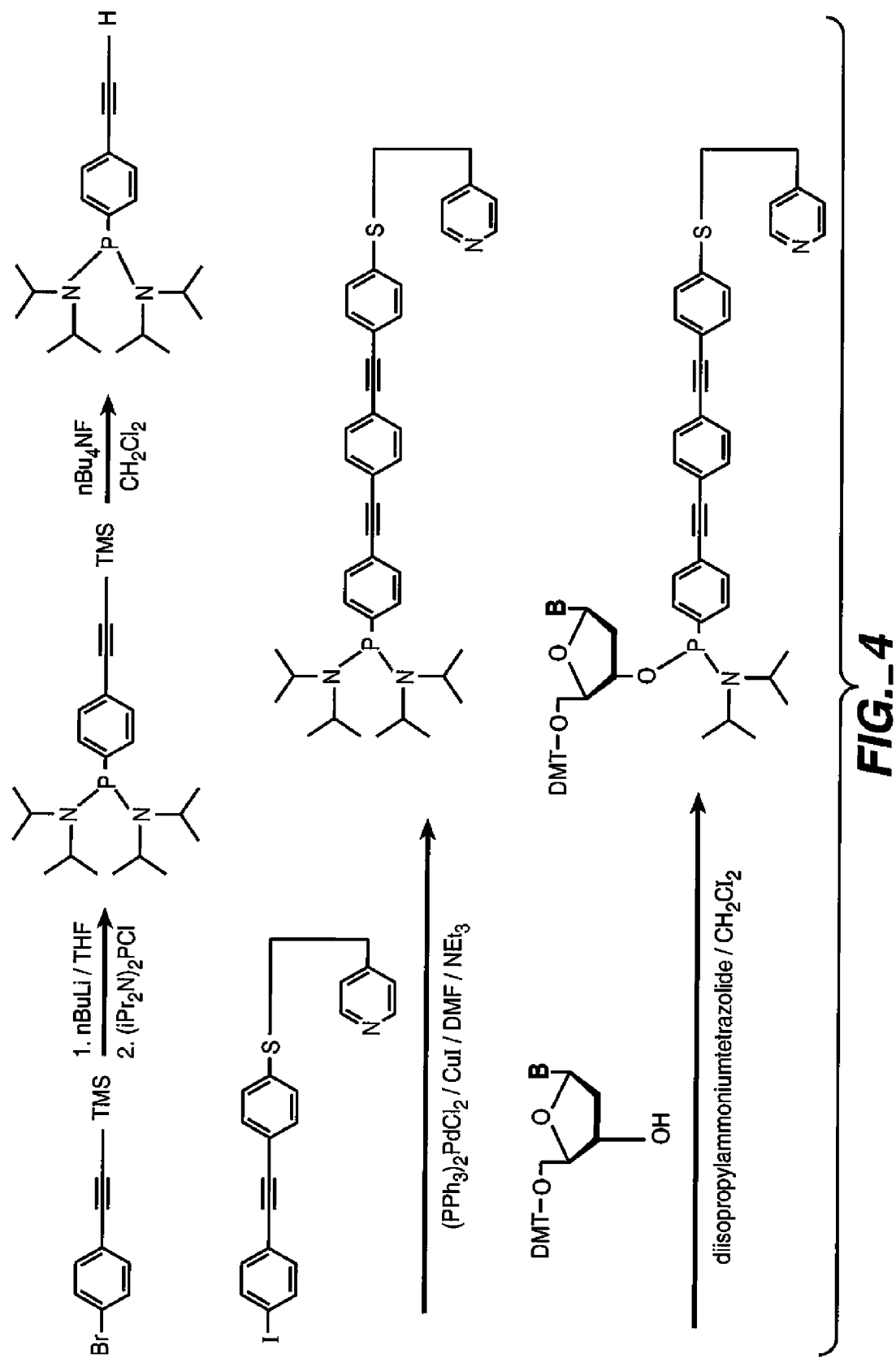
FIG._4

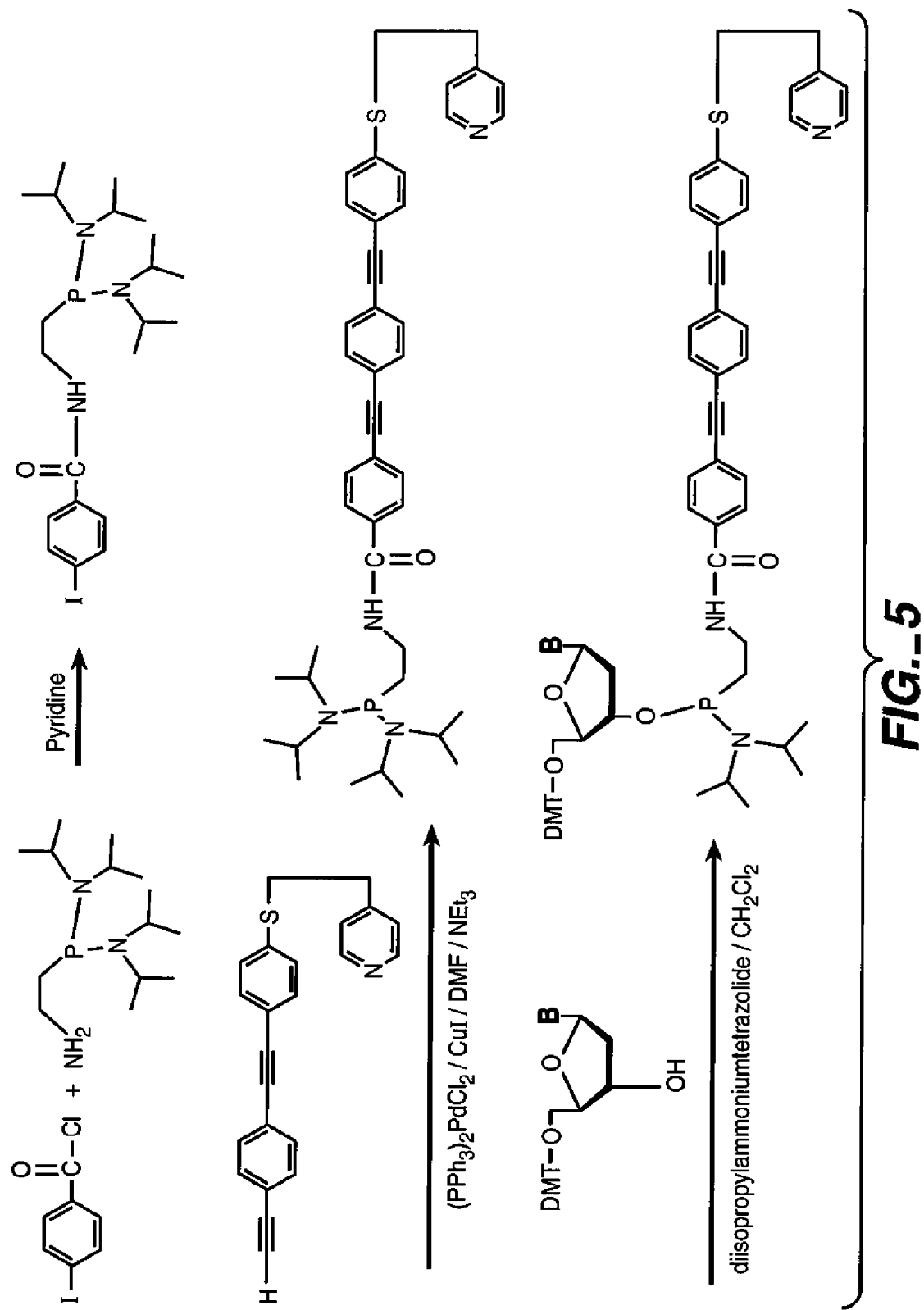
FIG._5

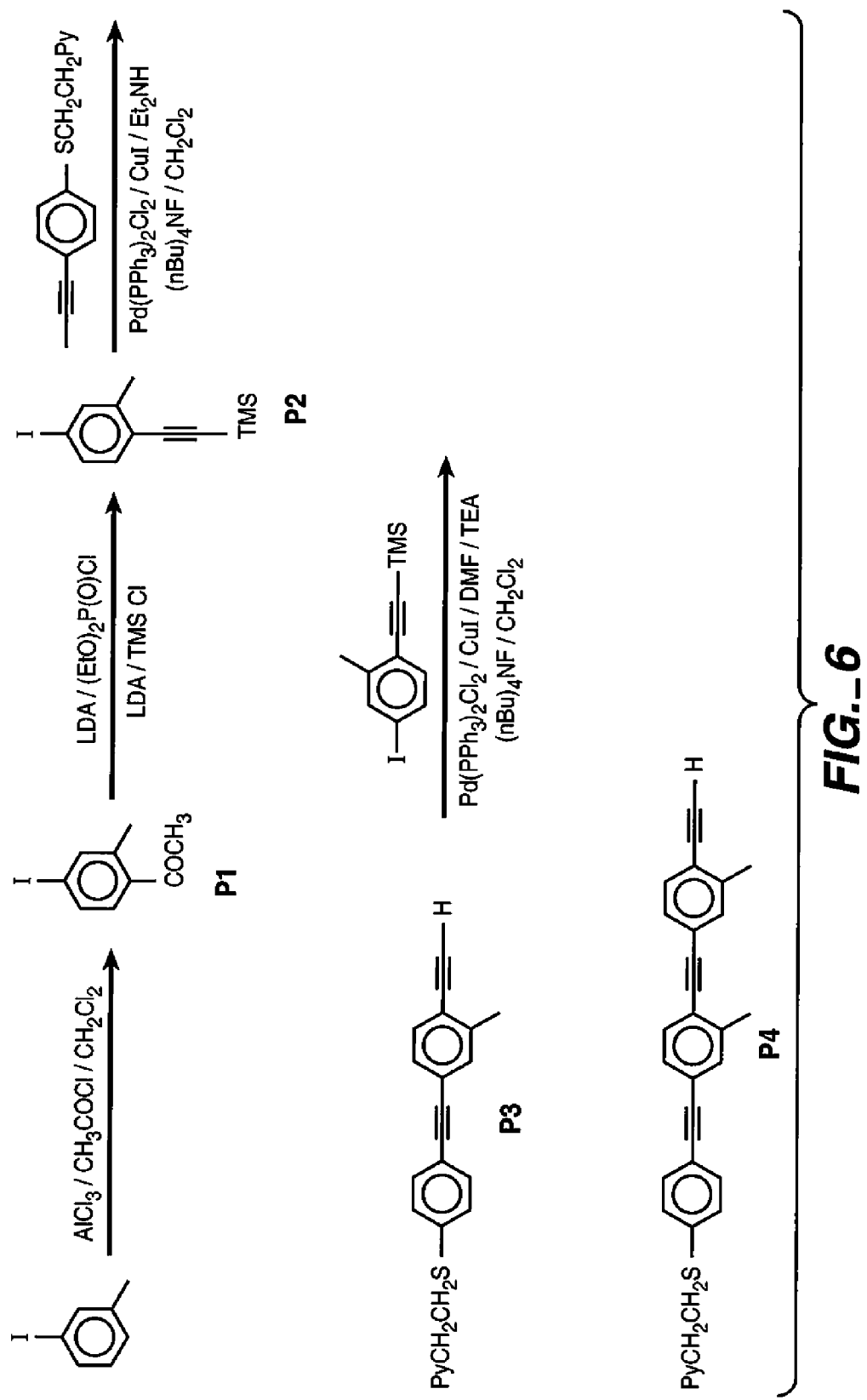
FIG._6

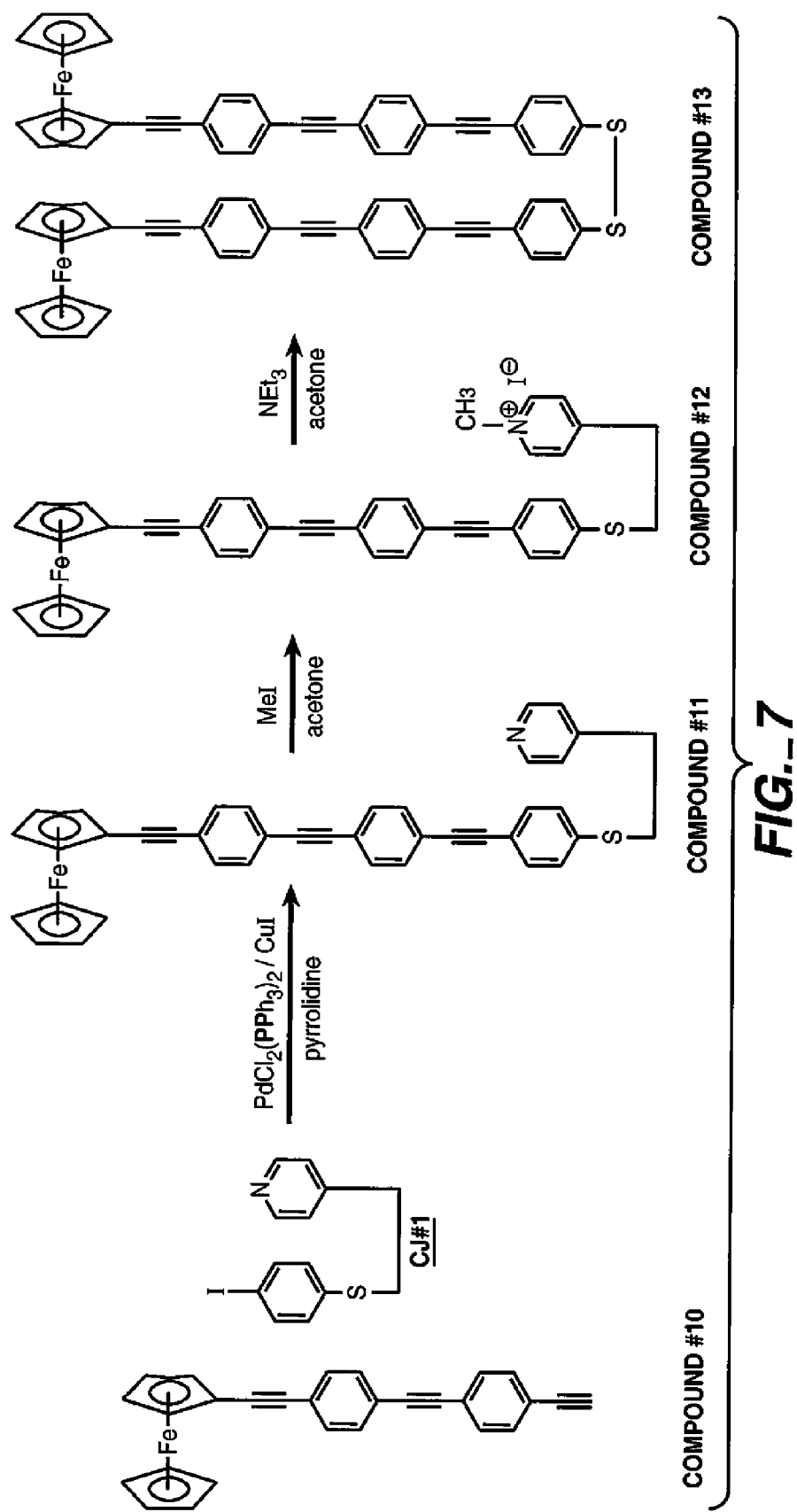
FIG._7

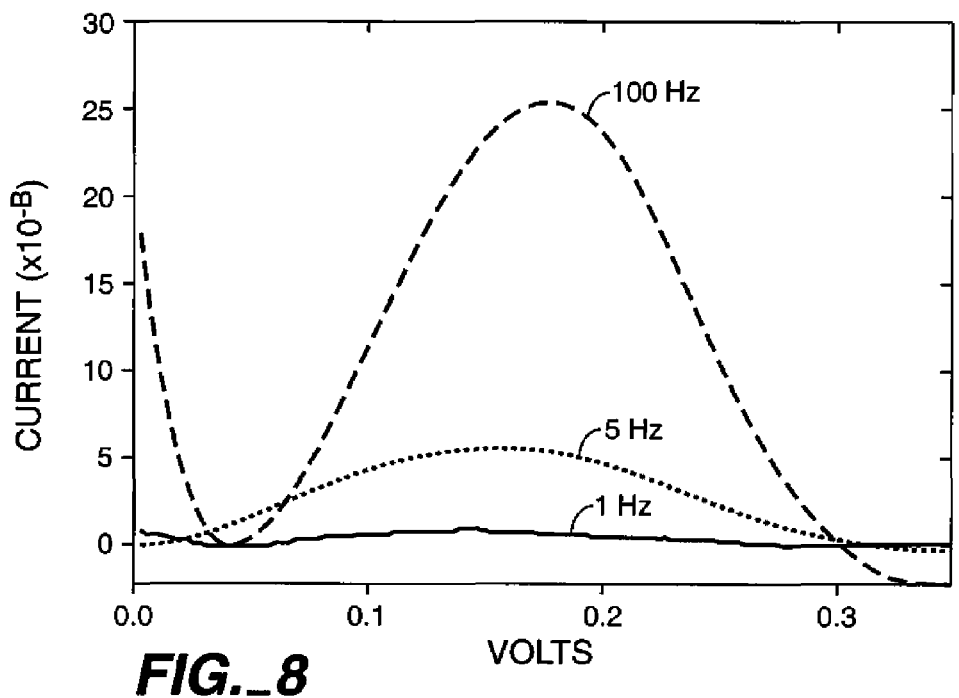
FIG._8
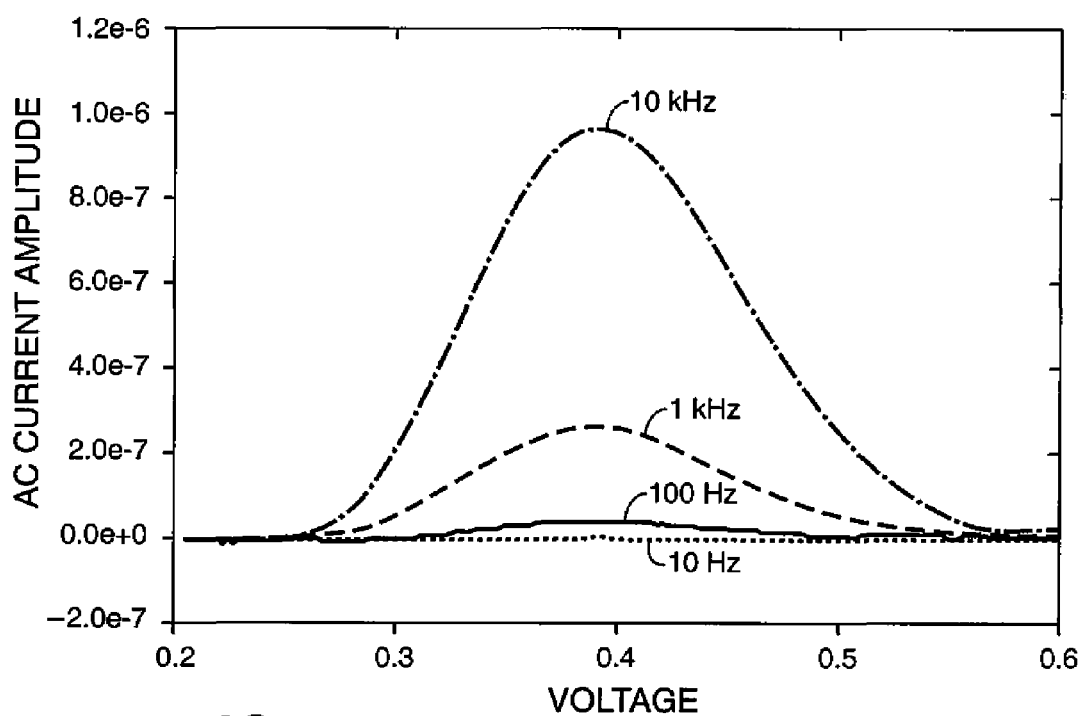
FIG._9A

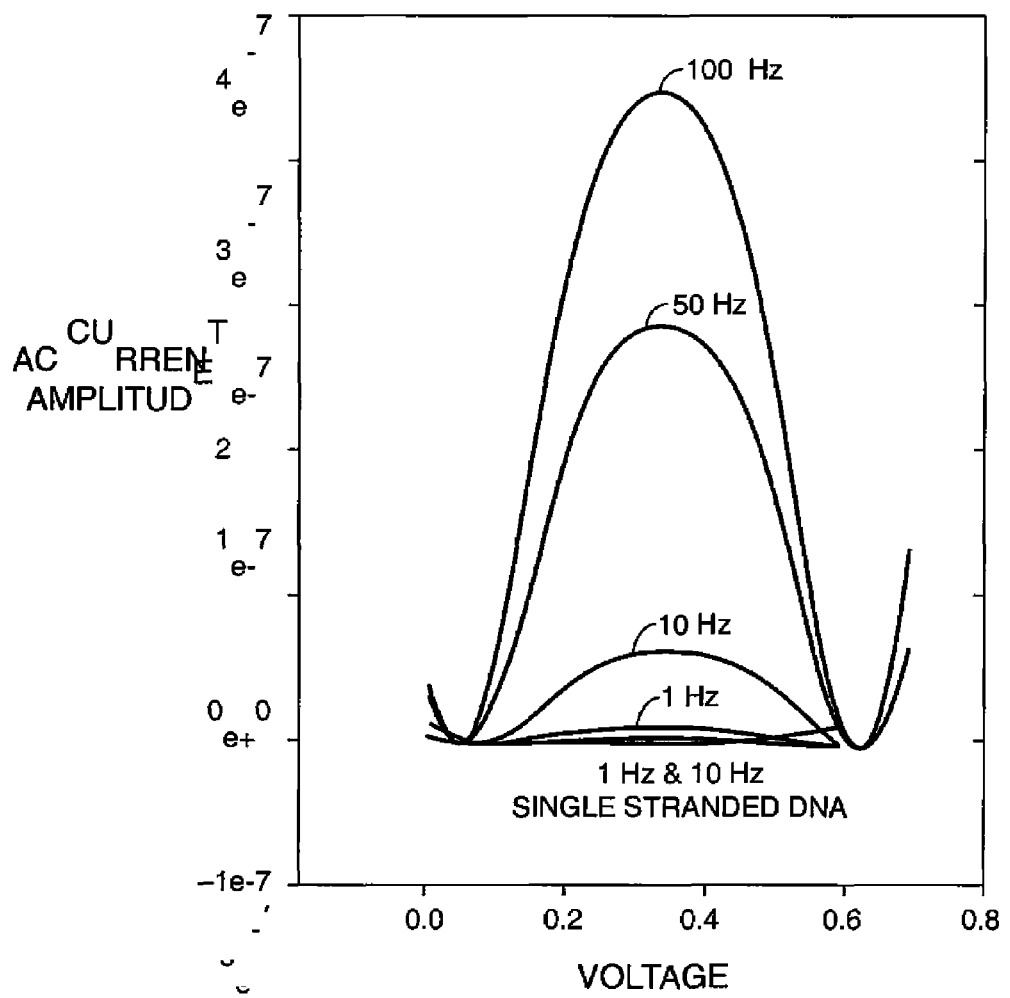
FIG._9B

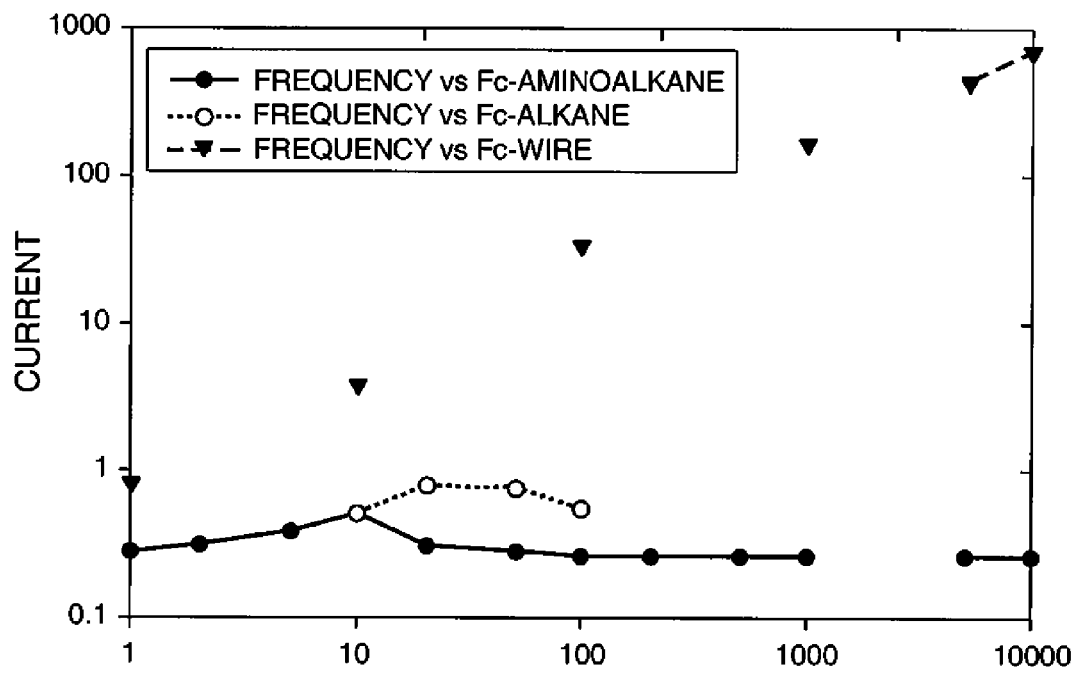
FIG._10
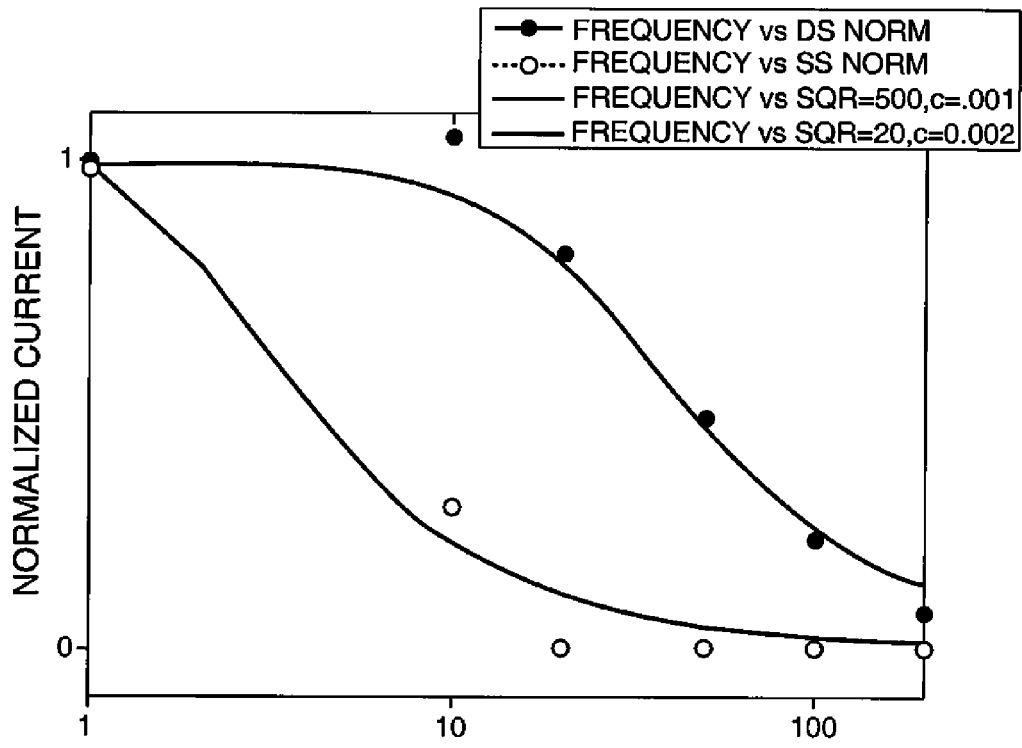
FIG._11

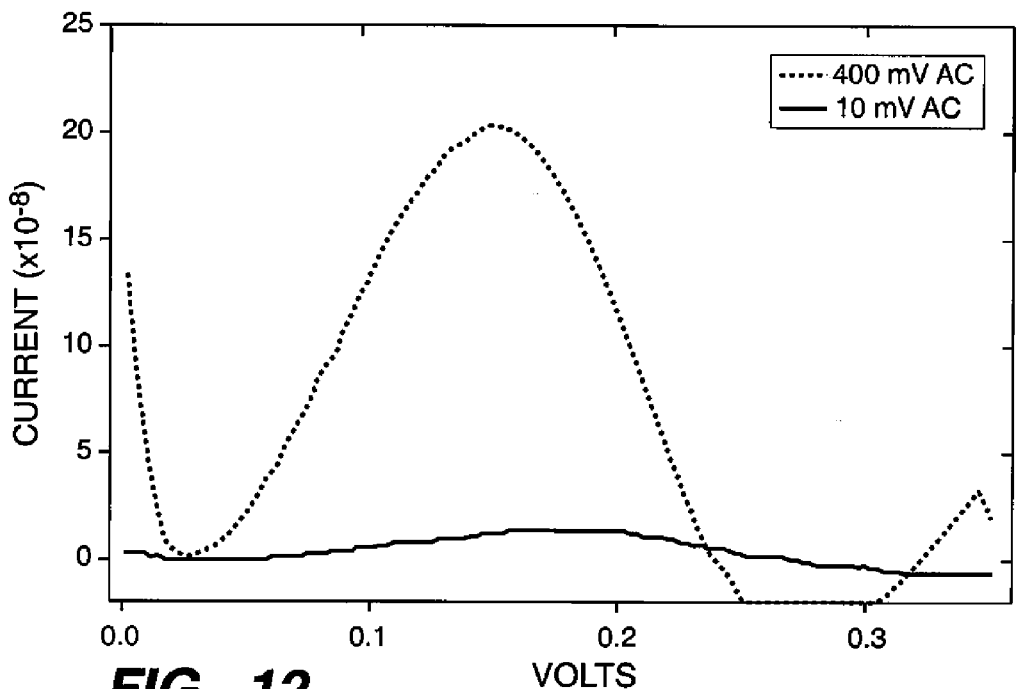
FIG._12
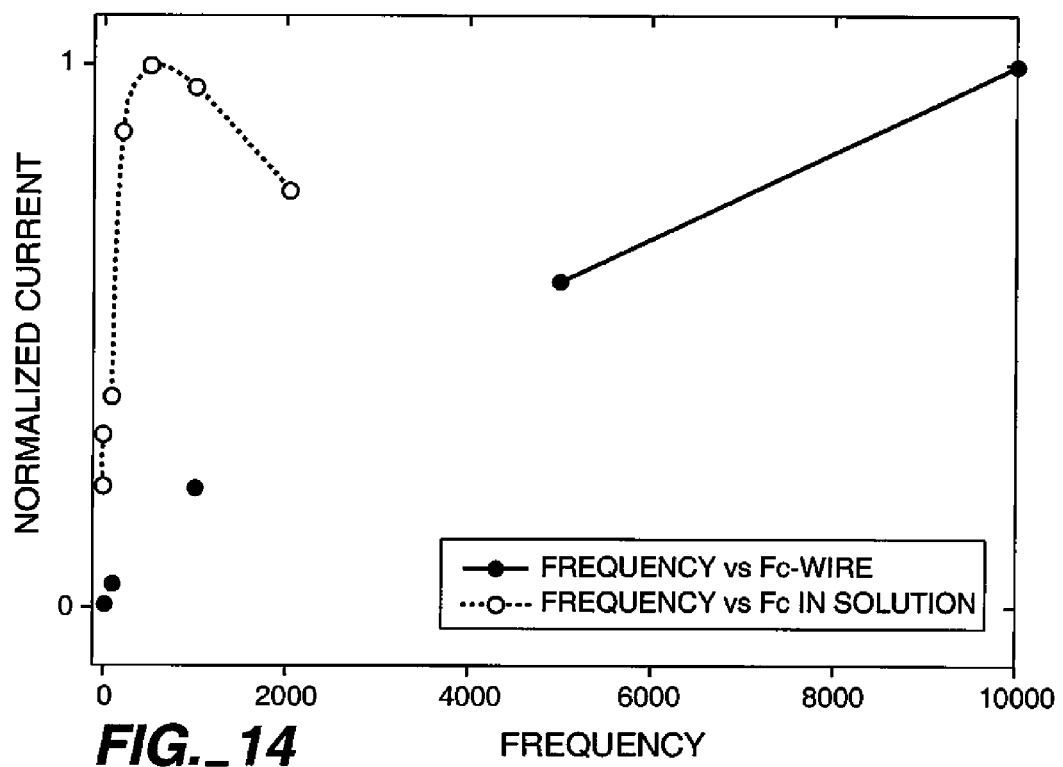
FIG._14

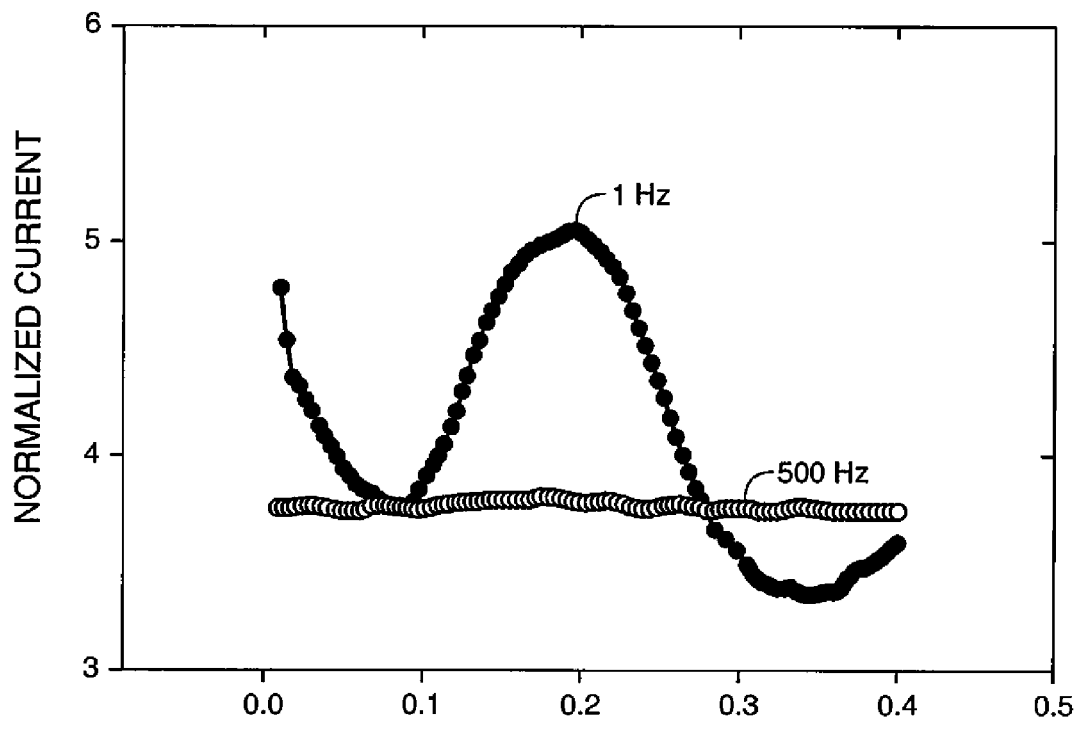
FIG._13A
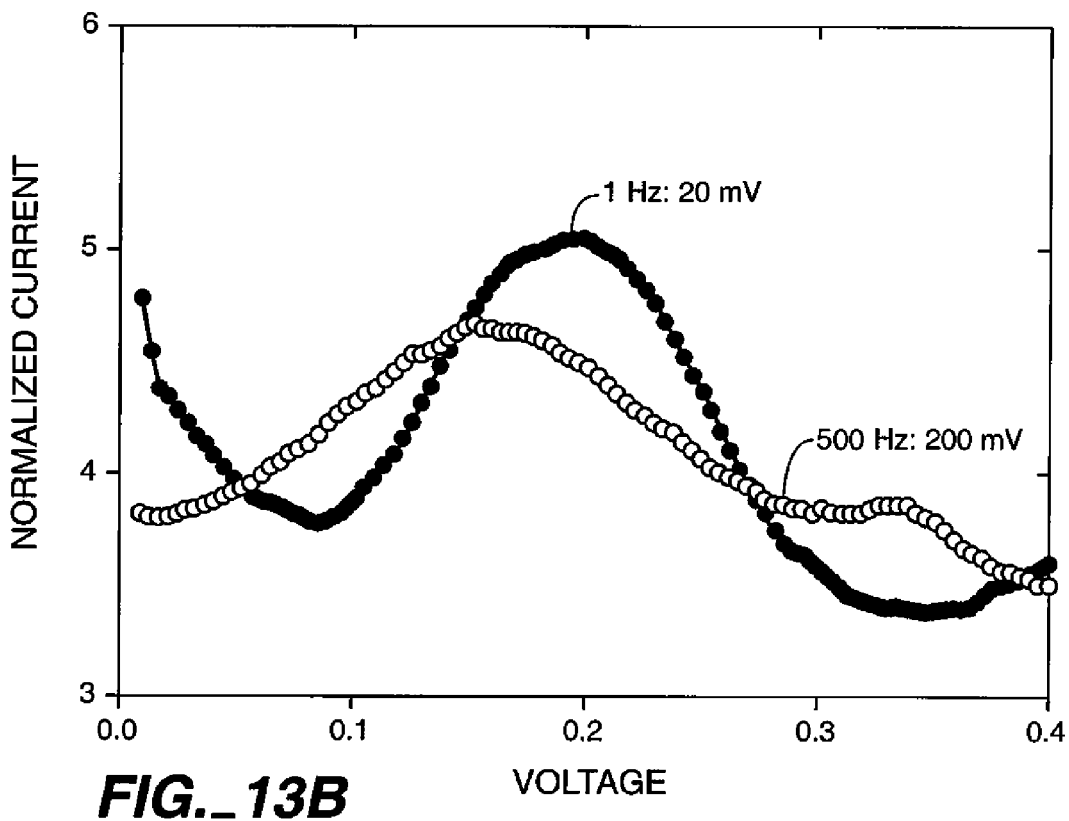
FIG._13B

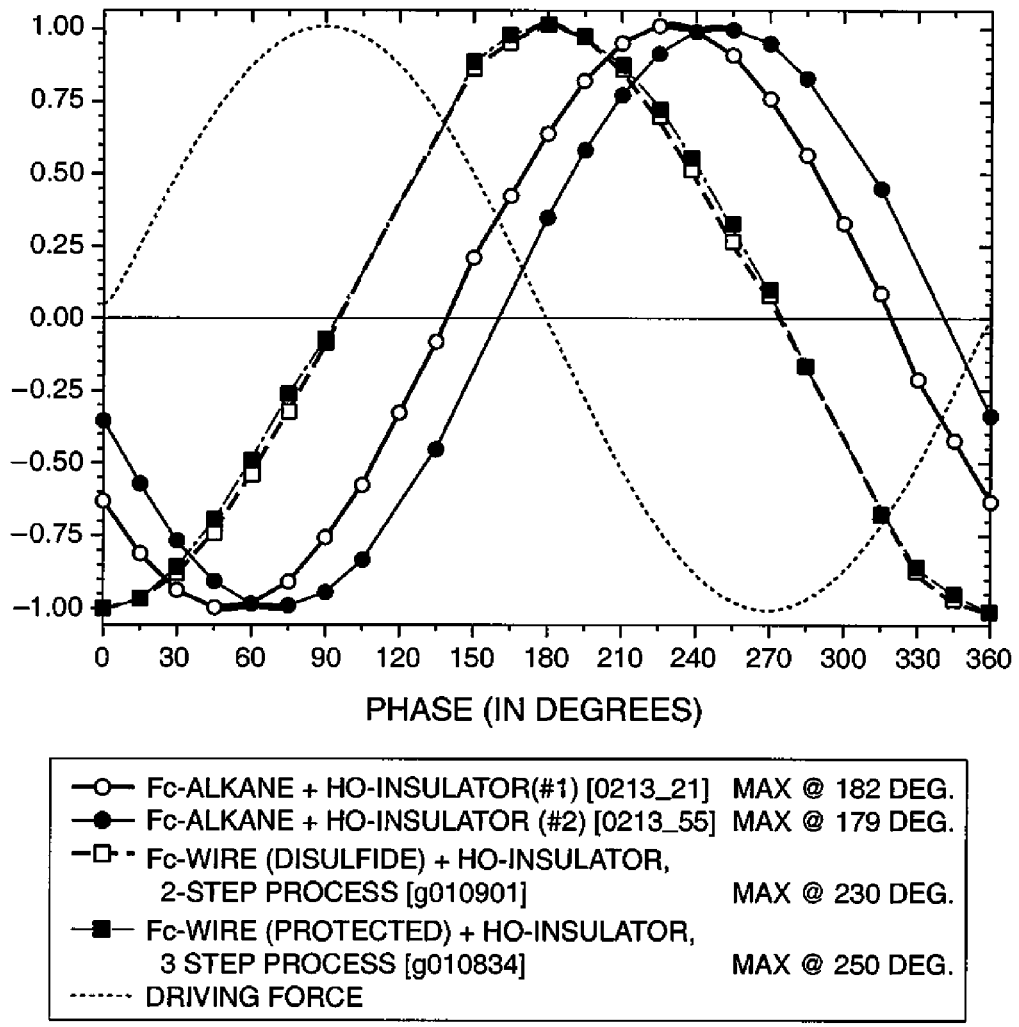
FIG._15A

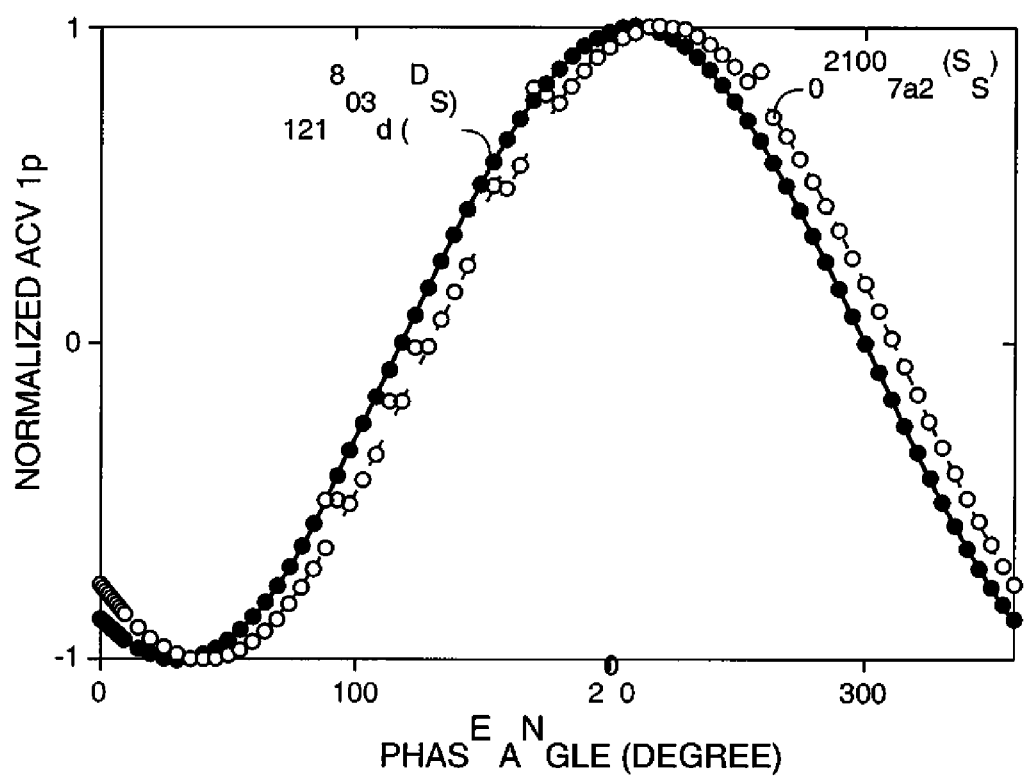
FIG._15B

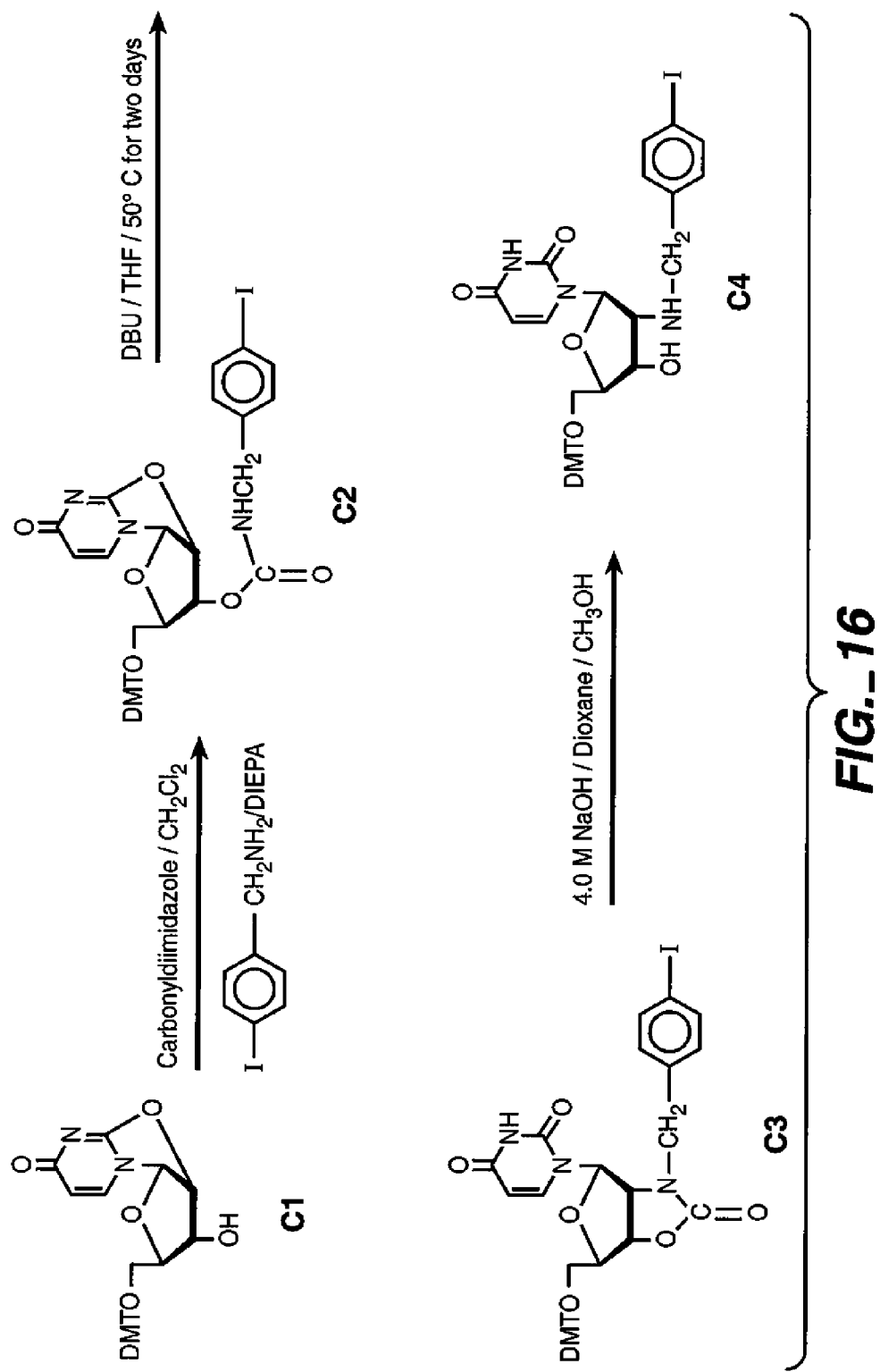
FIG._16

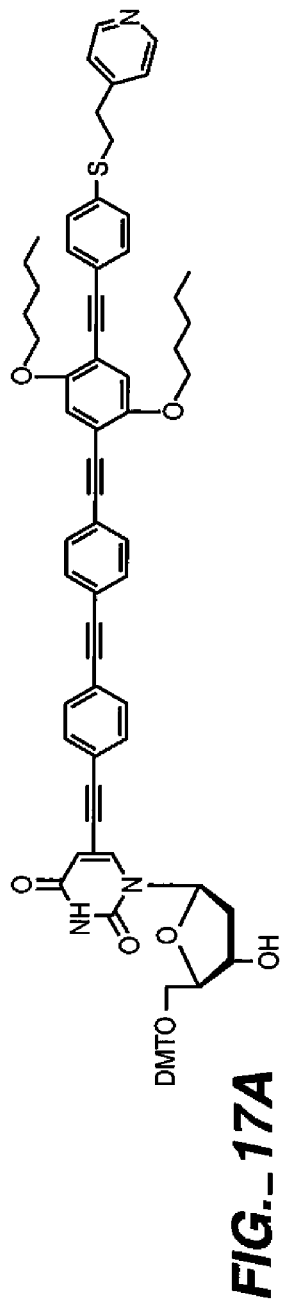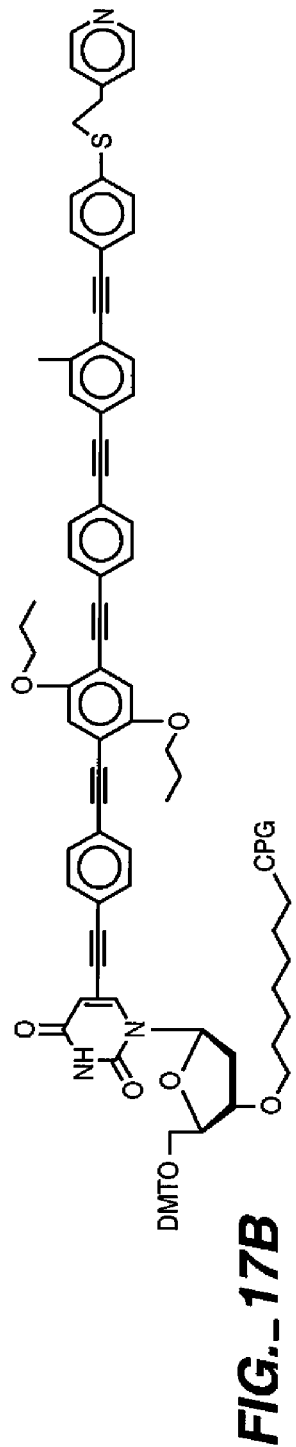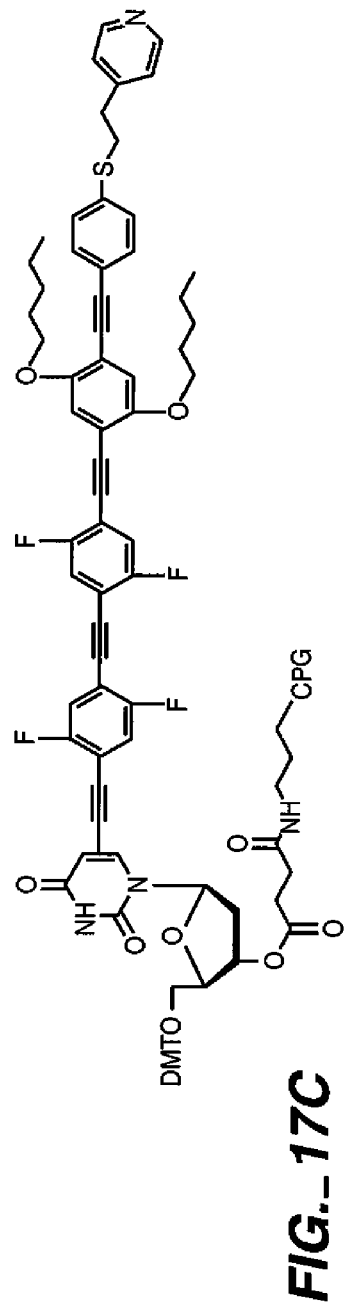
FIG._17A
FIG._17B
FIG._17C

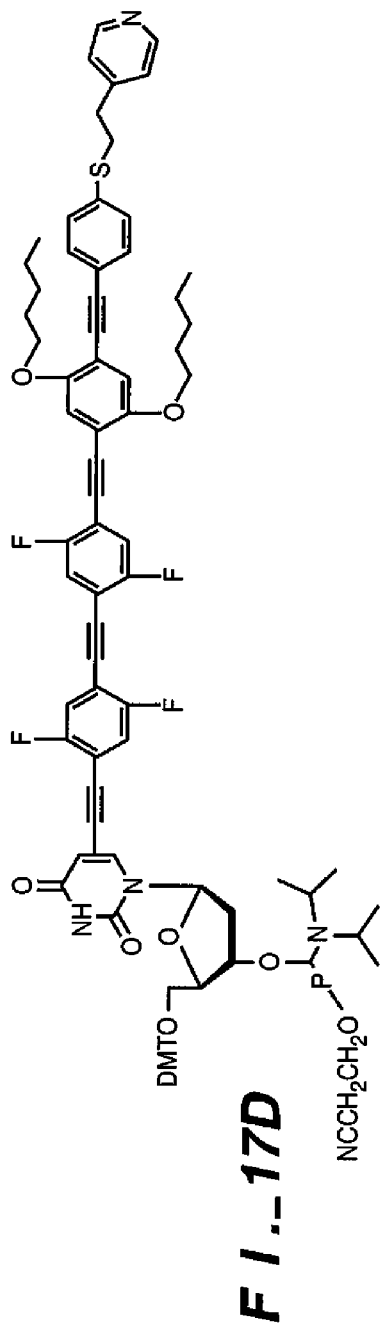
FIG. _17D
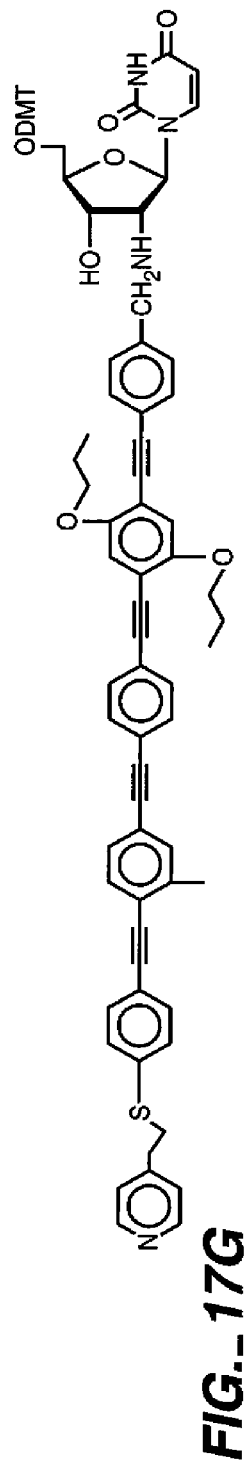
FIG. _17G
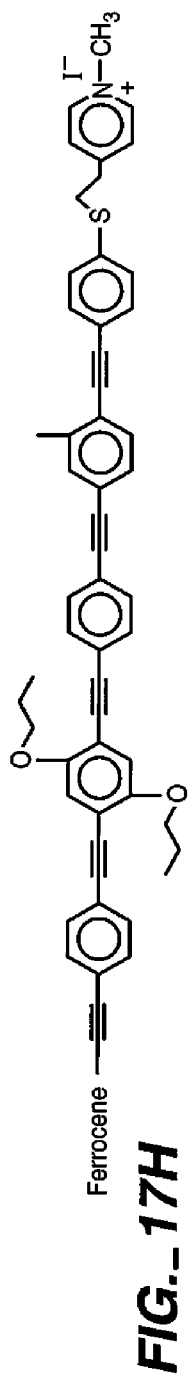
FIG. _17H

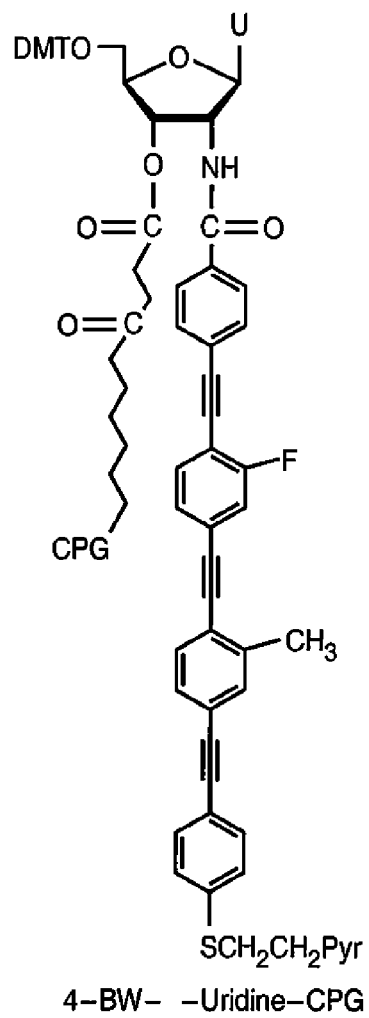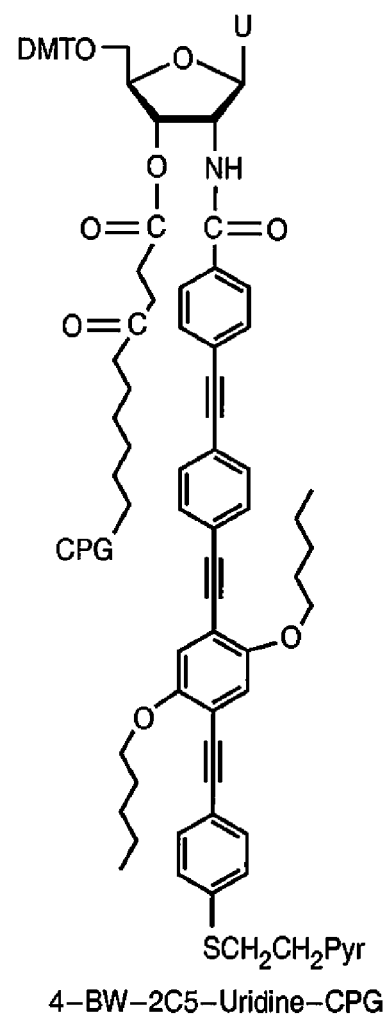
4-BW- -Uridine-CPG
FIG._17E
4-BW-2C5-Uridine-CPG
FIG._17F

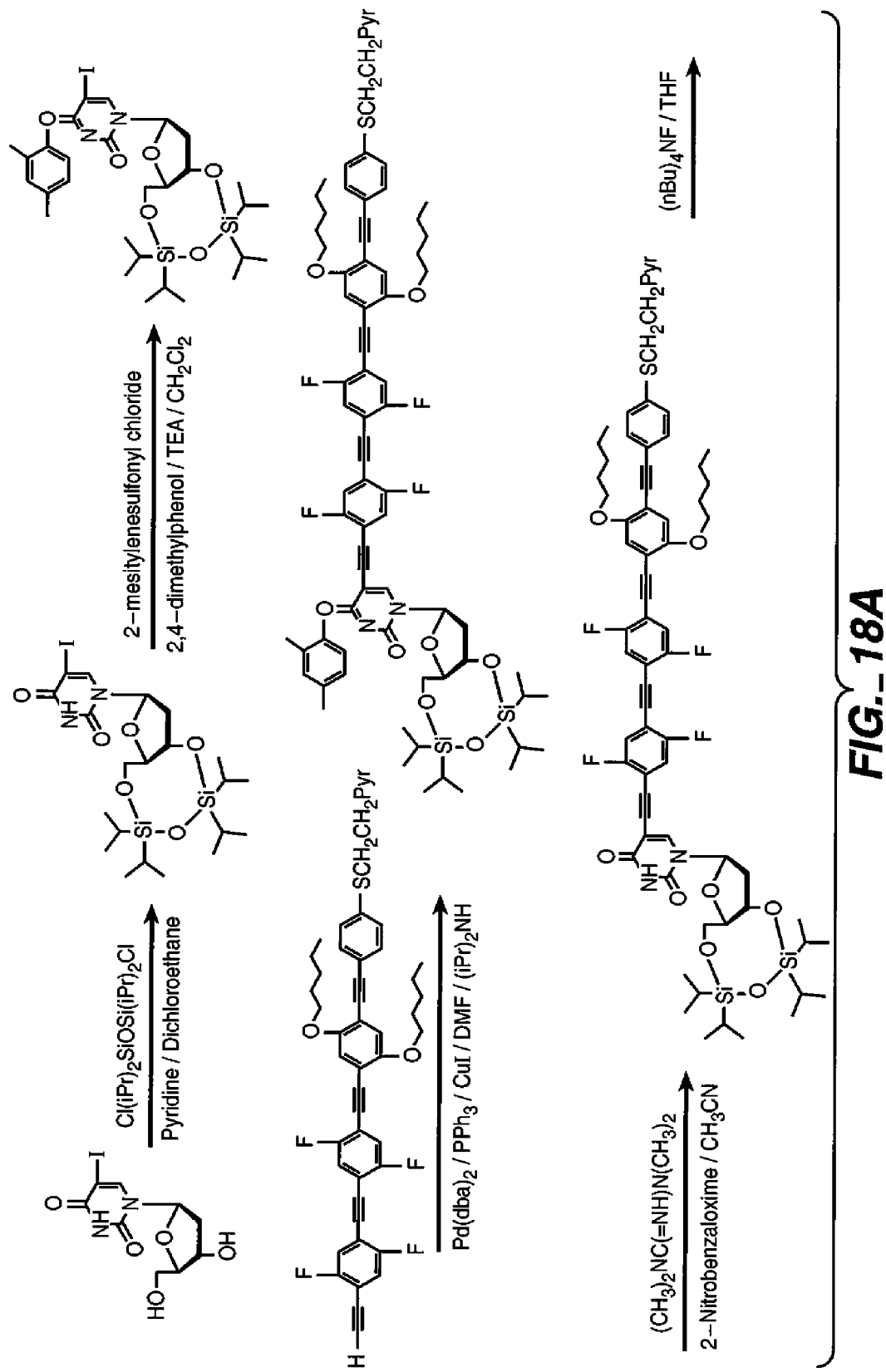
FIG. _18A

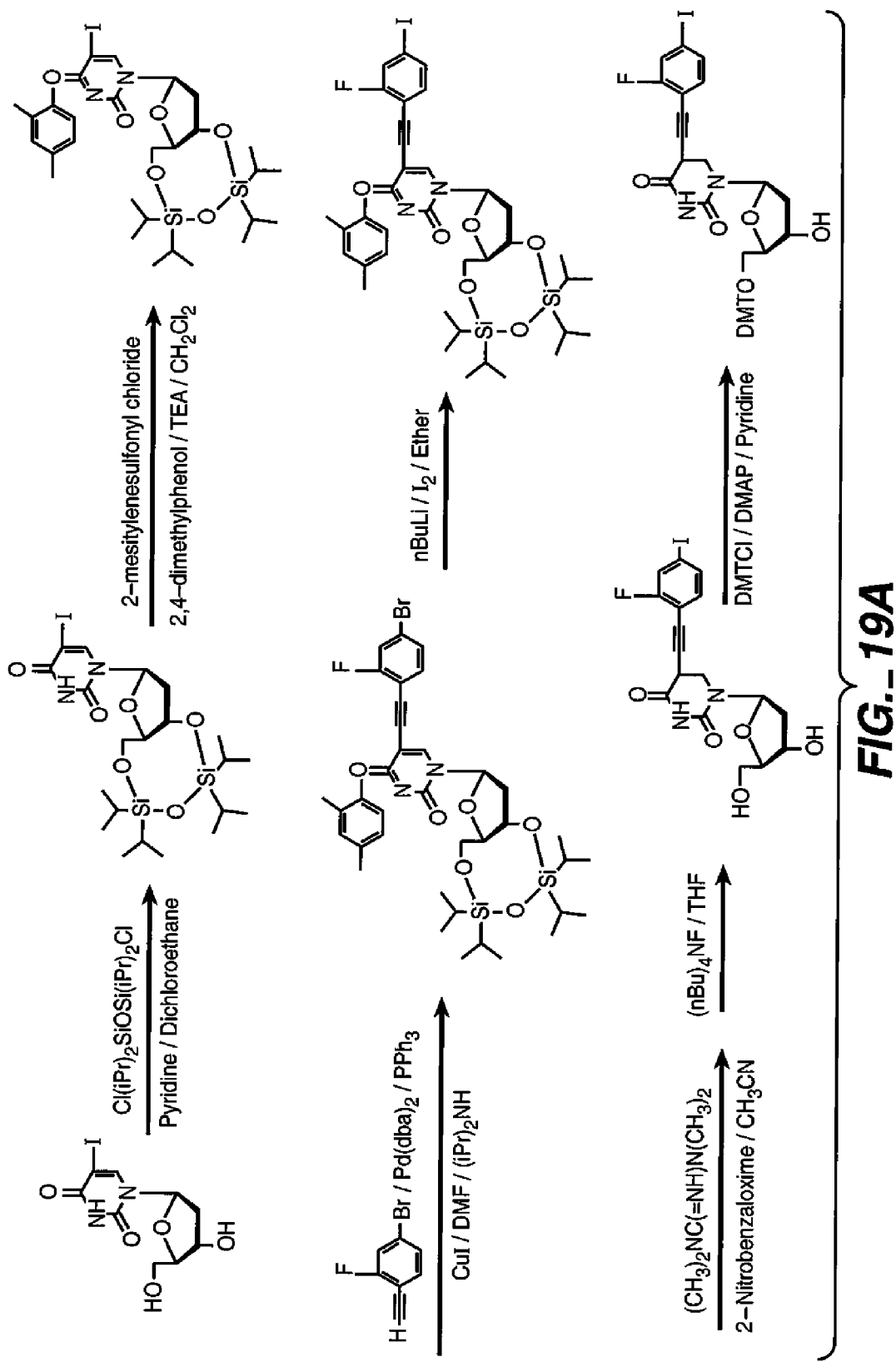
FIG._19A

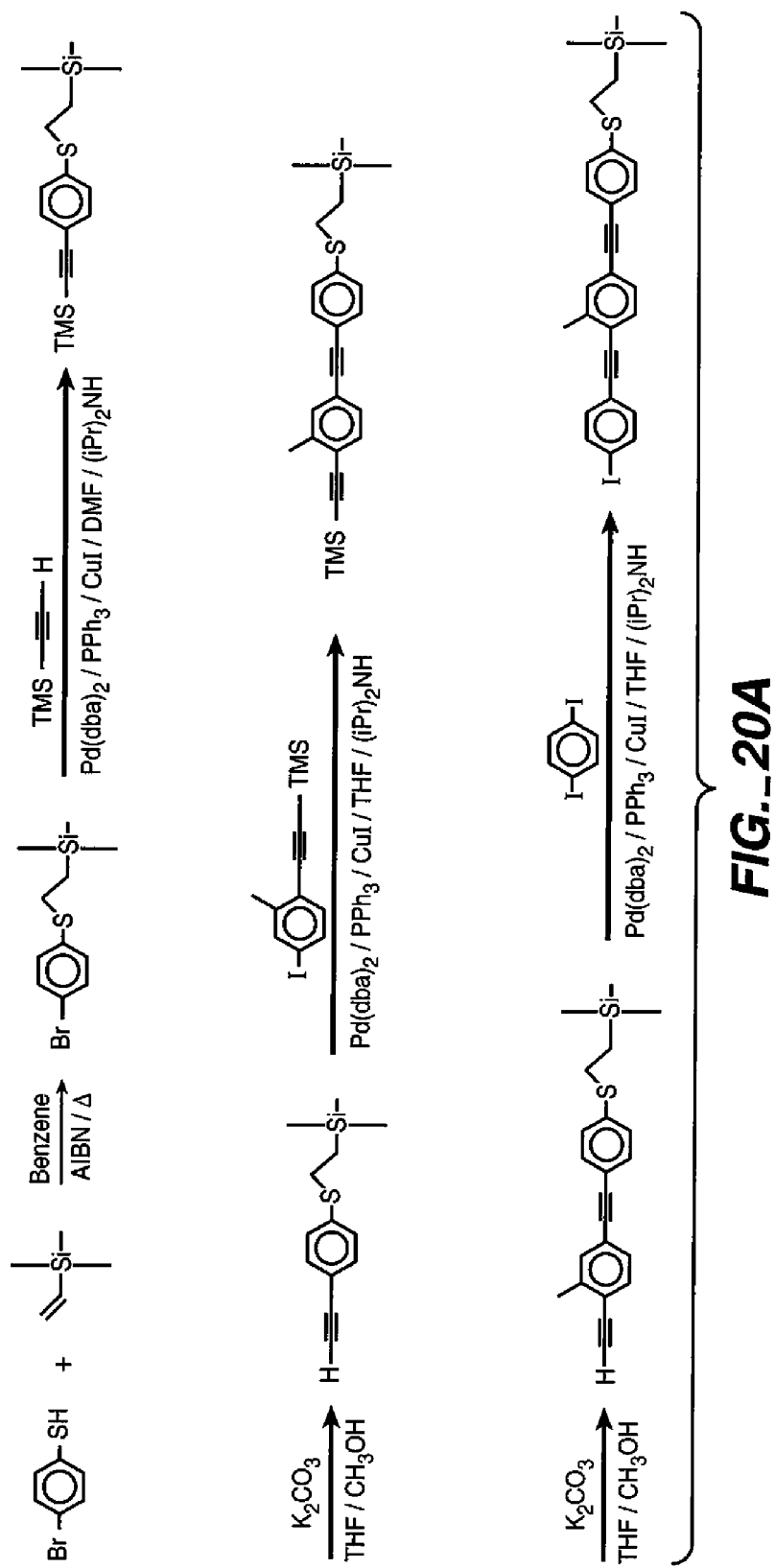
FIG._20A

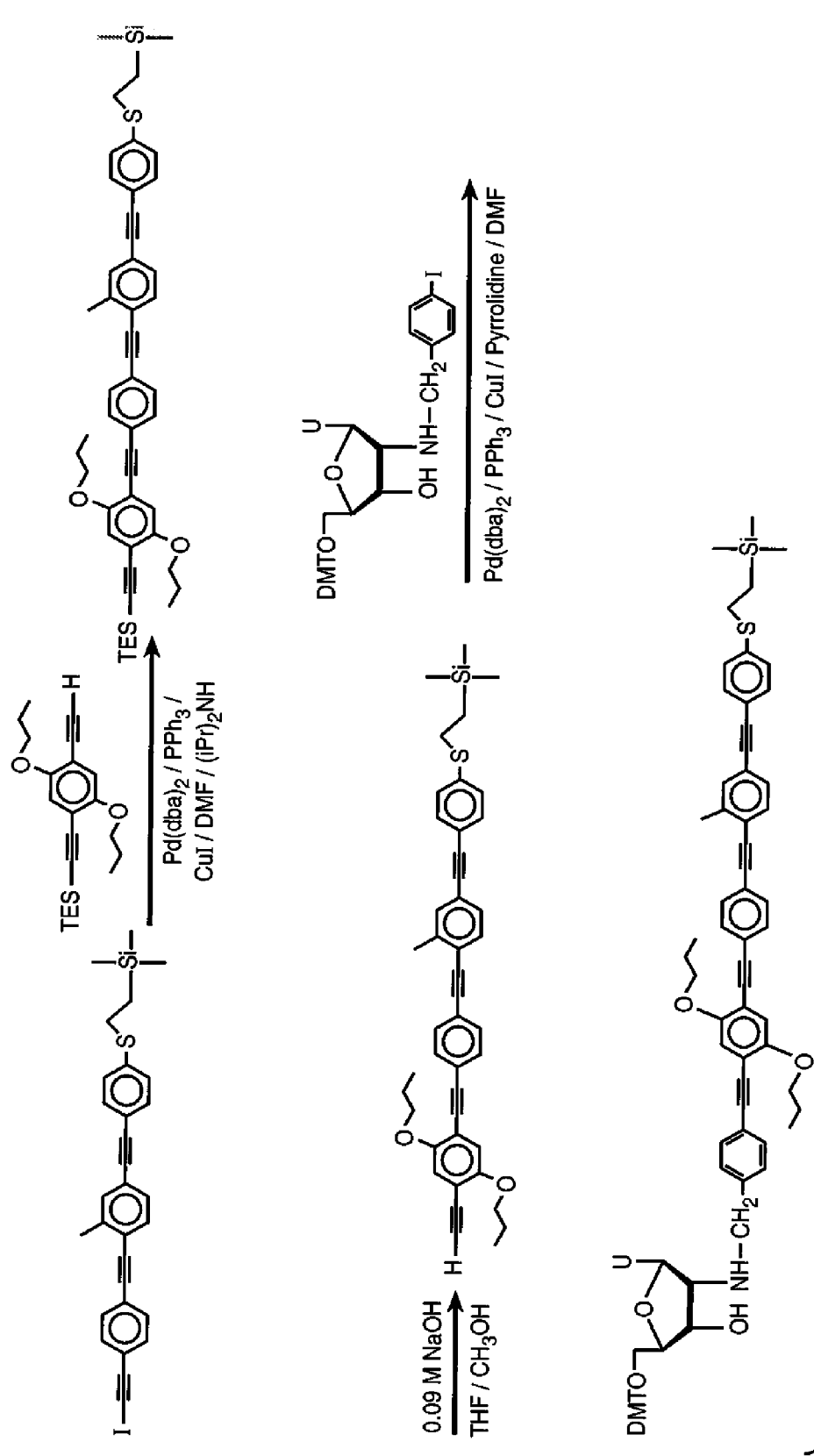
FIG._21

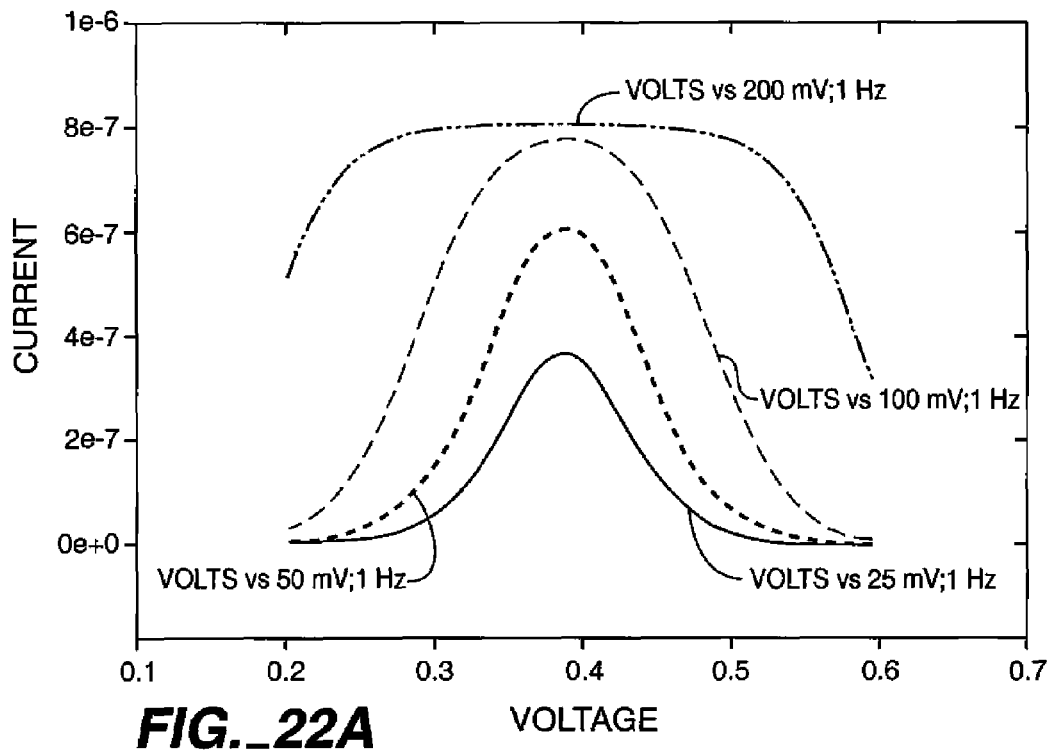
FIG._22A
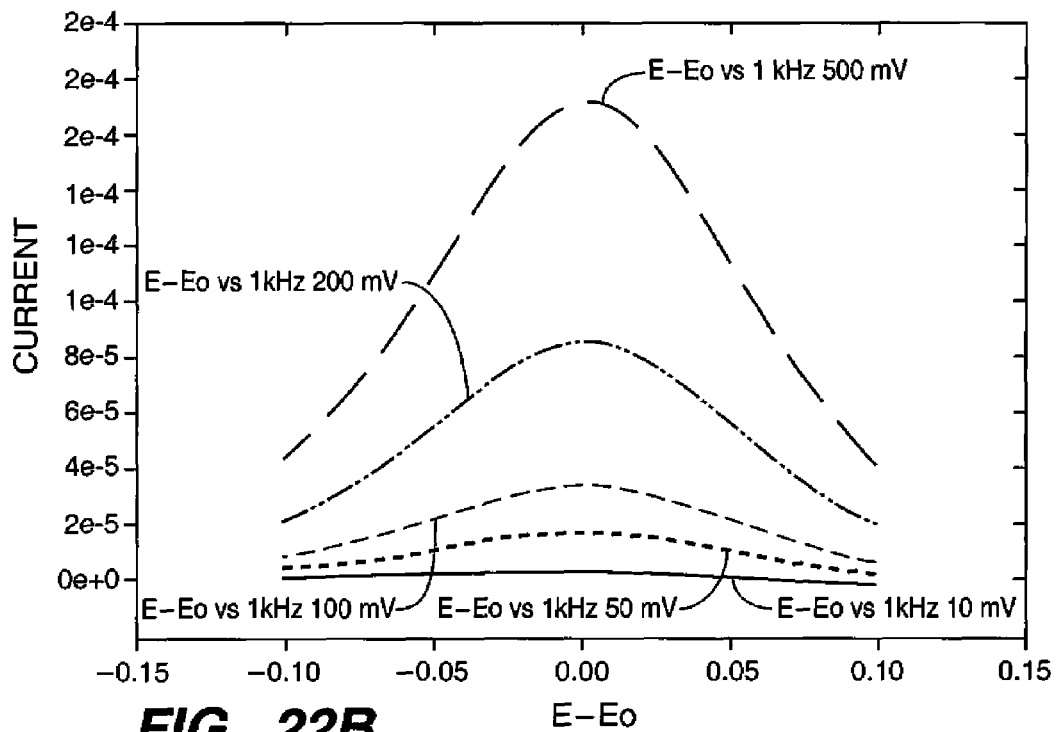
FIG._22B

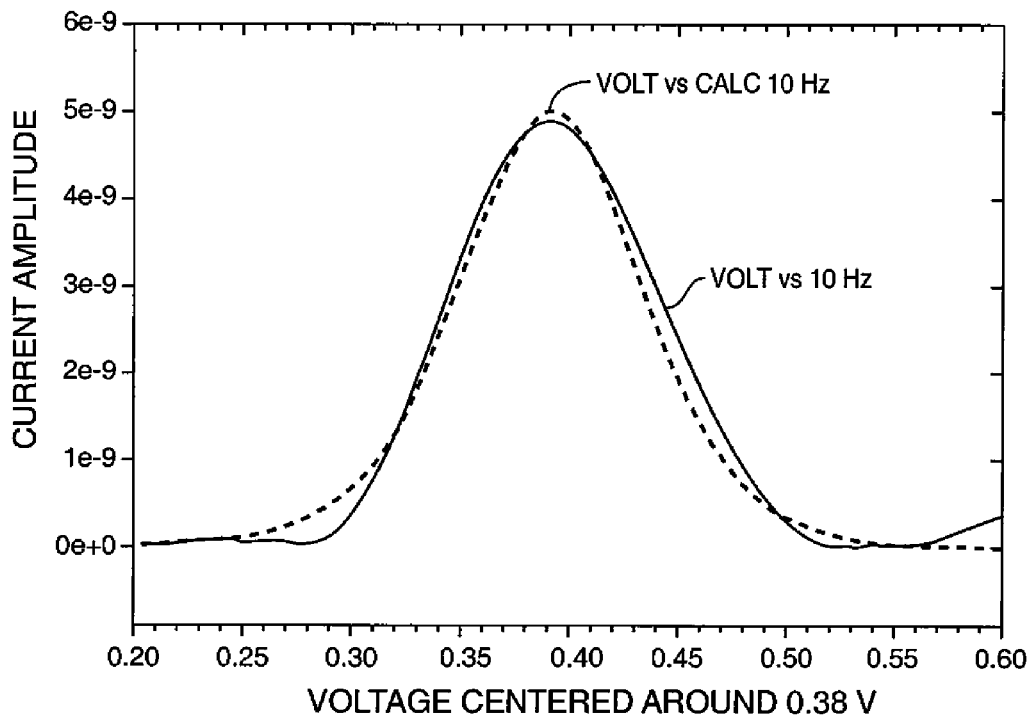
FIG._23A
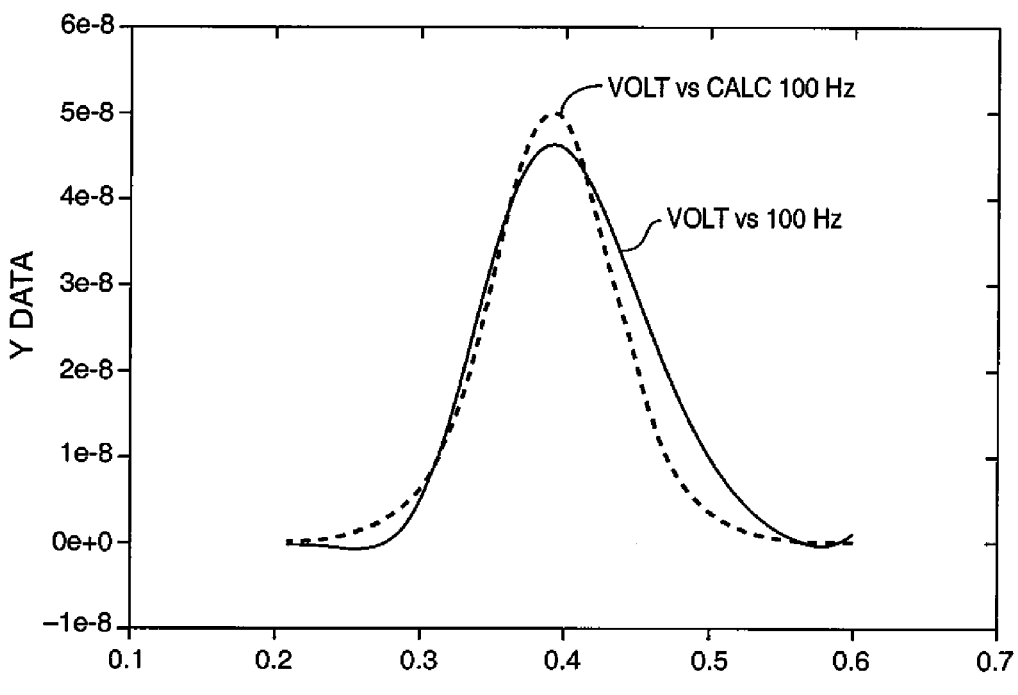
FIG._23B

AC/DC VOLTAGE APPARATUS FOR DETECTION OF NUCLEIC ACIDS

CROSS REFERENCE TO RELATED APPLICATIONS

This is a continuing application of provisional application Ser. No. 60/040,155 filed 7 Mar. 1997.

FIELD OF THE INVENTION

The invention relates to nucleic acids covalently coupled to electrodes via conductive oligomers. More particularly, the invention is directed to the site-selective modification of nucleic acids with electron transfer moieties and electrodes to produce a new class of biomaterials, and to methods of making and using them.

BACKGROUND OF THE INVENTION

The detection of specific nucleic acids is an important tool for diagnostic medicine and molecular biology research. Gene probe assays currently play roles in identifying infectious organisms such as bacteria and viruses, in probing the expression of normal genes and identifying mutant genes such as oncogenes, in typing tissue for compatibility preceding tissue transplantation, in matching tissue or blood samples for forensic medicine, and for exploring homology among genes from different species.

Ideally, a gene probe assay should be sensitive, specific and easily automatable (for a review, see Nickerson, Current Opinion in Biotechnology 4:48-51 (1993)). The requirement for sensitivity (i.e. low detection limits) has been greatly alleviated by the development of the polymerase chain reaction (PCR) and other amplification technologies which allow researchers to amplify exponentially a specific nucleic acid sequence before analysis (for a review, see Abramson et al., Current Opinion in Biotechnology, 4:41-47 (1993)).

Specificity, in contrast, remains a problem in many currently available gene probe assays. The extent of molecular complementarity between probe and target defines the specificity of the interaction. Variations in the concentrations of probes, of targets and of salts in the hybridization medium, in the reaction temperature, and in the length of the probe may alter or influence the specificity of the probe/target interaction.

It may be possible under some limited circumstances to distinguish targets with perfect complementarity from targets with mismatches, although this is generally very difficult using traditional technology, since small variations in the reaction conditions will alter the hybridization. New experimental techniques for mismatch detection with standard probes include DNA ligation assays where single point mismatches prevent ligation and probe digestion assays in which mismatches create sites for probe cleavage.

Finally, the automation of gene probe assays remains an area in which current technologies are lacking. Such assays generally rely on the hybridization of a labelled probe to a target sequence followed by the separation of the unhybridized free probe. This separation is generally achieved by gel electrophoresis or solid phase capture and washing of the target DNA, and is generally quite difficult to automate easily.

The time consuming nature of these separation steps has led to two distinct avenues of development. One involves the development of high-speed, high-throughput automatable electrophoretic and other separation techniques. The other involves the development of non-separation homogeneous gene probe assays.

PCT application WO 95/15971 describes novel compositions comprising nucleic acids containing electron transfer moieties, including electrodes, which allow for novel detection methods of nucleic acid hybridization.

SUMMARY OF THE INVENTION

Accordingly, it is an object of the invention to provide for improved methods and compositions of nucleic acids covalently attached to electrodes and at least one other electron transfer moiety.

In one aspect, the present invention provides methods for detecting the presence of a target sequence in a nucleic acid sample. The method comprises applying a first input signal comprising an AC component and a non-zero DC component to a hybridization complex comprising at least a target sequence and a first probe single stranded nucleic acid. The hybridization complex is covalently attached to a first electron transfer moiety comprising an electrode, and a second electron transfer moiety. The presence of the hybridization complex is detected by receiving an output signal characteristic of electron transfer through said hybridization complex.

In an alternative aspect, the invention provides methods as above wherein a first input signal comprising an AC component at a first frequency and a non-zero DC component is applied to a hybridization complex, and then a second input signal comprising an AC component at least a second frequency and a non-zero DC component is applied, such that the presence of the hybridization complex can be detected.

In a further aspect of the invention, the methods utilize a first input signal comprising an AC component and a first non-zero DC component applied to a hybridization complex, followed by a second input signal comprising said AC component and at least a second non-zero DC component.

In an additional aspect, the invention provides methods that utilize a first input signal comprising an AC component at a first voltage amplitude, and a second input signal comprising said AC component at a second voltage amplitude applied to the hybridization complex.

In an additional aspect, the invention provides methods utilizing hybridization complex comprising a single stranded nucleic acid covalently attached to both a first electron transfer moiety comprising an electrode, and a second electron transfer moiety, and a target sequence hybridized to said single stranded nucleic acid.

In a further aspect, the hybridization complexes comprise a single stranded nucleic acid covalently attached via a conductive oligomer to a first electron transfer moiety comprising an electrode, and a target sequence hybridized to said single stranded nucleic acid, and a second electron transfer moiety.

In a further aspect, the invention provides apparatus for the detection of target nucleic acids in a test sample, comprising a test chamber comprising a first and a second measuring electrode, wherein the first measuring electrode comprises a covalently attached conductive oligomer covalently attached to a single stranded nucleic acid, and an AC/DC voltage source electrically connected to the test chamber.

In an additional aspect, the invention provides apparatus comprising a test chamber comprising a first and a second measuring electrode, wherein the first measuring electrode comprises a covalently attached single stranded nucleic acid comprising a covalently attached second electron transfer moiety, and an AC/DC voltage source electrically connected to the test chamber.

BRIEF DESCRIPTION OF THE DRAWINGS

FIG. 1 depicts the synthetic scheme for a conductive oligomer covalently attached to a uridine nucleoside via an amide bond.

FIG. 2 depicts the synthetic scheme for covalently attaching a conductive oligomer covalently attached to a uridine nucleoside via an amine bond.

FIG. 3 depicts the synthetic scheme for a conductive oligomer covalently attached to a uridine nucleoside via the base.

FIG. 4 depicts the synthetic scheme for a conductive oligomer covalently attached to a nucleoside via a phosphate of the ribose-phosphate backbone. The conductive oligomer is a phenyl-acetylene Structure 5 oligomer, although other oligomers may be used, and terminates in an ethyl pyridine protecting group, as described herein, for attachment to gold electrodes.

FIG. 5 depicts the synthetic scheme for a conductive oligomer covalently attached to a nucleoside via a phosphate of the ribose-phosphate backbone, using an amide linkage and an ethylene linker, although other linkers may be used. The conductive oligomer is a phenyl-acetylene Structure 5 oligomer, although other oligomers may be used, and terminates in an ethyl pyridine protecting group, as described herein, for attachment to gold electrodes.

FIG. 6 depicts the synthetic scheme for a conductive polymer containing an aromatic group with a substitution group. The conductive oligomer is a phenyl-acetylene Structure 5 oligomer with a single methyl R group on each phenyl ring, although other oligomers may be used, and terminates in an ethyl pyridine protecting group, as described herein, for attachment to gold electrodes.

FIG. 7 depicts the synthetic scheme for the synthesis of a metallocene, in this case ferrocene, linked via a conductive oligomer to an electrode. The conductive oligomer is a phenyl-acetylene Structure 5 oligomer, although other oligomers may be used, and terminates in an ethyl pyridine protecting group, as described herein, for attachment to gold electrodes.

FIG. 8 depicts a model compound, ferrocene attached to a $C_{16}$ alkane molecule (insulator-1), at 200 mV AC amplitude and frequencies of 1, 5 and 100 Hz. The sample responds at all three frequencies, with higher currents resulting from higher frequencies.

FIGS. 9A and 9B depict the response with varying frequency. FIG. 9A shows overlaid voltammograms of an electrode coated with a ferrocene-conductive oligomer model complex (wire-2). Four excitation frequencies were applied, 10 Hz, 100 Hz, 1 kHz and 10 kHz, all at 25 mV overpotential. Again, current increases with frequency. FIG. 9B shows overlaid voltammograms of electrodes coated with either ssDNA or dsDNA. ssDNA was run at 1 Hz and 10 Hz at 100 mV overpotential (bottom two lines). dsDNA was run at 1, 10, 50 and 100 Hz at 10 mV overpotential (top four lines). Note that the scales between FIG. 8 and FIGS. 9A and 9B are different.

FIG. 10 depicts the frequency response of these systems. The peak currents at a number of frequencies are determined and plotted. Sample 3 (filled triangles) responds to increasing frequencies through 10 kHz (system limit), while samples 1 (open circles) and 2 (filled circles) lose their responses at between 20 and 200 Hz. This data was not normalized to the increase in current associated with increasing frequency.

FIG. 11 depicts the frequency responses of ssDNA (open circles; sample 5) and dsDNA (filled circles; sample 6) at 25 mV overpotential. The current has been normalized. The curves are not a fit to the data; rather, these are models of RC circuits, illustrating that the data can be fit to such curves, and that the system is in fact mimic standard RC circuits. The top curve was modeled using a 500 ohm resistor and a 0.001 farad capacitor. The bottom curve was modeled using a 20 ohm resistor and a 0.002 farad capacitor.

FIG. 12 shows that increasing the overpotential will increase the output current.

FIGS. 13A and 13B illustrate that the overpotential and frequency can be tuned to increase the selectivity and sensitivity, using Sample 1.

FIG. 14 shows that ferrocene added to the solution (Sample 7; open circles) has a frequency response related to diffusion that is easily distinguishable from attached ferrocene (Sample 3; filled circles).

FIGS. 15A and 15B shows the phase shift that results with different samples. FIG. 15A uses two experiments of Sample 1, Sample 3 and Sample 4. FIG. 15B uses Sample 5 and Sample 6.

FIG. 16 depicts the synthetic scheme for a conductive oligomer covalently attached to a uridine nucleoside via an amine bond, with a CH2 group as a Z linker. Compound C4 can be extended as outlined herein and in FIG. 1.

FIGS. 17A, 17B, 17C, 17D, 17E, 17F and 17G depict other conductive oligomers, attached either through the base (A-D) or through the ribose of the backbone (E-G), which have been synthesized using the techniques outlined herein. FIG. 17H depicts a conductive oligomer attached to a ferrocene. As will be appreciated by those in the art, the compounds are shown as containing CPG groups, phosphoramidite groups, or neither; however, they may all be made as any of these.

FIG. 21 depicts the use of a trimethylsilylethyl protecting group in synthesizing a five unit wire attached via the base.

FIGS. 22A and 22B depict simulations based on traditional electrochemical theory (FIG. 22B) and the simulation model developed herein (FIG. 22A).

FIGS. 23A and 23B depict experimental data plotted with theoretical model, showing good correlation. Fc-wire of Example 7 was used as 10 Hz (FIG. 23A) and 100 Hz (FIG. 23B).

DETAILED DESCRIPTION OF THE INVENTION

Figure 18B:
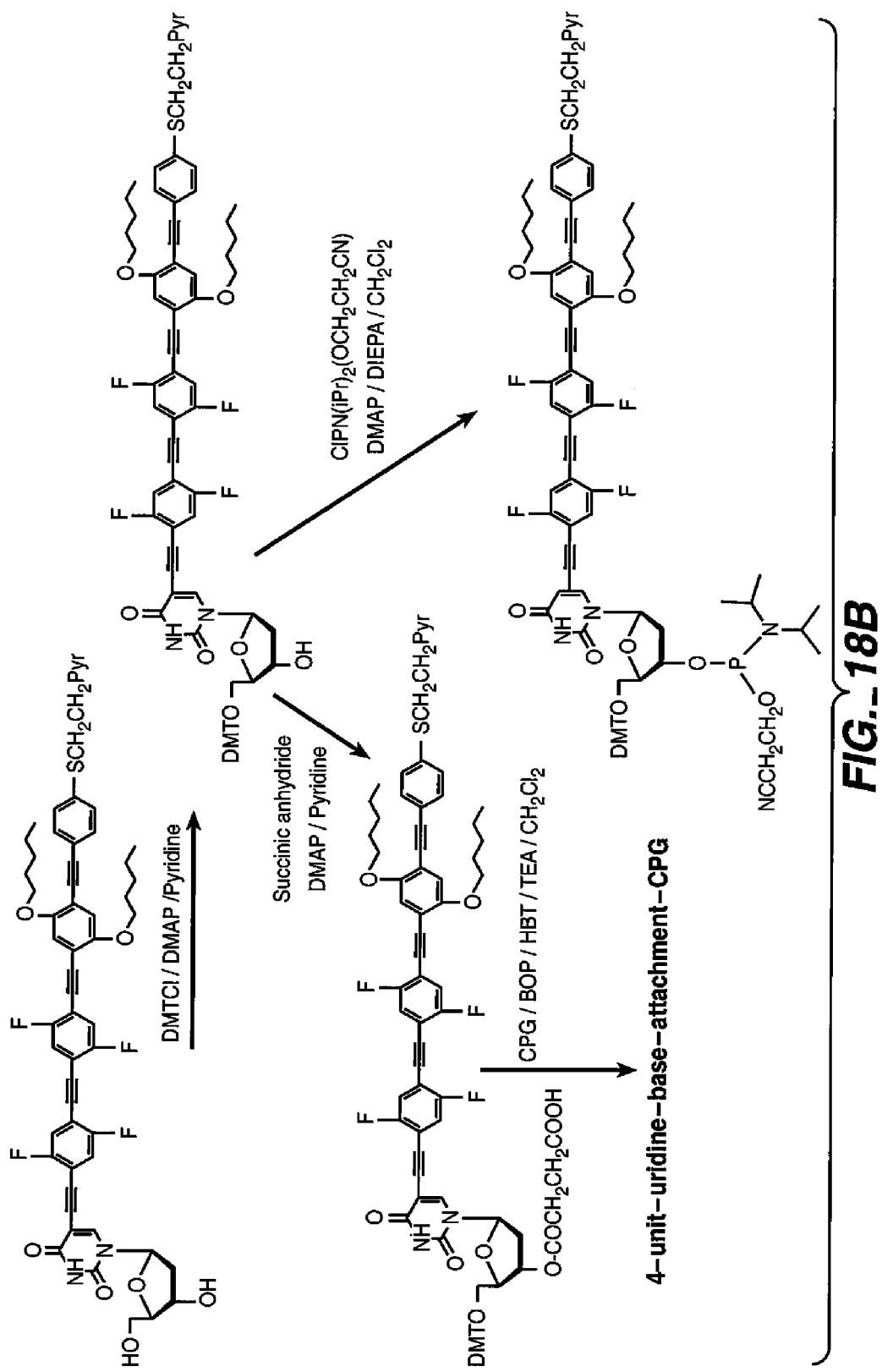
FIG. 18 depicts a synthetic scheme for a four unit conductive oligomer attached to the base.

The present invention capitalizes on the previous discovery that electron transfer apparently proceeds through the stacked π-orbitals of the heterocyclic bases of double stranded (hybridized) nucleic acid ("the π-way"). This finding allows the use of nucleic acids containing electron transfer moieties to be used as nucleic acid probes. See PCT publication WO 95/15971, hereby incorporated by reference in its entirety, and cited references. This publication describes the site-selective modification of nucleic acids with redox active moieties, i.e. electron donor and acceptor moieties, which allow the long-distance electron transfer through a double stranded nucleic acid. In general, electron transfer between electron donors and acceptors does not occur at an appreciable rate when the nucleic acid is single stranded, nor does it occur appreciably unless nucleotide base pairing exists in the double stranded sequence between the electron donor and acceptor in the double helical structure. Thus, PCT publication WO 95/15971 and the present invention are directed to the use of nucleic acids with electron transfer moieties, including electrodes, as probes for the detection of target sequences within a sample.

In one embodiment, the present invention provides for novel gene probes, which are useful in molecular biology and diagnostic medicine. In this embodiment, single stranded nucleic acids having a predetermined sequence and covalently attached electron transfer moieties, including an electrode, are synthesized. The sequence is selected based upon a known target sequence, such that if hybridization to a complementary target sequence occurs in the region between the electron donor and the electron acceptor, electron transfer proceeds at an appreciable and detectable rate. Thus, the invention has broad general use, as a new form of labelled gene probe. In addition, the probes of the present invention allow detection of target sequences without the removal of unhybridized probe. Thus, the invention is uniquely suited to automated gene probe assays or field testing.

The present invention provides improved compositions comprising nucleic acids covalently attached via conductive oligomers to an electrode, of a general structure depicted below in Structure 1:

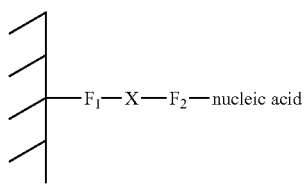

Structure 1

In Structure 1, the hatched marks on the left represent an electrode. X is a conductive oligomer as defined herein. $F_1$ is a linkage that allows the covalent attachment of the electrode and the conductive oligomer, including bonds, atoms or linkers such as is described herein, for example as "A", defined below. $F_2$ is a linkage that allows the covalent attachment of the conductive oligomer to the nucleic acid, and may be a bond, an atom or a linkage as is herein described. $F_2$ may be part of the conductive oligomer, part of the nucleic acid, or exogeneous to both, for example, as defined herein for "Z".

By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate, phosphorodithioate, O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35, hereby incorporated by reference. These modifications of the ribose-phosphate backbone may be done to facilitate the addition of electron transfer moieties, or to increase the stability and half-life of such molecules in physiological environments.

Particularly preferred are peptide nucleic acids (PNA). These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2-4° C. drop in Tm for an internal mismatch. With the non-ionic PNA backbone, the drop is closer to 7-9° C. This allows for better detection of mismatches. Similarly, due to their non-ionic nature, hybridization of the bases attached to these backbones is relatively insensitive to salt concentration. This is particularly advantageous in the systems of the present invention, as a reduced salt hybridization solution has a lower Faradaic current than a physiological salt solution (in the range of 150 mM).

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine and hypoxathanine, etc. As used herein, the term "nucleoside" includes nucleotides, and modified nucleosides such as amino modified nucleosides.

The nucleosides and nucleic acids are covalently attached to a conductive oligomer. By "conductive oligomer" herein is meant a substantially conducting oligomer, preferably linear, some embodiments of which are referred to in the literature as "molecular wires". By "substantially conducting" herein is meant that the rate of electron transfer through the conductive oligomer is faster than the rate of electron transfer through single stranded nucleic acid, such that the conductive oligomer is not the rate limiting step in the detection of hybridization, although as noted below, systems which use spacers that are the rate limiting step are also acceptable. Stated differently, the resistance of the conductive oligomer is less than that of the nucleic acid. Preferably, the rate of electron transfer through the conductive oligomer is faster than the rate of electron transfer through double stranded nucleic acid, i.e. through the stacked π-orbitals of the double helix. Generally, the conductive oligomer has substantially overlapping π-orbitals, i.e. conjugated π-orbitals, as between the monomeric units of the conductive oligomer, although the conductive oligomer may also contain one or more sigma (σ) bonds. Additionally, a conductive oligomer may be defined functionally by its ability to inject or receive electrons into or from an attached nucleic acid. Furthermore, the conductive oligomer is more conductive than the insulators as defined herein.

In a preferred embodiment, the conductive oligomers have a conductivity, S, of from between about $10^{-6}$ to about $10^4$ $\Omega^{-1}cm^{-1}$, with from about $10^{-5}$ to about $10^3$ $\Omega^{-1}cm^{-1}$ being preferred, with these S values being calculated for molecules ranging from about 20 Å to about 200 Å. As described below, insulators have a conductivity S of about $10^{-7}$ $\Omega^{-1}cm^{-1}$ or lower, with less than about $10^{-8}$ $\Omega^{-1}cm^{-1}$ being preferred. See generally Gardner et al., Sensors and Actuators A 51 (1995) 57-66, incorporated herein by reference.

Desired characteristics of a conductive oligomer include high conductivity, sufficient solubility in organic solvents and/or water for synthesis and use of the compositions of the invention, and preferably chemical resistance to reactions that occur i) during nucleic acid synthesis (such that nucleosides containing the conductive oligomers may be added to a nucleic acid synthesizer during the synthesis of the compositions of the invention), ii) during the attachment of the conductive oligomer to an electrode, or iii) during hybridization assays.

The oligomers of the invention comprise at least two monomeric subunits, as described herein. As is described more fully below, oligomers include homo- and hetero-oligomers, and include polymers.

In a preferred embodiment, the conductive oligomer has the structure depicted in Structure 2:

Structure 2

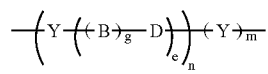

As will be understood by those in the art, all of the structures depicted herein may have additional atoms or structures; i.e. the conductive oligomer of Structure 2 may be attached to electron transfer moieties, such as electrodes, transition metal complexes, organic electron transfer moieties, and metallocenes, and to nucleic acids, or to several of these. Unless otherwise noted, the conductive oligomers depicted herein will be attached at the left side to an electrode; that is, as depicted in Structure 2, the left "Y" is connected to the electrode as described herein and the right "Y", if present, is attached to the nucleic acid, either directly or through the use of a linker, as is described herein.

In this embodiment, Y is an aromatic group, n is an integer from 1 to 50, g is either 1 or zero, e is an integer from zero to 10, and m is zero or 1. When g is 1, B—D is a conjugated bond, preferably selected from acetylene, alkene, substituted alkene, amide, azo, —C=N— (including —N=C—, —CR=N— and —N=CR—), —Si=Si—, and —Si=C— (including —C=Si—, —Si=CR— and —CR=Si—). When g is zero, e is preferably 1, D is preferably carbonyl, or a heteroatom moiety, wherein the heteroatom is selected from oxygen, sulfur, nitrogen or phosphorus. Thus, suitable heteroatom moieties include, but are not limited to, —NH and —NR, wherein R is as defined herein; substituted sulfur; sulfonyl (—SO$_2$—) sulfoxide (—SO—); phosphine oxide (—PO— and —RPO—); and thiophosphine (—PS— and —RPS—). However, when the conductive oligomer is to be attached to a gold electrode, as outlined below, sulfur derivatives are not preferred.

By "aromatic group" or grammatical equivalents herein is meant an aromatic monocyclic or polycyclic hydrocarbon moiety generally containing 5 to 14 carbon atoms (although larger polycyclic rings structures may be made) and any carbocylic ketone or thioketone derivative thereof, wherein the carbon atom with the free valence is a member of an aromatic ring. Aromatic groups include arylene groups and aromatic groups with more than two atoms removed. For the purposes of this application aromatic includes heterocycle. "Heterocycle" or "heteroaryl" means an aromatic group wherein 1 to 5 of the indicated carbon atoms are replaced by a heteroatom chosen from nitrogen, oxygen, sulfur, phosphorus, boron and silicon wherein the atom with the free valence is a member of an aromatic ring, and any heterocyclic ketone and thioketone derivative thereof. Thus, heterocycle includes thienyl, furyl, pyrrolyl, pyrimidinyl, oxalyl, indolyl, purinyl, quinolyl, isoquinolyl, thiazolyl, imidozyl, etc.

Importantly, the Y aromatic groups of the conductive oligomer may be different, i.e. the conductive oligomer may be a heterooligomer. That is, a conductive oligomer may comprise a oligomer of a single type of Y groups, or of multiple types of Y groups. Thus, in a preferred embodiment, when a barrier monolayer is used as is described below, one or more types of Y groups are used in the conductive oligomer within the monolayer with a second type(s) of Y group used above the monolayer level. Thus, as is described herein, the conductive oligomer may comprise Y groups that have good packing efficiency within the monolayer at the electrode surface, and a second type(s) of Y groups with greater flexibility and hydrophilicity above the monolayer level to facilitate nucleic acid hybridization. For example, unsubstituted benzyl rings may comprise the Y rings for monolayer packing, and substituted benzyl rings may be used above the monolayer. Alternatively, heterocylic rings, either substituted or unsubstituted, may be used above the monolayer. Additionally, in one embodiment, heterooligomers are used even when the conductive oligomer does not extend out of the monolayer.

The aromatic group may be substituted with a substitution group, generally depicted herein as R. R groups may be added as necessary to affect the packing of the conductive oligomers, i.e. when the nucleic acids attached to the conductive oligomers form a monolayer on the electrode, R groups may be used to alter the association of the oligomers in the monolayer. R groups may also be added to 1) alter the solubility of the oligomer or of compositions containing the oligomers; 2) alter the conjugation or electrochemical potential of the system; and 3) alter the charge or characteristics at the surface of the monolayer.

In a preferred embodiment, when the conductive oligomer is greater than three subunits, R groups are preferred to increase solubility when solution synthesis is done. However, the R groups, and their positions, are chosen to minimally effect the packing of the conductive oligomers on a surface, particularly within a monolayer, as described below. In general, only small R groups are used within the monolayer, with larger R groups generally above the surface of the monolayer. Thus for example the attachment of methyl groups to the portion of the conductive oligomer within the monolayer to increase solubility is preferred, with attachment of longer alkoxy groups, for example, C3 to C10, is preferably done above the monolayer surface. In general, for the systems described herein, this generally means that attachment of sterically significant R groups is not done on any of the first three oligomer subunits, depending on the length of the insulator molecules.

Suitable R groups include, but are not limited to, hydrogen, alkyl, alcohol, aromatic, amino, amido, nitro, ethers, esters, aldehydes, sulfonyl, silicon moieties, halogens, sulfur containing moieties, phosphorus containing moieties, and ethylene glycols. In the structures depicted herein, R is hydrogen when the position is unsubstituted. It should be noted that some positions may allow two substitution groups, R and R', in which case the R and R' groups may be either the same or different.

By "alkyl group" or grammatical equivalents herein is meant a straight or branched chain alkyl group, with straight chain alkyl groups being preferred. If branched, it may be branched at one or more positions, and unless specified, at any position. The alkyl group may range from about 1 to about 30 carbon atoms (C1-C30), with a preferred embodiment utilizing from about 1 to about 20 carbon atoms (C1-C20), with about C1 through about C12 to about C15 being preferred, and C1 to C5 being particularly preferred, although in some embodiments the alkyl group may be much larger. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, nitrogen, and silicone being preferred. Alkyl includes substituted alkyl groups. By "substituted alkyl group" herein is meant an alkyl group further comprising one or more substitution moieties "R", as defined above.

By "amino groups" or grammatical equivalents herein is meant —$NH_2$, —NHR and —$NR_2$ groups, with R being as defined herein.

By "nitro group" herein is meant an —$NO_2$ group.

By "sulfur containing moieties" herein is meant compounds containing sulfur atoms, including but not limited to, thia-, thio- and sulfo-compounds, thiols (—SH and —SR), and sulfides (—RSR—). By "phosphorus containing moieties" herein is meant compounds containing phosphorus, including, but not limited to, phosphines and phosphates. By "silicon containing moieties" herein is meant compounds containing silicon.

By "ether" herein is meant an —O—R group. Preferred ethers include alkoxy groups, with —O—$(CH_2)_2CH_3$ and —O—$(CH_2)_4CH_3$ being preferred.

By "ester" herein is meant a —COOR group.

By "halogen" herein is meant bromine, iodine, chlorine, or fluorine. Preferred substituted alkyls are partially or fully halogenated alkyls such as $CF_3$, etc.

By "aldehyde" herein is meant —RCOH groups.

By "alcohol" herein is meant —OH groups, and alkyl alcohols —ROH.

By "amido" herein is meant —RCONH— or RCONR— groups.

By "ethylene glycol" herein is meant a —(O—$CH_2$—$CH_2$)$_n$— group, although each carbon atom of the ethylene group may also be singly or doubly substituted, i.e. —(O—$CR_2$—$CR_2$)$_n$—, with R as described above. Ethylene glycol derivatives with other heteroatoms in place of oxygen (i.e. —(N—$CH_2$—$CH_2$)$_n$— or —(S—$CH_2$—$CH_2$)$_n$—, or with substitution groups) are also preferred.

Preferred substitution groups include, but are not limited to, methyl, ethyl, propyl, alkoxy groups such as —O—$(CH_2)_2$$CH_3$ and —O—$(CH_2)_4CH_3$ and ethylene glycol and derivatives thereof.

Preferred aromatic groups include, but are not limited to, phenyl, naphthyl, naphthalene, anthracene, phenanthroline, pyrole, pyridine, thiophene, porphyrins, and substituted derivatives of each of these, included fused ring derivatives.

In the conductive oligomers depicted herein, when g is 1, B—D is a bond linking two atoms or chemical moieties. In a preferred embodiment, B—D is a conjugated bond, containing overlapping or conjugated π-orbitals.

Preferred B—D bonds are selected from acetylene (—C≡C—, also called alkyne or ethyne), alkene (—CH=CH—, also called ethylene), substituted alkene (—CR=CR—, —CH=CR— and —CR=CH—), amide (—NH—CO— and —NR—CO— or —CO—NH— and —CO—NR—), azo (—N=N—), esters and thioesters (—CO—O—, —O—CO—, —CS—O— and —O—CS—) and other conjugated bonds such as (—CH=N—, —CR=N—, —N=CH— and —N=CR—), (—SiH=SiH—, —SiR=SiH—, —SiR=SiH—, and —SiR=SiR—), (—SiH=CH—, —SiR=CH—, —SiH=CR—, —SiR=CR—, —CH=SiH—, —CR=SiH—, —CH=SiR—, and —CR=SiR—). Particularly preferred B—D bonds are acetylene, alkene, amide, and substituted derivatives of these three, and azo. Especially preferred B—D bonds are acetylene, alkene and amide. The oligomer components attached to double bonds may be in the trans or cis conformation, or mixtures. Thus, either B or D may include carbon, nitrogen or silicon. The substitution groups are as defined as above for R.

When g=0 in the Structure 2 conductive oligomer, e is preferably 1 and the D moiety may be carbonyl or a heteroatom moiety as defined above.

As above for the Y rings, within any single conductive oligomer, the B—D bonds (or D moieties, when g=0) may be all the same, or at least one may be different. For example, when m is zero, the terminal B—D bond may be an amide bond, and the rest of the B—D bonds may be acetylene bonds. Generally, when amide bonds are present, as few amide bonds as possible are preferable, but in some embodiments all the B—D bonds are amide bonds. Thus, as outlined above for the Y rings, one type of B—D bond may be present in the conductive oligomer within a monolayer as described below, and another type above the monolayer level, to give greater flexibility for nucleic acid hybridization.

In the structures depicted herein, n is an integer from 1 to 50, although longer oligomers may also be used (see for example Schumm et al., Angew. Chem. Int. Ed. Engl. 1994 33(13):1360). Without being bound by theory, it appears that for efficient hybridization of nucleic acids on a surface, the hybridization should occur at a distance from the surface, i.e. the kinetics of hybridization increase as a function of the distance from the surface, particularly for long oligonucleotides of 200 to 300 basepairs. Accordingly, the length of the conductive oligomer is such that the closest nucleotide of the nucleic acid is positioned from about 6 Å to about 100 Å (although distances of up to 500 Å may be used) from the electrode surface, with from about 25 Å to about 60 Å being preferred. Accordingly, n will depend on the size of the aromatic group, but generally will be from about 1 to about 20, with from about 2 to about 15 being preferred and from about 3 to about 10 being especially preferred.

In the structures depicted herein, m is either 0 or 1. That is, when m is 0, the conductive oligomer may terminate in the B—D bond or D moiety, i.e. the D atom is attached to the nucleic acid either directly or via a linker. In some embodiments, for example when the conductive oligomer is attached to a phosphate of the ribose-phosphate backbone of a nucleic acid, there may be additional atoms, such as a linker, attached between the conductive oligomer and the nucleic acid. Additionally, as outlined below, the D atom may be the nitrogen atom of the amino-modified ribose. Alternatively, when m is 1, the conductive oligomer may terminate in Y, an aromatic group, i.e. the aromatic group is attached to the nucleic acid or linker.

As will be appreciated by those in the art, a large number of possible conductive oligomers may be utilized. These include conductive oligomers falling within the Structure 2 and Structure 9 formulas, as well as other conductive oligomers, as are generally known in the art, including for example, compounds comprising fused aromatic rings or Teflon®-like oligomers, such as —$(CF_2)_n$—, —$(CHF)_n$— and —$(CFR)_n$—. See for example, Schumm et al., angew. Chem. Intl. Ed. Engl. 33:1361 (1994); Grosshenny et al., Platinum Metals Rev. 40(1):26-35 (1996); Tour, Chem. Rev. 96:537-553 (1996); Hsung et al., Organometallics 14:4808-4815 (1995; and references cited therein, all of which are expressly incorporated by reference.

Particularly preferred conductive oligomers of this embodiment are depicted below:

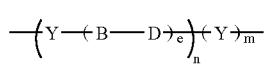

Structure 3

Structure 3 is Structure 2 when g is 1. Preferred embodiments of Structure 3 include: e is zero, Y is pyrole or substituted pyrole; e is zero, Y is thiophene or substituted thiophene; e is zero, Y is furan or substituted furan; e is zero, Y is phenyl or substituted phenyl; e is zero, Y is pyridine or substituted pyridine; e is 1, B—D is acetylene and Y is phenyl or substituted phenyl (see Structure 5 below). A preferred embodiment of Structure 3 is also when e is one, depicted as Structure 4 below:

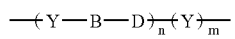

Structure 4

Preferred embodiments of Structure 4 are: Y is phenyl or substituted phenyl and B—D is azo; Y is phenyl or substituted phenyl and B—D is alkene; Y is pyridine or substituted pyridine and B—D is acetylene; Y is thiophene or substituted thiophene and B—D is acetylene; Y is furan or substituted furan and B—D is acetylene; Y is thiophene or furan (or substituted thiophene or furan) and B—D are alternating alkene and acetylene bonds.

Most of the structures depicted herein utilize a Structure 4 conductive oligomer. However, any Structure 4 oligomers may be substituted with a Structure 2, 3 or 9 oligomer, or other conducting oligomer, and the use of such Structure 4 depiction is not meant to limit the scope of the invention.

Particularly preferred embodiments of Structure 4 include Structures 5, 6, 7 and 8, depicted below:

Structure 5

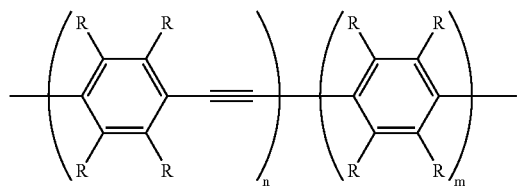

Particularly preferred embodiments of Structure 5 include: n is two, m is one, and R is hydrogen; n is three, m is zero, and R is hydrogen; and the use of R groups to increase solubility.

Structure 6

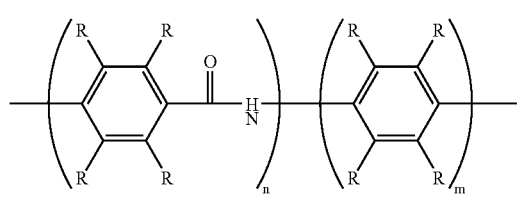

When the B—D bond is an amide bond, as in Structure 6, the conductive oligomers are pseudopeptide oligomers.

Although the amide bond in Structure 6 is depicted with the carbonyl to the left, i.e. —CONH—, the reverse may also be used, i.e. —NHCO—. Particularly preferred embodiments of Structure 6 include: n is two, m is one, and R is hydrogen; n is three, m is zero, and R is hydrogen (in this embodiment, the terminal nitrogen (the D atom) may be the nitrogen of the amino-modified ribose); and the use of R groups to increase solubility.

Structure 7

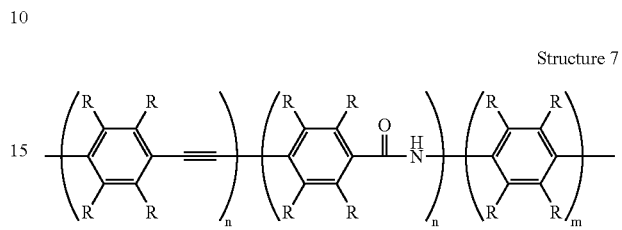

Preferred embodiments of Structure 7 include the first n is two, second n is one, m is zero, and all R groups are hydrogen, or the use of R groups to increase solubility.

Structure 8

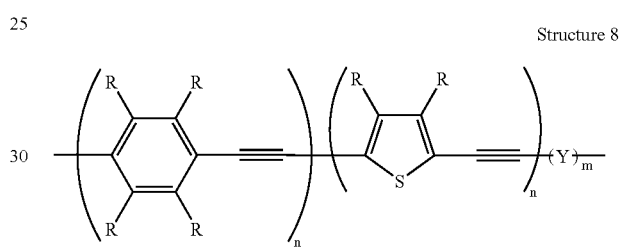

Preferred embodiments of Structure 8 include: the first n is three, the second n is from 1-3, with m being either 0 or 1, and the use of R groups to increase solubility.

In a preferred embodiment, the conductive oligomer has the structure depicted in Structure 9:

Structure 9

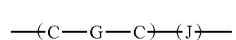

In this embodiment, C are carbon atoms, n is an integer from 1 to 50, m is 0 or 1, J is a heteroatom selected from the group consisting of nitrogen, silicon, phosphorus, sulfur, carbonyl or sulfoxide, and G is a bond selected from alkane, alkene or acetylene, such that together with the two carbon atoms the C-G-C group is an alkene (—CH=CH—), substituted alkene (—CR=CR—) or mixtures thereof (—CH=CR— or —CR=CH—), acetylene (—C≡C—), or alkane (—CR$_2$—CR$_2$—, with R being either hydrogen or a substitution group as described herein). The G bond of each subunit may be the same or different than the G bonds of other subunits; that is, alternating oligomers of alkene and acetylene bonds could be used, etc. However, when G is an alkane bond, the number of alkane bonds in the oligomer should be kept to a minimum, with about six or less sigma bonds per conductive oligomer being preferred. Alkene bonds are preferred, and are generally depicted herein, although alkane and acetylene bonds may be substituted in any structure or embodiment described herein as will be appreciated by those in the art.

In a preferred embodiment, the m of Structure 9 is zero. In a particularly preferred embodiment, m is zero and G is an alkene bond, as is depicted in Structure 10:

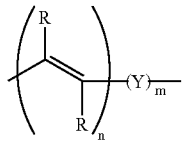

Structure 10

The alkene oligomer of structure 10, and others depicted herein, are generally depicted in the preferred trans configuration, although oligomers of cis or mixtures of trans and cis may also be used. As above, R groups may be added to alter the packing of the compositions on an electrode, the hydrophilicity or hydrophobicity of the oligomer, and the flexibility, i.e. the rotational, torsional or longitudinal flexibility of the oligomer. n is as defined above.

In a preferred embodiment, R is hydrogen, although R may be also alkyl groups and polyethylene glycols or derivatives.

In an alternative embodiment, the conductive oligomer may be a mixture of different types of oligomers, for example of structures 2 and 9.

The conductive oligomers are covalently attached to the nucleic acids. By "covalently attached" herein is meant that two moieties are attached by at least one bond, including sigma bonds, pi bonds and coordination bonds.

The nucleic acid is covalently attached to the conductive oligomer, and the conductive oligomer is also covalently attached to the electrode. In general, the covalent attachments are done in such a manner as to minimize the amount of unconjugated sigma bonds an electron must travel from the electron donor to the electron acceptor. Thus, linkers are generally short, or contain conjugated bonds with few sigma bonds.

The covalent attachment of the nucleic acid and the conductive oligomer may be accomplished in several ways. In a preferred embodiment, the attachment is via attachment to the base of the nucleoside, via attachment to the backbone of the nucleic acid (either the ribose, the phosphate, or to an analogous group of a nucleic acid analog backbone), or via a transition metal ligand, as described below. The techniques outlined below are generally described for naturally occuring nucleic acids, although as will be appreciated by those in the art, similar techniques may be used with nucleic acid analogs.

In a preferred embodiment, the conductive oligomer is attached to the base of a nucleoside of the nucleic acid. This may be done in several ways, depending on the oligomer, as is described below. In one embodiment, the oligomer is attached to a terminal nucleoside, i.e. either the 3' or 5' nucleoside of the nucleic acid. Alternatively, the conductive oligomer is attached to an internal nucleoside.

The point of attachment to the base will vary with the base. While attachment at any position is possible, it is preferred to attach at positions not involved in hydrogen bonding to the complementary base. Thus, for example, generally attachment is to the 5 or 6 position of pyrimidines such as uridine, cytosine and thymine. For purines such as adenine and guanine, the linkage is preferably via the 8 position. Attachment to non-standard bases is preferably done at the comparable positions.

In one embodiment, the attachment is direct; that is, there are no intervening atoms between the conductive oligomer and the base. In this embodiment, for example, conductive oligomers with terminal acetylene bonds are attached directly to the base. Structure 11 is an example of this linkage, using a Structure 4 conductive oligomer and uridine as the base, although other bases and conductive oligomers can be used as will be appreciated by those in the art:

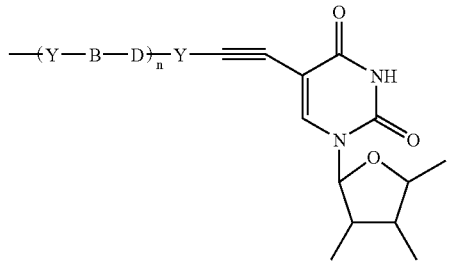

Structure 11

It should be noted that the pentose structures depicted herein may have hydrogen, hydroxy, phosphates or other groups such as amino groups attached. In addition, the pentose and nucleoside structures depicted herein are depicted non-conventionally, as mirror images of the normal rendering. In addition, the pentose and nucleoside structures may also contain additional groups, such as protecting groups, at any position, for example as needed during synthesis.

In addition, the base may contain additional modifications as needed, i.e. the carbonyl or amine groups may be altered or protected, for example as is depicted in FIG. 3 or 18.

In an alternative embodiment, the attachment is through an amide bond using a linker as needed, as is generally depicted in Structure 12 using uridine as the base and a Structure 4 oligomer:

Structure 12:

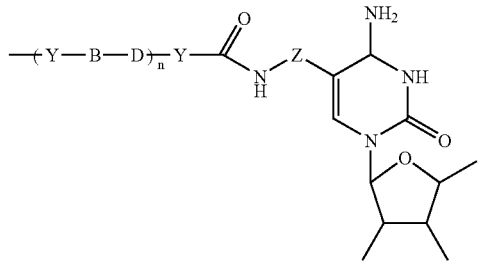

Preferred embodiments of Structure 12 include Z is a methylene or ethylene. The amide attachment can also be done using an amino group of the base, either a naturally occurring amino group such as in cytidine or adenidine, or from an amino-modified base as are known in the art.

In this embodiment, Z is a linker. Preferably, Z is a short linker of about 1 to about 5 atoms, that may or may not contain alkene bonds. Linkers are known in the art; for example, homo-or hetero-bifunctional linkers as are well known (see 1994 Pierce Chemical Company catalog, technical section on cross-linkers, pages 155-200, incorporated herein by reference). Preferred Z linkers include, but are not limited to, alkyl groups and alkyl groups containing heteroatom moieties, with short alkyl groups, esters, epoxy groups and ethylene glycol and derivatives being preferred, with propyl, acetylene, and $C_2$ alkene being especially preferred. Z may also be a sulfone group, forming sulfonamide linkages as discussed below.

In a preferred embodiment, the attachment of the nucleic acid and the conductive oligomer is done via attachment to the backbone of the nucleic acid. This may be done in a number of ways, including attachment to a ribose of the ribose-phosphate backbone, or to the phosphate of the backbone, or other groups of analogous backbones.

As a preliminary matter, it should be understood that the site of attachment in this embodiment may be to a 3' or 5' terminal nucleotide, or to an internal nucleotide, as is more fully described below.

In a preferred embodiment, the conductive oligomer is attached to the ribose of the ribose-phosphate backbone. This may be done in several ways. As is known in the art, nucleosides that are modified at either the 2' or 3' position of the ribose with amino groups, sulfur groups, silicone groups, phosphorus groups, or oxo groups can be made (Imazawa et al., J. Org. Chem., 44:2039 (1979); Hobbs et al., J. Org. Chem. 42(4):714 (1977); Verheyden et al., J. Orrg. Chem. 36(2):250 (1971); McGee et al., J. Org. Chem. 61:781-785 (1996); Mikhailopulo et al., Liebigs. Ann. Chem. 513-519 (1993); McGee et al., Nucleosides & Nucleotides 14(6):1329 (1995), all of which are incorporated by reference). These modified nucleosides are then used to add the conductive oligomers.

A preferred embodiment utilizes amino-modified nucleosides. These amino-modified riboses can then be used to form either amide or amine linkages to the conductive oligomers. In a preferred embodiment, the amino group is attached directly to the ribose, although as will be appreciated by those in the art, short linkers such as those described herein for "Z" may be present between the amino group and the ribose.

In a preferred embodiment, an amide linkage is used for attachment to the ribose. Preferably, if the conductive oligomer of Structures 2-4 is used, m is zero and thus the conductive oligomer terminates in the amide bond. In this embodiment, the nitrogen of the amino group of the amino-modified ribose is the "D" atom of the conductive oligomer. Thus, a preferred attachment of this embodiment is depicted in Structure 13 (using the Structure 4 conductive oligomer):

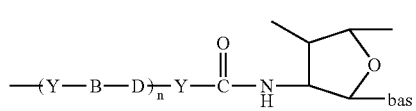

Structure 13

As will be appreciated by those in the art, Structure 13 has the terminal bond fixed as an amide bond.

In a preferred embodiment, a heteroatom linkage is used, i.e. oxo, amine, sulfur, etc. A preferred embodiment utilizes an amine linkage. Again, as outlined above for the amide linkages, for amine linkages, the nitrogen of the amino-modified ribose may be the "D" atom of the conductive oligomer when the Structure 4 conductive oligomer is used. Thus, for example, Structures 14 and 15 depict nucleosides with the Structures 4 and 10 conductive oligomers, respectively, using the nitrogen as the heteroatom, although other heteroatoms can be used:

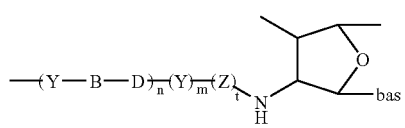

Structure 14

In Structure 14, preferably both m and t are not zero. A preferred Z here is a methylene group, or other aliphatic alkyl linkers. One, two or three carbons in this position are particularly useful for synthetic reasons; see FIG. 16.

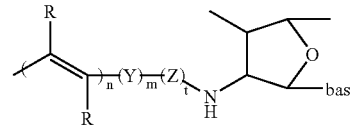

Structure 15

In Structure 15, Z is as defined above. Suitable linkers include methylene and ethylene.

In an alternative embodiment, the conductive oligomer is covalently attached to the nucleic acid via the phosphate of the ribose-phosphate backbone (or analog) of a nucleic acid. In this embodiment, the attachment is direct, utilizes a linker or via an amide bond. Structure 16 depicts a direct linkage, and Structure 17 depicts linkage via an amide bond (both utilize the Structure 4 conductive oligomer, although Structure 9 conductive oligomers are also possible). Structures 16 and 17 depict the conductive oligomer in the 3' position, although the 5' position is also possible. Furthermore, both Structures 16 and 17 depict naturally occurring phosphodiester bonds, although as those in the art will appreciate, non-standard analogs of phosphodiester bonds may also be used.

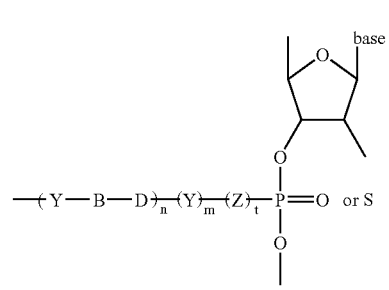

Structure 16

In Structure 16, if the terminal Y is present (i.e. m=1), then preferably Z is not present (i.e. t=0). If the terminal Y is not present, then Z is preferably present.

Structure 17 depicts a preferred embodiment, wherein the terminal B—D bond is an amide bond, the terminal Y is not present, and Z is a linker, as defined herein.

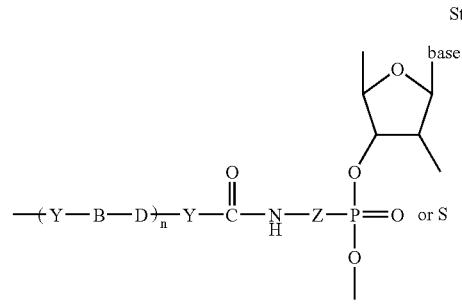

Structure 17

In a preferred embodiment, the conductive oligomer is covalently attached to the nucleic acid via a transition metal ligand. In this embodiment, the conductive oligomer is covalently attached to a ligand which provides one or more of the coordination atoms for a transition metal. In one embodiment, the ligand to which the conductive oligomer is attached also has the nucleic acid attached, as is generally depicted below in Structure 18. Alternatively, the conductive oligomer is attached to one ligand, and the nucleic acid is attached to another ligand, as is generally depicted below in Structure 19. Thus, in the presence of the transition metal, the conductive oligomer is covalently attached to the nucleic acid. Both of these structures depict Structure 4 conductive oligomers, although other oligomers may be utilized. Structures 18 and 19 depict two representative structures:

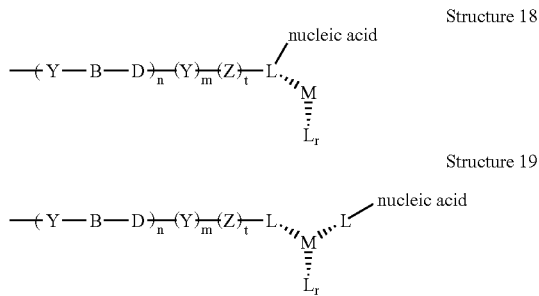

Structure 18

Structure 19

In the structures depicted herein, M is a metal atom, with transition metals being preferred. Suitable transition metals for use in the invention include, but are not limited to, cadmium (Cd), copper (Cu), cobalt (Co), palladium (Pd), zinc (Zn), iron (Fe), ruthenium (Ru), rhodium (Rh), osmium (Os), rhenium (Re), platinum (Pt), scandium (Sc), titanium (Ti), Vanadium (V), chromium (Cr), manganese (Mn), nickel (Ni), Molybdenum (Mo), technetium (Tc), tungsten (W), and iridium (Ir). That is, the first series of transition metals, the platinum metals (Ru, Rh, Pd, Os, Ir and Pt), along with Fe, Re, W, Mo and Tc, are preferred. Particularly preferred are ruthenium, rhenium, osmium, platinum, cobalt and iron.

L are the co-ligands, that provide the coordination atoms for the binding of the metal ion. As will be appreciated by those in the art, the number and nature of the co-ligands will depend on the coordination number of the metal ion. Mono-, di- or polydentate co-ligands may be used at any position. Thus, for example, when the metal has a coordination number of six, the L from the terminus of the conductive oligomer, the L contributed from the nucleic acid, and r, add up to six. Thus, when the metal has a coordination number of six, r may range from zero (when all coordination atoms are provided by the other two ligands) to four, when all the co-ligands are monodentate. Thus generally, r will be from 0 to 8, depending on the coordination number of the metal ion and the choice of the other ligands.

In one embodiment, the metal ion has a coordination number of six and both the ligand attached to the conductive oligomer and the ligand attached to the nucleic acid are at least bidentate; that is, r is preferably zero, one (i.e. the remaining co-ligand is bidentate) or two (two monodentate co-ligands are used).

As will be appreciated in the art, the co-ligands can be the same or different. Suitable ligands fall into two categories: ligands which use nitrogen, oxygen, sulfur, carbon or phosphorus atoms (depending on the metal ion) as the coordination atoms (generally referred to in the literature as sigma ($\sigma$) donors) and organomatallic ligands such as metallocene ligands (generally referred to in the literature as pi ($\pi$) donors, and depicted herein as $L_m$) Suitable nitrogen donating ligands are well known in the art and include, but are not limited to, $NH_2$; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2',3'-c]phenazine (abbreviated dppz); dipyridophenazine; 1,4,5,8,9,12-hexaazatriphenylene (abbreviated hat); 9,10-phenanethrene-quinone diimine (abbreviated phi); 1,4,5,8-tetraazaphenanthrene (abbreviated tap); 1,4,8,11-tetra-azacyclotetradecane (abbreviated cyclam) and isocyanide. Substituted derivatives, including fused derivatives, may also be used. In some embodiments, porphyrins and substituted derivatives of the porphyrin family may be used. See for example, Comprehensive Coordination Chemistry, Ed. Wilkinson et al., Pergammon Press, 1987, Chapters 13.2 (pp 73-98), 21.1 (pp. 813-898) and 21.3 (pp 915-957), all of which are hereby expressly incorporated by reference.

Suitable sigma donating ligands using carbon, oxygen, sulfur and phosphorus are known in the art. For example, suitable sigma carbon donors are found in Cotton and Wilkenson, Advanced Organic Chemistry, 5th Edition, John Wiley & Sons, 1988, hereby incorporated by reference; see page 38, for example. Similarly, suitable oxygen ligands include crown ethers, water and others known in the art. Phosphines and substituted phosphines are also suitable; see page 38 of Cotton and Wilkenson.

The oxygen, sulfur, phosphorus and nitrogen-donating ligands are attached in such a manner as to allow the heteroatoms to serve as coordination atoms.

In a preferred embodiment, organometallic ligands are used. In addition to purely organic compounds for use as redox moieties, and various transition metal coordination complexes with $\delta$-bonded organic ligand with donor atoms as heterocyclic or exocyclic substituents, there is available a wide variety of transition metal organometallic compounds with $\pi$-bonded organic ligands (see Advanced Inorganic Chemistry, 5th Ed., Cotton & Wilkinson, John Wiley & Sons, 1988, chapter 26; Organometallics, A Concise Introduction, Elschenbroich et al., 2nd Ed., 1992, VCH; and Comprehensive Organometallic Chemistry II, A Review of the Literature 1982-1994, Abel et al. Ed., Vol. 7, chapters 7, 8, 10 & 11, Pergamon Press, hereby expressly incorporated by reference). Such organometallic ligands include cyclic aromatic compounds such as the cyclopentadienide ion [$C_5H_5(-1)$] and various ring substituted and ring fused derivatives, such as the indenylide (−1) ion, that yield a class of bis(cyclopentadieyl)metal compounds, (i.e. the metallocenes); see for example Robins et al., J. Am. Chem. Soc. 104:1882-1893 (1982); and Gassman et al., J. Am. Chem. Soc. 108:4228-4229 (1986), incorporated by reference. Of these, ferrocene [$(C_5H_5)_2Fe$] and its derivatives are prototypical examples which have been used in a wide variety of chemical (Connelly et al., Chem. Rev. 96:877-910 (1996), incorporated by reference) and electrochemical (Geiger et al., Advances in Organometallic Chemistry 23:1-93; and Geiger et al., Advances in Organometallic Chemistry 24:87, incorporated by reference) electron transfer or "redox" reactions. Metallocene derivatives of a variety of the first, second and third row transition metals are potential candidates as redox moieties that are covalently attached to either the ribose ring or the nucleoside base of nucleic acid. Other potentially suitable organometallic ligands include cyclic arenes such as benzene, to yield bis(arene)metal compounds and their ring substituted and ring fused derivatives, of which bis(benzene)chromium is a prototypical example, Other acyclic $\pi$-bonded ligands such as the allyl(−1) ion, or butadiene yield potentially suitable organometallic compounds, and all such ligands, in conjuction with other $\pi$-bonded and $\delta$-bonded ligands constitute the general class of organometallic compounds in which there is a metal to carbon bond. Electrochemical studies of various dimers and oligomers of such compounds with bridging organic ligands, and additional non-bridging ligands, as well as with and without metal-metal bonds are potential candidate redox moieties in nucleic acid analysis.

When one or more of the co-ligands is an organometallic ligand, the ligand is generally attached via one of the carbon atoms of the organometallic ligand, although attachment may be via other atoms for heterocyclic ligands. Preferred organometallic ligands include metallocene ligands, including substituted derivatives and the metalloceneophanes (see page 1174 of Cotton and Wilkenson, supra). For example, derivatives of metallocene ligands such as methylcyclopentadienyl, with multiple methyl groups being preferred, such as pentamethylcyclopentadienyl, can be used to increase the stability of the metallocene. In a preferred embodiment, only one of the two metallocene ligands of a metallocene are derivatized.

As described herein, any combination of ligands may be used. Preferred combinations include: a) all ligands are nitrogen donating ligands; b) all ligands are organometallic ligands; and c) the ligand at the terminus of the conductive oligomer is a metallocene ligand and the ligand provided by the nucleic acid is a nitrogen donating ligand, with the other ligands, if needed, are either nitrogen donating ligands or metallocene ligands, or a mixture. These combinations are depicted in representative structures using the conductive oligomer of Structure 4 are depicted in Structures 20 (using phenanthroline and amino as representative ligands), 21 (using ferrocene as the metal-ligand combination) and 22 (using cyclopentadienyl and amino as representative ligands).

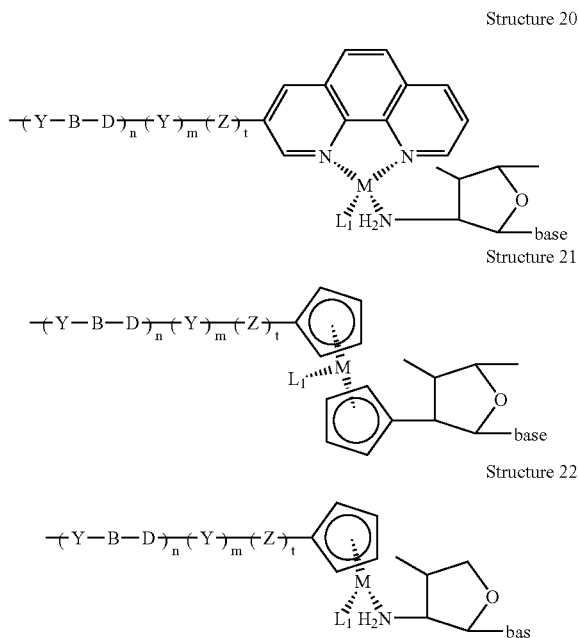

In a preferred embodiment, the ligands used in the invention show altered fluorescent properties depending on the redox state of the chelated metal ion. As described below, this thus serves as an additional mode of detection of electron transfer through nucleic acid.

In a preferred embodiment, as is described more fully below, the ligand attached to the nucleic acid is an amino group attached to the 2' or 3' position of a ribose of the ribose-phosphate backbone. This ligand may contain a multiplicity of amino groups so as to form a polydentate ligand which binds the metal ion. Other preferred ligands include cyclopentadiene and phenanthroline.

As described herein, the compositions described herein of nucleosides covalently attached to conductive oligomers may be incorporated into a longer nucleic acid at any number of positions, including either the 5' or 3' terminus of the nucleic acid or any internal position. As is outlined below, this is generally done by adding a nucleotide with a covalently attached conductive oligomer to an oligonucleotide synthetic reaction at any position. After synthesis is complete, the nucleic acid with the covalently attached conductive oligomer is attached to an electrode. Thus, any number of additional nucleotides, modified or not, may be included at any position. Alternatively, the compositions are made via post-nucleic acid synthesis modifications.

The total length of the nucleic acid will depend on its use. Generally, the nucleic acid compositions of the invention are useful as oligonucleotide probes. As is appreciated by those in the art, the length of the probe will vary with the length of the target sequence and the hybridization and wash conditions. Generally, oligonucleotide probes range from about 8 to about 50 nucleotides, with from about 10 to about 30 being preferred and from about 12 to about 25 being especially preferred. In some cases, very long probes may be used, e.g. 50 to 200-300 nucleotides in length.

Also of consideration is the distance between the nucleoside containing the electrode, i.e. a first electron transfer moiety, and the nucleoside containing a second electron transfer moiety. Electron transfer proceeds between the two electron transfer moieties. Since the rate of electron transfer is distance dependent, the distance between the two electron transfer moieties preferably ranges from about 1 to about 30 basepairs, with from about 2 to about 20 basepairs being preferred and from about 2 to about 10 basepairs being particularly preferred and from about 2 to 6 being especially preferred. However, probe specificity can be increased by adding oligonucleotides on either side of the electron transfer moieties, thus increasing probe specificity without increasing the distance an electron must travel.

Thus, in the structures depicted herein, nucleosides may be replaced with nucleic acids.

In a preferred embodiment, the conductive oligomers with covalently attached nucleosides or nucleic acids as depicted herein are covalently attached to an electrode. Thus, one end or terminus of the conductive oligomer is attached to the nucleoside or nucleic acid, and the other is attached to an electrode. In some embodiments it may be desirable to have the conductive oligomer attached at a position other than a terminus, or even to have a branched conductive oligomer that is attached to an electrode at one terminus and to two or more nucleosides at other termini, although this is not preferred. Similarly, the conductive oligomer may be attached at two sites to the electrode.

By "electrode" herein is meant a composition, which, when connected to an electronic device, is able to sense a current or charge and convert it to a signal. Thus, an electrode is an electron transfer moiety as described herein. Preferred electrodes are known in the art and include, but are not limited to, certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide ($Mo_2O_6$), tungsten oxide ($WO_3$) and ruthenium oxides; and carbon (including glassy carbon electrodes, graphite and carbon paste). Preferred electrodes include gold, silicon, carbon and metal oxide electrodes.

The electrodes described herein are depicted as a flat surface, which is only one of the possible conformations of the electrode and is for schematic purposes only. The conformation of the electrode will vary with the detection method used. For example, flat planar electrodes may be preferred for optical detection methods, or when arrays of nucleic acids are made, thus requiring addressable locations for both synthesis and detection. Alternatively, for single probe analysis, the electrode may be in the form of a tube, with the conductive oligomers and nucleic acids bound to the inner surface. This allows a maximum of surface area containing the nucleic acids to be exposed to a small volume of sample.

The covalent attachment of the conductive oligomer containing the nucleoside may be accomplished in a variety of ways, depending on the electrode and the conductive oligomer used. Generally, some type of linker is used, as depicted below as "A" in Structure 23, where X is the conductive oligomer, and the hatched surface is the electrode:

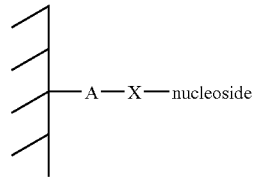

Structure 23

In this embodiment, A is a linker or atom. The choice of "A" will depend in part on the characteristics of the electrode. Thus, for example, A may be a sulfur moiety when a gold electrode is used. Alternatively, when metal oxide electrodes are used, A may be a silicon (silane) moiety attached to the oxygen of the oxide (see for example Chen et al., Langmuir 10:3332-3337 (1994); Lenhard et al., J. Electroanal. Chem. 78:195-201 (1977), both of which are expressly incorporated by reference). When carbon based electrodes are used, A may be an amino moiety (preferably a primary amine; see for example Deinhammer et al., Langmuir 10:1306-1313 (1994)). Thus, preferred A moieties include, but are not limited to, silane moieties, sulfur moieties (including alkyl sulfur moieties), and amino moieties. In a preferred embodiment, epoxide type linkages with redox polymers such as are known in the art are not used.

Although depicted herein as a single moiety, the conductive oligomer may be attached to the electrode with more than one "A" moiety; the "A" moieties may be the same or different. Thus, for example, when the electrode is a gold electrode, and "A" is a sulfur atom or moiety, such as generally depicted below in Structure 27, multiple sulfur atoms may be used to attach the conductive oligomer to the electrode, such as is generally depicted below in Structures 24, 25 and 26. As will be appreciated by those in the art, other such structures can be made. In Structures 24, 25 and 26, the A moiety is just a sulfur atom, but substituted sulfur moieties may also be used.

Structure 24

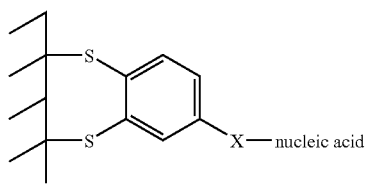

Structure 25

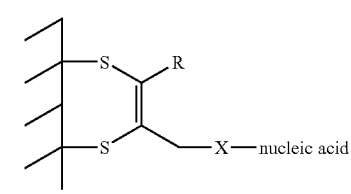

Structure 26

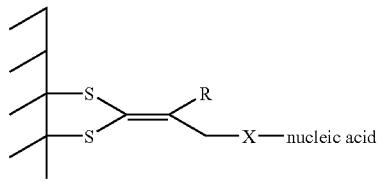

It should also be noted that similar to Structure 26, it may be possible to have a conductive oligomer terminating in a single carbon atom with three sulfur moieties attached to the electrode.

In a preferred embodiment, the electrode is a gold electrode, and attachment is via a sulfur linkage as is well known in the art, i.e. the A moiety is a sulfur atom or moiety. Although the exact characteristics of the gold-sulfur attachment are not known, this linkage is considered covalent for the purposes of this invention. A representative structure is depicted in Structure 27. Structure 27 depicts the "A" linker as comprising just a sulfur atom, although additional atoms may be present (i.e. linkers from the sulfur to the conductive oligomer or substitution groups).

Structure 27

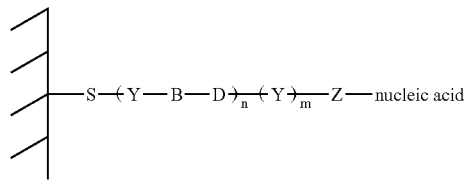

In a preferred embodiment, the electrode is a carbon electrode, i.e. a glassy carbon electrode, and attachment is via a nitrogen of an amine group. A representative structure is depicted in Structure 28. Again, additional atoms may be present, i.e. Z type linkers.

Structure 28

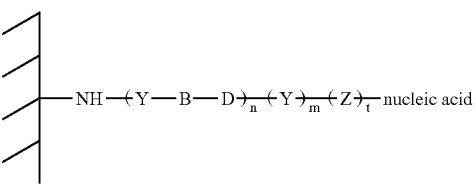

Structure 29

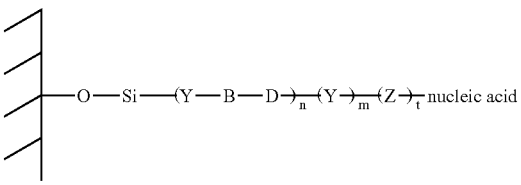

In Structure 29, the oxygen atom is from the oxide of the metal oxide electrode. The Si atom may also contain other atoms, i.e. be a silicon moiety containing substitution groups.

Thus, in a preferred embodiment, electrodes are made that comprise conductive oligomers attached to nucleic acids for the purposes of hybridization assays, as is more fully described herein. As will be appreciated by those in the art, electrodes can be made that have a single species of nucleic acid, i.e. a single nucleic acid sequence, or multiple nucleic acid species.

In addition, as outlined herein, the use of a solid support such as an electrode enables the use of these gene probes in an array form. The use of oligonucleotide arrays are well known in the art. In addition, techniques are known for "addressing" locations within an electrode and for the surface modification of electrodes. Thus, in a preferred embodiment, arrays of different nucleic acids are laid down on the electrode, each of which are covalently attached to the electrode via a conductive linker. In this embodiment, the number of different probe species of oligonucleotides may vary widely, from one to thousands, with from about 4 to about 100,000 being preferred, and from about 10 to about 10,000 being particularly preferred.

In a preferred embodiment, the electrode further comprises a passayation agent, preferably in the form of a monolayer on the electrode surface. As outlined above, the efficiency of oligonucleotide hybridization may increase when the oligonucleotide is at a distance from the electrode. A passayation agent layer facilitates the maintenance of the nucleic acid away from the electrode surface. In addition, a passayation agent serves to keep charge carriers away from the surface of the electrode. Thus, this layer helps to prevent electrical contact between the electrodes and the electron transfer moieties, or between the electrode and charged species within the solvent. Such contact can result in a direct "short circuit" or an indirect short circuit via charged species which may be present in the sample. Accordingly, the monolayer of passayation agents is preferably tightly packed in a uniform layer on the electrode surface, such that a minimum of "holes" exist. Alternatively, the passayation agent may not be in the form of a monolayer, but may be present to help the packing of the conductive oligomers or other characteristics.

The passayation agents thus serve as a physical barrier to block solvent accessibility to the electrode. As such, the passayation agents themselves may in fact be either (1) conducting or (2) nonconducting, i.e. insulating, molecules. Thus, in one embodiment, the passayation agents are conductive oligomers, as described herein, with or without a terminal group to block or decrease the transfer of charge to the electrode. Other passayation agents which may be conductive include oligomers of $-(CF_2)_n-$, $-(CHF)_n-$ and $-(CFR)_n-$. In a preferred embodiment, the passayation agents are insulator moieties.

An "insulator" is a substantially nonconducting oligomer, preferably linear. By "substantially nonconducting" herein is meant that the rate of electron transfer through the insulator is slower than the rate of electron transfer through the stacked π-orbitals of double stranded nucleic acid. Stated differently, the electrical resistance of the insulator is higher than the electrical resistance of the nucleic acid. In a preferred embodiment, the rate of electron transfer through the insulator is slower than or comparable to the rate through single stranded nucleic acid. Similarly, the rate of electron transfer through the insulator is preferrably slower than the rate through the conductive oligomers described herein. It should be noted however, as outlined in the Examples, that even oligomers generally considered to be insulators, such as $-(CH_2)_{16}$ molecules, still may transfer electrons, albeit at a slow rate.

In a preferred embodiment, the insulators have a conductivity, S, of about $10^{-7}\,\Omega^{-1}\mathrm{cm}^{-1}$ or lower, with less than about $10^{-8}\,\Omega^{-1}\,\mathrm{cm}^{-1}$ being preferred. See generally Gardner et al., supra.

Generally, insulators are alkyl or heteroalkyl oligomers or moieties with sigma bonds, although any particular insulator molecule may contain aromatic groups or one or more conjugated bonds. By "heteroalkyl" herein is meant an alkyl group that has at least one heteroatom, i.e. nitrogen, oxygen, sulfur, phosphorus, silicon or boron included in the chain. Alternatively, the insulator may be quite similar to a conductive oligomer with the addition of one or more heteroatoms or bonds that serve to inhibit or slow, preferably substantially, electron transfer.

The passayation agents, including insulators, may be substituted with R groups as defined herein to alter the packing of the moieties or conductive oligomers on an electrode, the hydrophilicity or hydrophobicity of the insulator, and the flexibility, i.e. the rotational, torsional or longitudinal flexibility of the insulator. For example, branched alkyl groups may be used. In addition, the terminus of the passayation agent, including insulators, may contain an additional group to influence the exposed surface of the monolayer. For example, there may be negatively charged groups on the terminus to form a negatively charged surface such that when the nucleic acid is DNA or RNA the nucleic acid is repelled or prevented from lying down on the surface, to facilitate hybridization. Preferred passayation agent terminal groups include $-NH_2$, $-OH$, $-COOH$, and $-CH_3$.

The length of the passayation agent will vary as needed. As outlined above, it appears that hybridization is more efficient at a distance from the surface. Thus, the length of the passayation agents is similar to the length of the conductive oligomers, as outlined above. In addition, the conductive oligomers may be basically the same length as the passayation agents or longer than them, resulting in the nucleic acids being more accessible to the solvent for hybridization.

The monolayer may comprise a single type of passayation agent, including insulators, or different types.

Suitable insulators are known in the art, and include, but are not limited to, $-(CH_2)_n-$, $-(CRH)_n-$, and $-(CR_2)_n-$, ethylene glycol or derivatives using other heteroatoms in place of oxygen, i.e. nitrogen or sulfur (sulfur derivatives are not preferred when the electrode is gold).

The passayation agents are generally attached to the electrode in the same manner as the conductive oligomer, and may use the same "A" linker as defined above.

In a preferred embodiment, the compositions of the present invention comprise a conductive oligomer, covalently attached to both an electrode, which serves as a first electron transfer moiety, and a nucleic acid. In this embodiment, the conductive oligomer preferably has the structure depicted in Structures 2, 3, 4, 9 or 10. In this embodiment, the compositions find use in general array-type technologies, i.e. the electrode may serve just as a solid support, with detection proceeding using techniques well known in the art, such as fluorescence or radioisotope labelling.

In this embodiment, it is possible to have each nucleic acid be the same, as an "anchor sequence", such that a second sequence can be added which contains the probe sequence and a sequence complementary to the anchor sequence. In this way, standard arrays of different anchor sequences can be made, which then can be used to generate custom arrays using novel probe sequences linked to complementary anchor regions.

Similarly, it is possible to have compositions comprising electrodes with conductive oligomers attached to probe nucleic acids, without second electron transfer moieties, and soluble second probe sequences with second electron transfer moieties. Upon binding of the target sequence, which contains a first target domain for the first probe sequence and a second target domain for the second probe sequence, which preferably are adjacent, electron transfer may occur.

Alternatively, it may be the target sequence which contains the second electron transfer moiety. Similar to methods which rely on amplification and labelling of target sequences, the target nucleic acid may be labelled with a second electron transfer moiety which then can be used to effect electron transfer upon formation of the hybridization complex.

In a preferred embodiment, the compositions of the present invention comprise a conductive oligomer, covalently attached to both an electrode, which serves as a first electron transfer moiety, and a nucleic acid, which has at least a second covalently attached electron transfer moiety. As noted herein, the conductive oligomer and the second electron transfer moiety may be attached at any position of the nucleic acid.

In one embodiment, a nucleic acid is modified with more than two electron transfer moieties. For example, to increase the signal obtained from the probe, or alter the required detector sensitivity, a plurality of electron transfer moieties may be used. See PCT publication WO 95/15971. For example, the conductive oligomer may be attached to an internal nucleoside, with second electron transfer moieties (ETM) attached both 5' and 3' to the nucleoside containing the conductive oligomer, as is generally depicted in Structure 29A. In one embodiment, the two additional electron transfer moieties are the same, and are placed the same distance away from the conductive oligomer, to result in a uniform signal. Alternatively, the additional electron transfer moieties may be different and/or placed at different distances from the conductive oligomer.

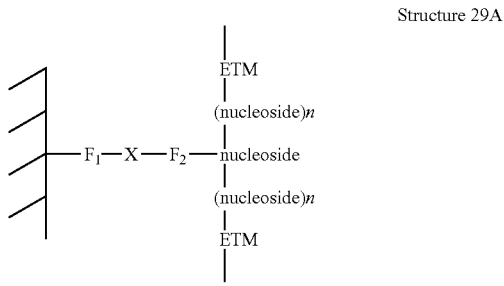

Structure 29A

The terms "electron donor moiety", "electron acceptor moiety", and "electron transfer moieties" or grammatical equivalents herein refers to molecules capable of electron transfer under certain conditions. It is to be understood that electron donor and acceptor capabilities are relative; that is, a molecule which can lose an electron under certain experimental conditions will be able to accept an electron under different experimental conditions. It is to be understood that the number of possible electron donor moieties and electron acceptor moieties is very large, and that one skilled in the art of electron transfer compounds will be able to utilize a number of compounds in the present invention. Preferred electron transfer moieties include, but are not limited to, transition metal complexes, organic electron transfer moieties, and electrodes.

In a preferred embodiment, the electron transfer moieties are transition metal complexes. Transition metals are those whose atoms have a partial or completed shell of electrons. Suitable transition metals for use in the invention are listed above.

The transition metals are complexed with a variety of ligands, L, defined above, to form suitable transition metal complexes, as is well known in the art.

In addition to transition metal complexes, other organic electron donors and acceptors may be covalently attached to the nucleic acid for use in the invention. These organic molecules include, but are not limited to, riboflavin, xanthene dyes, azine dyes, acridine orange, N,N'-dimethyl-2,7-diazapyrenium dichloride ($DAP^{2+}$), methylviologen, ethidium bromide, quinones such as N,N'-dimethylanthra(2,1,9-def:6,5,10-d'e'f')diisoquinoline dichloride ($ADIQ^{2+}$); porphyrins ([meso-tetrakis(N-methyl-x-pyridinium)porphyrin tetrachloride], varlamine blue B hydrochloride, Bindschedler's green; 2,6-dichloroindophenol, 2,6-dibromophenolindophenol; Brilliant crest blue (3-amino-9-dimethyl-amino-10-methylphenoxyazine chloride), methylene blue; Nile blue A (aminoaphthodiethylaminophenoxazine sulfate), indigo-5,5', 7,7'-tetrasulfonic acid, indigo-5,5',7-trisulfonic acid; phenosafranine, indigo-5-monosulfonic acid; safranine T; bis (dimethylglyoximato)-iron(II) chloride; induline scarlet, neutral red, anthracene, coronene, pyrene, 9-phenylanthracene, rubrene, binaphthyl, DPA, phenothiazene, fluoranthene, phenanthrene, chrysene, 1,8-diphenyl-1,3,5,7-octatetracene, naphthalene, acenaphthalene, perylene, TMPD and analogs and substituted derivatives of these compounds.

In one embodiment, the electron donors and acceptors are redox proteins as are known in the art. However, redox proteins in many embodiments are not preferred.

The choice of the specific electron transfer moieties will be influenced by the type of electron transfer detection used, as is generally outlined below.

In a preferred embodiment, these electron transfer moieties are covalently attached to the nucleic acid in a variety of positions. In a preferred embodiment, the attachment is via attachment to the base of the nucleoside, or via attachment to the backbone of the nucleic acid, including either to a ribose of the ribose-phosphate backbone or to a phosphate moiety. In the preferred embodiments, the compositions of the invention are designed such that the electron transfer moieties are as close to the "π-way" as possible without significantly disturbing the secondary and tertiary structure of the double helical nucleic acid, particularly the Watson-Crick basepairing. Alternatively, the attachment can be via a conductive oligomer, which is used as outlined above with a nucleoside and an electrode; that is, an electron transfer moiety may be covalently attached to a conductive oligomer at one end and to a nucleoside at the other, thus forming a general structure depicted in Structure 30:

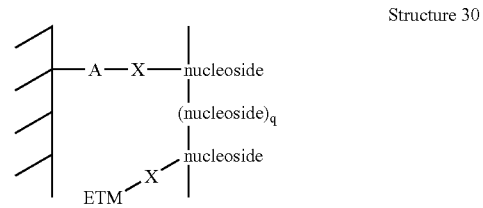

Structure 30

In Structure 30, ETM is an electron transfer moiety, X is a conductive oligomer, and q is an integer from zero to about 25, with preferred q being from about 2 to about 10. Additionally, linker moieties, for example as are generally described herein as "Z", may also be present between the nucleoside and the conductive oligomer, and/or between the conductive oligomer and the electron transfer moiety. The depicted nucleosides may be either terminal or internal nucleosides, and are usually separated by a number of nucleosides.

In a preferred embodiment, the second electron transfer moiety is attached to the base of a nucleoside, as is generally outlined above for attachment of the conductive oligomer. This is preferably done to the base of an internal nucleoside. Surprisingly and unexpectedly, this attachment does not perturb the Watson-Crick basepairing of the base to which the electron transfer moiety is attached, as long as the moiety is not too large. In fact, it appears that attachment at this site actually results in less perturbation than attachment at the ribose of the ribose-phosphate backbone, as measured by nucleic acid melting curves. Thus, when attachment to an internal base is done, the size of the second electron transfer moiety should be such that the structure of double stranded nucleic acid containing the base-attached electron transfer moiety is not significantly disrupted, and will not disrupt the annealing of single stranded nucleic acids. Preferably, then, ligands and full second electron transfer moieties are generally smaller than the size of the major groove of double stranded nucleic acid.

Alternatively, the second electron transfer moiety can be attached to the base of a terminal nucleoside. Thus, when the target sequence to be detected is n nucleosides long, a probe can be made which has the second electron transfer moiety attached at the n base. Alternatively, the probe may contain an extra terminal nucleoside at an end of the nucleic acid (n+1 or n+2), which are used to covalently attach the electron transfer moieties but which do not participate in basepair hybridization. Additionally, it is preferred that upon probe hybridization, the terminal nucleoside containing the electron transfer moiety covalently attached at the base be directly adjacent to Watson-Crick basepaired nucleosides; that is, the electron transfer moiety should be as close as possible to the stacked π-orbitals of the bases such that an electron travels through a minimum of σ bonds to reach the "π-way", or alternatively can otherwise electronically contact the π-way.

The covalent attachment to the base will depend in part on the second electron transfer moiety chosen, but in general is similar to the attachment of conductive oligomers to bases, as outlined above. In a preferred embodiment, the second electron transfer moiety is a transition metal complex, and thus attachment of a suitable metal ligand to the base leads to the covalent attachment of the electron transfer moiety. Alternatively, similar types of linkages may be used for the attachment of organic electron transfer moieties, as will be appreciated by those in the art.

In one embodiment, the C4 attached amino group of cytosine, the C6 attached amino group of adenine, or the C2 attached amino group of guanine may be used as a transition metal ligand, although in this embodiment attachment at a terminal base is preferred since attachment at these positions will perturb Watson-Crick basepairing.

Ligands containing aromatic groups can be attached via acetylene linkages as is known in the art (see Comprehensive Organic Synthesis, Trost et al., Ed., Pergamon Press, Chapter 2.4: Coupling Reactions Between sp² and sp Carbon Centers, Sonogashira, pp 521-549, and pp 950-953, hereby incorporated by reference). Structure 31 depicts a representative structure in the presence of the metal ion and any other necessary ligands; Structure 31 depicts uridine, although as for all the structures herein, any other base may also be used.

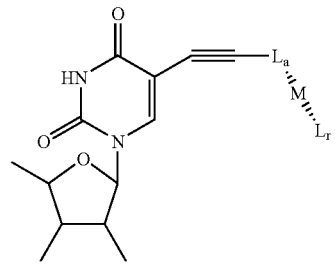

Structure 31

$L_a$ is a ligand, which may include nitrogen, oxygen, sulfur or phosphorus donating ligands or organometallic ligands such as metallocene ligands. Suitable $L_a$ ligands include, but not limited to, phenanthroline, imidazole, bpy and terpy. $L_r$ and M are as defined above. Again, it will be appreciated by those in the art, a conductive oligomer may be included between the nucleoside and the electron transfer moiety.

Similarly, as for the conductive oligomers, the linkage may be done using a linker, which may utilize an amide linkage (see generally Telser et al., J. Am. Chem. Soc. 111:7221-7226 (1989); Telser et al., J. Am. Chem. Soc. 111:7226-7232 (1989), both of which are expressly incorporated by reference). These structures are generally depicted below in Structure 32, which again uses uridine as the base, although as above, the other bases may also be used:

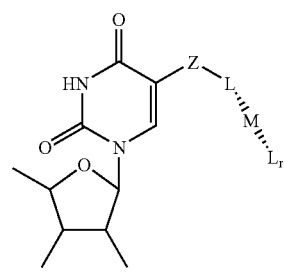

Structure 33

In this embodiment, L is a ligand as defined above, with $L_r$ and M as defined above as well. Preferably, L is amino, phen, byp and terpy.

In a preferred embodiment, the second electron transfer moiety attached to a nucleoside is a metallocene; i.e. the L and $L_r$ of Structure 32 are both metallocene ligands, $L_m$, as described above. Structure 33 depicts a preferred embodiment wherein the metallocene is ferrocene, and the base is uridine, although other bases may be used:

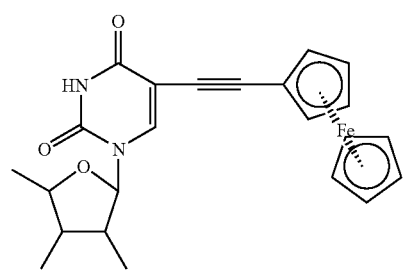

Structure 33

Preferred metallocenes include ferrocene, cobaltocene and osmiumocene.

Thus, in a preferred embodiment, the invention provides metallocenes covalently attached to nucleosides. In a preferred embodiment, the metallocene is attached to the base of a nucleoside. In a preferred embodiment, the metallocene is ferrocene or substituted ferrocene.

In a preferred embodiment, the second electron transfer moiety is attached to a ribose at any position of the ribose-phosphate backbone of the nucleic acid, i.e. either the 5' or 3' terminus or any internal nucleoside. As is known in the art, nucleosides that are modified at either the 2' or 3' position of the ribose can be made, with nitrogen, oxygen, sulfur and phosphorus-containing modifications possible. Amino-modified ribose is preferred. See generally PCT publication WO 95/15971, incorporated herein by reference. These modification groups may be used as a transition metal ligand, or as a chemically functional moiety for attachment of other transition metal ligands and organometallic ligands, or organic electron donor moieties as will be appreciated by those in the art. In this embodiment, a linker such as depicted herein for "Z" may be used as well, or a conductive oligomer between the ribose and the electron transfer moiety. Preferred embodiments utilize attachment at the 2' or 3' position of the ribose, with the 2' position being preferred. Thus for example, the conductive oligomers depicted in Structure 13, 14 and 15 may be replaced by electron transfer moieties; alternatively, as is depicted in Structure 30, the electron transfer moieties may be added to the free terminus of the conductive oligomer.

In a preferred embodiment, a metallocene serves as the second electron transfer moiety, and is attached via an amide bond as depicted below in Structure 34. The examples outline the synthesis of a preferred compound when the metallocene is ferrocene.

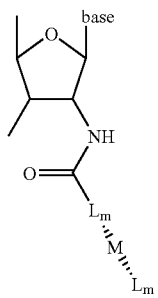

Structure 34

Amine linkages, or linkages via other heteroatoms, are also possible.

In a preferred embodiment, the second electron transfer moiety is attached to a phosphate at any position of the ribose-phosphate backbone of the nucleic acid. This may be done in a variety of ways. In one embodiment, phosphodiester bond analogs such as phosphoramide or phosphoramidite linkages may be incorporated into a nucleic acid as a transition metal ligand (see PCT publication WO 95/15971, incorporated by reference). Alternatively, the conductive oligomers depicted in Structures 16 and 17 may be replaced by electron transfer moieties; alternatively, the electron transfer moieties may be added to the free terminus of the conductive oligomer.

Preferred electron transfer moieties for covalent attachment to a single stranded nucleic acid include, but are not limited to, transition metal complexes, including metallocenes and substituted metallocenes such as metallocenophanes, and complexes of Ru, Os, Re and Pt. Particularly preferred are ferrocene and its derivatives (particularly pentamethylferrocene and ferroceneophane) and complexes of transition metals including Ru, Os, Re and Pt containing one or more amine or polyamine, imidazole, phenanthroline, pyridine, bipyridine and or terpyridine and their derivatives. For Pt, additional preferred ligands include the diimine dithiolate complexes such as quinoxaline-2,3-dithiolate complexes.

As described herein, the invention provides compositions containing electrodes as a first electron transfer moiety linked via a conductive oligomer to a nucleic acid which has at least a second electron transfer moiety covalently attached. Any combination of positions of electron transfer moiety attachment can be made; i.e. an electrode at the 5' terminus, a second electron transfer moiety at an internal position; electrode at the 5' terminus, second moiety at the 3' end; second moiety at the 5' terminus, electrode at an internal position; both electrode and second moiety at internal positions; electrode at an internal position, second moiety at the 3' terminus, etc. A preferred embodiment utilizes both the electrode and the second electron transfer moiety attached to internal nucleosides.

The compositions of the invention may additionally contain one or more labels at any position. By "label" herein is meant an element (e.g. an isotope) or chemical compound that is attached to enable the detection of the compound. Preferred labels are radioactive isotopic labels, and colored or fluorescent dyes. The labels may be incorporated into the compound at any position. In addition, the compositions of the invention may also contain other moieties such as cross-linking agents to facilitate cross-linking of the target-probe complex. See for example, Lukhtanov et al., Nucl. Acids. Res. 24(4):683 (1996) and Tabone et al., Biochem. 33:375 (1994), both of which are expressly incorporated by reference.

The compositions of the invention are generally synthesized as outlined below, generally utilizing techniques well known in the art.

The compositions may be made in several ways. A preferred method first synthesizes a conductive oligomer attached to the nucleoside, with addition of additional nucleosides followed by attachment to the electrode. A second electron transfer moiety, if present, may be added prior to attachment to the electrode or after. Alternatively, the whole nucleic acid may be made and then the completed conductive oligomer added, followed by attachment to the electrode. Alternatively, the conductive oligomer and monolayer (if present) are attached to the electrode first, followed by attachment of the nucleic acid. The latter two methods may be preferred when conductive oligomers are used which are not stable in the solvents and under the conditions used in traditional nucleic acid synthesis.

In a preferred embodiment, the compositions of the invention are made by first forming the conductive oligomer covalently attached to the nucleoside, followed by the addition of additional nucleosides to form a nucleic acid, including, if present, a nucleoside containing a second electron transfer moiety, with the last step comprising the addition of the conductive oligomer to the electrode.

The attachment of the conductive oligomer to the nucleoside may be done in several ways. In a preferred embodiment, all or part of the conductive oligomer is synthesized first (generally with a functional group on the end for attachment to the electrode), which is then attached to the nucleoside. Additional nucleosides are then added as required, with the last step generally being attachment to the electrode. Alternatively, oligomer units are added one at a time to the nucleoside, with addition of additional nucleosides and attachment to the electrode.

A general outline of a preferred embodiment is depicted in FIG. 1, using a phenyl-acetylene oligomer as generally depicted in Structure 5. Other conductive oligomers will be made using similar techniques, such as heterooligomers, or as known in the art. Thus, for example, conductive oligomers using alkene or acetylene bonds are made as is known in the art.

The conductive oligomer is then attached to a nucleoside that may contain one (or more) of the oligomer units, attached as depicted herein.

In a preferred embodiment, attachment is to a ribose of the ribose-phosphate backbone. Thus, FIG. 1 depicts attachment via an amide linkage, and FIGS. 2 and 16 depict the synthesis of compounds with amine linkages. In a preferred embodiment, there is at least a methylene group or other short aliphatic alkyl groups (as a Z group) between the nitrogen attached to the ribose and the aromatic ring of the conductive oligomer. A representative synthesis is shown in FIG. 16.

Alternatively, attachment is via a phosphate of the ribose-phosphate backbone. Examples of two synthetic schemes are shown in FIG. 4 (synthesis of Structure 16 type compounds) and FIG. 5 (synthesis of Structure 16 type compounds). Although both Figures show attachment at the 3' position of the ribose, attachment can also be made via the 2' position. In FIG. 5, Z is an ethylene linker, although other linkers may be used as well, as will be appreciated by those in the art.

In a preferred embodiment, attachment is via the base. A general scheme is depicted in FIG. 3, using uridine as the nucleoside and a phenylene-acetylene conductive oligomer. As will be appreciated in the art, amide linkages are also possible, such as depicted in Structure 12, using techniques well known in the art. In a preferred embodiment, protecting groups may be added to the base prior to addition of the conductive oligomers, as is generally outlined in FIGS. 18 and 19. In addition, the palladium cross-coupling reactions may be altered to prevent dimerization problems; i.e. two conductive oligomers dimerizing, rather than coupling to the base.

Alternatively, attachment to the base may be done by making the nucleoside with one unit of the oligomer, followed by the addition of others.

Once the modified nucleosides are prepared, protected and activated, prior to attachment to the electrode, they may be incorporated into a growing oligonucleotide by standard synthetic techniques (Gait, Oligonucleotide Synthesis: A Practical Approach, IRL Press, Oxford, UK 1984; Eckstein) in several ways. In one embodiment, one or more modified nucleosides are converted to the triphosphate form and incorporated into a growing oligonucleotide chain by using standard molecular biology techniques such as with the use of the enzyme DNA polymerase I, T4 DNA polymerase, T7 DNA polymerase, Taq DNA polymerase, reverse transcriptase, and RNA polymerases. For the incorporation of a 3' modified nucleoside to a nucleic acid, terminal deoxynucleotidyltransferase may be used. (Ratliff, Terminal deoxynucleotidyltransferase. In The Enzymes, Vol 14A. P. D. Boyer ed. pp 105-118. Academic Press, San Diego, Calif. 1981). Alternatively, and preferably, the amino nucleoside is converted to the phosphoramidite or H-phosphonate form, which are then used in solid-phase or solution syntheses of oligonucleotides. In this way the modified nucleoside, either for attachment at the ribose (i.e. amino- or thiol-modified nucleosides) or the base, is incorporated into the oligonucleotide at either an internal position or the 5' terminus. This is generally done in one of two ways. First, the 5' position of the ribose is protected with 4',4-dimethoxytrityl (DMT) followed by reaction with either 2-cyanoethoxy-bis-diisopropylaminophosphine in the presence of diisopropylammonium tetrazolide, or by reaction with chlorodiisopropylamino 2'-cyanoethyoxyphosphine, to give the phosphoramidite as is known in the art; although other techniques may be used as will be appreciated by those in the art. See Gait, supra; Caruthers, Science 230:281 (1985), both of which are expressly incorporated herein by reference.

For attachment of an electron transfer moiety to the 3' terminus, a preferred method utilizes the attachment of the modified nucleoside to controlled pore glass (CPG) or other oligomeric supports. In this embodiment, the modified nucleoside is protected at the 5' end with DMT, and then reacted with succinic anhydride with activation. The resulting succinyl compound is attached to CPG or other oligomeric supports as is known in the art. Further phosphoramidite nucleosides are added, either modified or not, to the 5' end after deprotection. Thus, the present invention provides conductive oligomers covalently attached to nucleosides attached to solid oligomeric supports such as CPG, and phosphoramidite derivatives of the nucleosides of the invention.

The growing nucleic acid chain may also comprise at least one nucleoside with covalently attached second electron transfer moiety. As described herein, modified nucleosides with covalently attached second electron transfer moieties may be made, and incorporated into the nucleic acid as outlined above for the conductive oligomer-nucleosides. When a transition metal complex is used as the second electron transfer moiety, synthesis may occur in several ways. In a preferred embodiment, the ligand(s) are added to a nucleoside, followed by the transition metal ion, and then the nucleoside with the transition metal complex attached is added to an oligonucleotide, i.e. by addition to the nucleic acid synthesizer. Alternatively, the ligand(s) may be attached, followed by incorporation into a growing oligonucleotide chain, followed by the addition of the metal ion.

In a preferred embodiment, electron transfer moieties are attached to a ribose of the ribose-phosphate backbone. This is generally done as is outlined in PCT publication SO 95/15971, using amino-modified nucleosides, at either the 2' or 3' position of the ribose. The amino group may then be used either as a ligand, for example as a transition metal ligand for attachment of the metal ion, or as a chemically functional group that can be used for attachment of other ligands or organic electron transfer moieties, for example via amide linkages, as will be appreciated by those in the art. For example, the examples describe the synthesis of a nucleoside with a metallocene linked via an amide bond to the ribose.

In a preferred embodiment, electron transfer moieties are attached to a phosphate of the ribose-phosphate backbone. As outlined herein, this may be done using phosphodiester analogs such as phosphoramidites bonds, see generally PCT publication WO 95/15971, or can be done in a similar manner to that depicted in FIGS. 4 and 5, where the conductive oligomer is replaced by a transition metal ligand or complex or an organic electron transfer moiety.

Attachment to alternate backbones, for example peptide nucleic acids or alternate phosphate linkages will be done as will be appreciated by those in the art.

In a preferred embodiment, electron transfer moieties are attached to a base of the nucleoside. This may be done in a variety of ways. In one embodiment, amino groups of the base, either naturally occurring or added as is described herein (see the figures, for example), are used either as ligands for transition metal complexes or as a chemically functional group that can be used to add other ligands, for example via an amide linkage, or organic electron transfer moieties. This is done as will be appreciated by those in the art. Alternatively, nucleosides containing halogen atoms attached to the heterocyclic ring are commercially available. Acetylene linked ligands may be added using the halogenated bases, as is generally known; see for example, Tzalis et al., Tetrahedron Lett. 36(34):6017-6020 (1995); Tzalis et al., Tetrahedron Lett. 36(2):3489-3490 (1995); and Tzalis et al., Chem. Communications (in press) 1996, all of which are hereby expressly incorporated by reference. See also the examples, which describes the synthesis of a metallocene attached via an acetylene linkage to the base.

In one embodiment, the nucleosides are made with transition metal ligands, incorporated into a nucleic acid, and then the transition metal ion and any remaining necessary ligands are added as is known in the art. In an alternative embodiment, the transition metal ion and additional ligands are added prior to incorporation into the nucleic acid.

In some embodiments, as outlined herein, conductive oligomers are used between the second electron transfer moieties and the nucleosides. These are made using the techniques described herein, with the addition of the terminal second electron transfer moiety.

Once the nucleic acids of the invention are made, with a covalently attached conductive oligomer and optionally a second electron transfer moiety, the conductive oligomer is attached to the electrode. The method will vary depending on the type of electrode used. As is described herein, the conductive oligomers are generally made with a terminal "A" linker to facilitate attachment to the electrode. For the purposes of this application, a sulfur-gold attachment is considered a covalent attachment.

In a preferred embodiment, conductive oligomers are covalently attached via sulfur linkages to the electrode. However, surprisingly, traditional protecting groups for use of attaching molecules to gold electrodes are generally ideal for use in both synthesis of the compositions described herein and inclusion in oligonucleotide synthetic reactions. Accordingly, the present invention provides novel methods for the attachment of conductive oligomers to gold electrodes, utilizing unusual protecting groups, including ethylpyridine, and trimethylsilylethyl as is depicted in the Figures.

This may be done in several ways. In a preferred embodiment, the subunit of the conductive oligomer which contains the sulfur atom for attachment to the electrode is protected with an ethyl-pyridine or trimethylsilylethyl group. For the former, this is generally done by contacting the subunit containing the sulfur atom (preferably in the form of a sulfhydryl) with a vinyl pyridine group or vinyl trimethylsilylethyl group under conditions whereby an ethylpyridine group or trimethylsilylethyl group is added to the sulfur atom.

This subunit also generally contains a functional moiety for attachment of additional subunits, and thus additional subunits are attached to form the conductive oligomer. The conductive oligomer is then attached to a nucleoside, and additional nucleosides attached. The protecting group is then removed and the sulfur-gold covalent attachment is made. Alternatively, all or part of the conductive oligomer is made, and then either a subunit containing a protected sulfur atom is added, or a sulfur atom is added and then protected. The conductive oligomer is then attached to a nucleoside, and additional nucleosides attached. Alternatively, the conductive oligomer attached to a nucleic acid is made, and then either a subunit containing a protected sulfur atom is added, or a sulfur atom is added and then protected. Alternatively, the ethyl pyridine protecting group may be used as above, but removed after one or more steps and replaced with a standard protecting group like a disulfide. Thus, the ethyl pyridine or trimethylsilylethyl group may serve as the protecting group for some of the synthetic reactions, and then removed and replaced with a traditional protecting group.

By "subunit" of a conductive polymer herein is meant at least the moiety of the conductive oligomer to which the sulfur atom is attached, although additional atoms may be present, including either functional groups which allow the addition of additional components of the conductive oligomer, or additional components of the conductive oligomer. Thus, for example, when Structure 2 oligomers are used, a subunit comprises at least the first Y group.

A preferred method comprises 1) adding an ethyl pyridine or trimethylsilylethyl protecting group to a sulfur atom attached to a first subunit of a conductive oligomer, generally done by adding a vinyl pyridine or trimethylsilylethyl group to a sulfhydryl; 2) adding additional subunits to form the conductive oligomer; 3) adding at least a first nucleoside to the conductive oligomer; 4) adding additional nucleosides to the first nucleoside to form a nucleic acid; 5) attaching the conductive oligomer to the gold electrode. This may also be done in the absence of nucleosides, as is described in the Examples.

The above method may also be used to attach passayation molecules to a gold electrode.

In a preferred embodiment, a monolayer of passayation agents is added to the electrode. Generally, the chemistry of addition is similar to or the same as the addition of conductive oligomers to the electrode, i.e. using a sulfur atom for attachment to a gold electrode, etc. Compositions comprising monolayers in addition to the conductive oligomers covalently attached to nucleic acids (with or without second electron transfer moieties) may be made in at least one of five ways: (1) addition of the monolayer, followed by subsequent addition of the conductive oligomer-nucleic acid complex; (2) addition of the conductive oligomer-nucleic acid complex followed by addition of the monolayer; (3) simultaneous addition of the monolayer and conductive oligomer-nucleic acid complex; (4) formation of a monolayer (using any of 1, 2 or 3) which includes conductive oligomers which terminate in a functional moiety suitable for attachment of a completed nucleic acid; or (5) formation of a monolayer which includes conductive oligomers which terminate in a functional moiety suitable for nucleic acid synthesis, i.e. the nucleic acid is synthesized on the surface of the monolayer as is known in the art. Such suitable functional moieties include, but are not limited to, nucleosides, amino groups, carboxyl groups, protected sulfur moieties, or hydroxyl groups for phosphoramidite additions. The examples describe the formation of a monolayer on a gold electrode using the preferred method (1).

As will be appreciated by those in the art, electrodes may be made that have any combination of nucleic acids, conductive oligomers and passayation agents. Thus, a variety of different conductive oligomers or passayation agents may be used on a single electrode.

Once made, the compositions find use in a number of applications, as described herein. In a preferred embodiment, the compositions of the invention are used as probes in hybridization assays to detect target sequences in a sample. The term "target sequence" or grammatical equivalents herein means a nucleic acid sequence on a single strand of nucleic acid. The target sequence may be a portion of a gene, a regulatory sequence, genomic DNA, cDNA, RNA including mRNA and rRNA, or others. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. As is outlined more fully below, probes are made to hybridize to target sequences to determine the presence or absence of the target sequence in a sample. Generally speaking, this term will be understood by those skilled in the art.

If required, the target sequence is prepared using known techniques. For example, the sample may be treated to lyse the cells, using known lysis buffers, electroporation, etc., with purification and/or amplification occuring as needed, as will be appreciated by those in the art.

The probes of the present invention are designed to be complementary to the target sequence, such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence.

A variety of hybridization conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. The hybridization conditions may also vary when a non-ionic backbone, i.e. PNA is used, as is known in the art. In addition, cross-linking agents may be added after target binding to cross-link, i.e. covalently attach, the two strands of the hybridization complex.

In a preferred embodiment, single stranded nucleic acids are made which contain a first electron transfer moiety, an electrode, and at least a second electron transfer moiety. Hybridization to a target sequence forms a double stranded hybridization complex. In a hybridization complex, at least the sequence between the nucleosides containing the electron transfer moieties is double stranded, i.e. contains stacked π-orbitals, such that upon initiation, the complex is capable of transferring at least one electron from one of the electron transfer moieties to the other. As will be appreciated by those in the art, an electrode may serve as either an electron donor or acceptor, and the choice of the second electron transfer species is made accordingly.

In an alternative embodiment, compositions comprising a) a first single stranded nucleic acid covalently attached to an electrode via a conductive oligomer and b) a second single stranded nucleic acid containing a second electron transfer moiety, are made. In this embodiment, the first single stranded nucleic acid is capable of hybridizing to a first target domain, and the second single stranded nucleic acid is capable of hybridizing to a second target domain. The terms "first target domain" and "second target domain" or grammatical equivalents herein means two portions of a target sequence within a nucleic acid which is under examination. The first target domain may be directly adjacent to the second target domain, or the first and second target domains may be separated by an intervening target domain. Preferably, there are no gaps between the domains; i.e. they are contiguous. The terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain.

In this embodiment, the first single stranded nucleic acid is hybridized to the first target domain, and the second single stranded nucleic acid is hybridized to the second target domain to form a hybridization complex. As outlined above, the hybridization complex is then capable of transferring at least one electron between the electron transfer moieties upon initiation.

In one embodiment, compositions comprising a) a single stranded nucleic acid covalently attached to an electrode via a conductive oligomer, and b) a target nucleic acid are made. In this embodiment, once hybridization of the target and the probe occurs, a hybridization indicator is added. Hybridization indicators serve as an electron transfer moiety that will preferentially associate with double stranded nucleic acid is added, usually reversibly, similar to the method of Millan et al., Anal. Chem. 65:2317-2323 (1993); Millan et al., Anal. Chem. 662943-2948 (1994), both of which are hereby expressly incorporated by reference. Hybridization indicators include intercalators and minor and/or major groove binding moieties. In a preferred embodiment, intercalators may be used; since intercalation generally only occurs in the presence of double stranded nucleic acid, only in the presence of target hybridization will electron transfer occur. Intercalating transition metal complex electron transfer moieties are known in the art. Similarly, major or minor groove binding moieties, such as methylene blue, may also be used in this embodiment.

In addition, hybridization indicators may be used in any or all of the other systems of the invention; for example, they may be added to facilitate, quench or amplify the signal generated by the system, in addition to the covalently attached electron transfer moieties. For example, it has been shown by Millan, above, that some hybridization indicators may preferentially bind to perfectly complementary double stranded nucleic acids over nucleic acids containing mismatches. This could serve to contribute additional information about the system. Similarly, electronic coupling could be increased due to hybridization indicator binding. Alternatively, quenching of the electron transfer signal could be achieved using hybridization indicators, whereby the electrons would flow between the second electron transfer moiety and the hybridization indicator, rather than the electrode.

A further embodiment utilizes compositions comprising a) a first single stranded nucleic acid covalently attached to an electrode via a conductive oligomer; b) a second single stranded nucleic acid containing a second electron transfer moiety; and c) an intervening single stranded nucleic acid, which may or may not be labelled or contain an electron transfer moiety. As generally outlined in PCT WO 95/15971, the first single stranded nucleic acid hybridizes to the first target domain, the second single stranded nucleic acid hybridizes to the second target domain, and the intervening nucleic acid hybridizes to the intervening target domain, with electron transfer upon initiation. The intervening nucleic acid may be any length, taking into consideration the parameters for the distance between the electron transfer moieties, although it may be a single nucleoside.

In addition, the first and second, or first, intervening and second, nucleic acids may be ligated together prior to the electron transfer reaction, using standard molecular biology techniques such as the use of a ligase.

In one embodiment, the compositions of the invention are used to detect mismatches in a complementary target sequence. A mismatch, whether it be a substitution, insertion or deletion of a nucleoside or nucleosides, results in incorrect base pairing in a hybridized double helix of nucleic acid. Accordingly, if the path of an electron from an electron donor moiety to an electron acceptor moiety spans the region where the mismatch lies, the electron transfer will be reduced such that a change in the relative impedance will be seen. Therefore, in this embodiment, the electron donor moiety is attached to the nucleic acid at a 5' position from the mutation, and the electron acceptor moiety is attached at a 3' position, or vice versa.

Electron transfer is generally initiated electronically, with voltage being preferred. A potential is applied to a sample containing modified nucleic acid probes. Precise control and variations in the applied potential can be via a potentiostat and either a three electrode system (one reference, one sample and one counter electrode) or a two electrode system (one sample and one counter electrode). This allows matching of applied potential to peak electron transfer potential of the system which depends in part on the choice of electron acceptors attached to the nucleic acid and in part on the conductive oligomer used. As described herein, ferrocene is a preferred electron transfer moiety.

Preferably, initiation and detection is chosen to maximize the relative difference between the impedances of double stranded nucleic acid and single stranded nucleic acid systems.

The efficiency of electron transfer through nucleic acid is a function of the impedance of the compound.

In a preferred embodiment, a co-reductant or co-oxidant (collectively, co-redoxant) is used, as an additional electron source or sink. See generally Sato et al., Bull. Chem. Soc. Jpn 66:1032 (1993); Uosaki et al., Electrochimica Acta 36:1799 (1991); and Alleman et al., J. Phys. Chem 100:17050 (1996); all of which are incorporated by reference.

In a preferred embodiment, an input electron source in solution is used in the initiation of electron transfer, preferably when initiation and detection are being done using DC current, and when a passayation agent monolayer is present on the electrode. This may be done in several general ways. In a preferred embodiment, an input electron source is used that has a lower or similar redox potential than the second electron transfer moiety (ETM) covalently attached to the probe nucleic acid. Thus, at voltages above the redox potential of the input electron source, both the second ETM and the input electron source are oxidized and can thus donate electrons; the ETM donates through the hybridization complex, through the conductive oligomer, to the electrode, and the input source donates to the ETM. For example, ferrocene, as a second ETM attached to the compositions of the invention as described in the examples, has a redox potential of roughly 200 mV in aqueous solution (which changes slightly depending on what the ferrocene is bound to). Ferrocyanide, an electron source, has a redox potential of roughly 200 mV as well (in aqueous solution). Accordingly, at or above voltages of roughly 200 mV, ferrocene is converted to ferricenium, which then transfers an electron to the nucleic acid. If this nucleic acid is double stranded, transfer proceeds rapidly through the double stranded nucleic acid, through the conductive oligomer, to the electrode. Now the ferricyanide can be oxidized to transfer an electron to the ETM. In this way, the electron source (or co-reductant) serves to amplify the signal generated in the system, as the electron source molecules rapidly and repeatedly donate electrons to the second ETM attached to the nucleic acid. The rate of electron donation or acceptance will be limited by the rate of diffusion of the co-reductant, which in turn is affected by the concentration and size, etc.

Alternatively, input electron sources that have lower redox potentials than the second ETM are used. At voltages less than the redox potential of the ETM, but higher than the redox potential of the electron source, the input source such as ferrocyanide is unable to be oxidized and thus is unable to donate an electron to the ETM; i.e. no electron transfer occurs. The use of electron source molecules, however, is only possible when an insulating or passayation layer is present, since otherwise the source molecule will transfer electrons directly to the electrode. Accordingly, in a preferred embodiment, an electron source is used in solution to amplify the signal generated in the presence of hybridized target sequence.

In an alternate preferred embodiment, an input electron source is used that has a higher redox potential than the second electron transfer moiety (ETM) covalently attached to the probe nucleic acid. For example, luminol, an electron source, has a redox potential of roughly 720 mV. At voltages higher than the redox potential of the ETM, but lower than the redox potential of the electron source, i.e. 200-720 mV, the ferrocene is oxidized, and transfers a single electron to the electrode via the conductive oligomer. However, the ETM is unable to accept any electrons from the luminol electron source, since the voltages are less than the redox potential of the luminol. However, at or above the redox potential of luminol, the luminol then transfers an electron to the ETM, allowing rapid and repeated electron transfer. In this way, the electron source (or co-reductant) serves to amplify the signal generated in the system, as the electron source molecules rapidly and repeatedly donate electrons to the second ETM attached to the nucleic acid.

Luminol has the added benefit of becoming a chemiluminescent species upon oxidation (see Jirka et al., Analytica Chimica Acta 284:345 (1993)), thus allowing photo-detection of electron transfer through double-stranded nucleic acid. Thus, as long as the luminol is unable to contact the electrode directly, i.e. in the presence of a passayation layer, luminol can only be oxidized by transferring an electron to the second electron transfer moiety on the nucleic acid (e.g. ferrocene). When double stranded nucleic acid is not present, i.e. when the target sequence is not hybridized to the composition of the invention, the system has a high impedance, resulting in a low photon emission and thus a low (if any) signal from the luminol. In the presence of double stranded nucleic acid, i.e. target sequence hybridization, the second electron transfer moieties have low impedance, thus generating a much larger signal. Thus, the measure of luminol oxidation by photon emission is an indirect measurement of the ability of the second electron transfer moiety to donate electrons to the electrode. Furthermore, since photon detection is generally more sensitive than electronic detection, the sensitivity of the system may be increased. Initial results suggest that luminescence may depend on hydrogen peroxide concentration, pH, and luminol concentration, the latter of which appears to be non-linear.

Suitable electron source molecules are well known in the art, and include, but are not limited to, ferricyanide, and luminol.

Alternatively, output electron acceptors or sinks could be used, i.e. the above reactions could be run in reverse, with the ETM such as a metallocene receiving an electron from the electrode, converting it to the metallicenium, with the output electron acceptor then accepting the electron rapidly and repeatedly. In this embodiment, cobalticenium is the preferred ETM.

Electron transfer through nucleic acid can be detected in a variety of ways. A variety of detection methods may be used, including, but not limited to, optical detection, which includes fluorescence, phosphorescence, luminiscence, chemiluminescence, electrochemiluminescence, and refractive index; and electronic detection, including, but not limited to, amperommetry, voltammetry, capacitance and impedence. These methods include time or frequency dependent methods based on AC or DC currents, pulsed methods, lock-in techniques, filtering (high pass, low pass, band pass), and time-resolved techniques including time-resolved fluorescence. In some embodiments, all that is required is electron transfer detection; in others, the rate of electron transfer may be determined.

In one embodiment, the efficient transfer of electrons from one end of a nucleic acid double helix to the other results in stereotyped changes in the redox state of both the electron donor and acceptor. With many electron transfer moieties including the complexes of ruthenium containing bipyridine, pyridine and imidazole rings, these changes in redox state are associated with changes in spectral properties. Significant differences in absorbance are observed between reduced and oxidized states for these molecules. See for example Fabbrizzi et al., Chem. Soc. Rev. 1995 pp 197-202). These differences can be monitored using a spectrophotometer or simple photomultiplier tube device.

In this embodiment, possible electron donors and acceptors include all the derivatives listed above for photoactivation or initiation. Preferred electron donors and acceptors have characteristically large spectral changes upon oxidation and reduction resulting in highly sensitive monitoring of electron transfer. Such examples include $Ru(NH_3)_4py$ and $Ru(bpy)_2im$ as preferred examples. It should be understood that only the donor or acceptor that is being monitored by absorbance need have ideal spectral characteristics. That is, the electron acceptor can be optically invisible if only the electron donor is monitored for absorbance changes.

In a preferred embodiment, the electron transfer is detected fluorometrically. Numerous transition metal complexes, including those of ruthenium, have distinct fluorescence properties. Therefore, the change in redox state of the electron donors and electron acceptors attached to the nucleic acid can be monitored very sensitively using fluorescence, for example with $Ru(4,7-biphenyl_2-phenanthroline)_3^{2+}$. The production of this compound can be easily measured using standard fluorescence assay techniques. For example, laser induced fluorescence can be recorded in a standard single cell fluorimeter, a flow through "on-line" fluorimeter (such as those attached to a chromatography system) or a multi-sample "plate-reader" similar to those marketed for 96-well immuno assays.

Alternatively, fluorescence can be measured using fiber optic sensors with nucleic acid probes in solution or attached to the fiber optic. Fluorescence is monitored using a photomultiplier tube or other light detection instrument attached to the fiber optic. The advantage of this system is the extremely small volumes of sample that can be assayed.

In addition, scanning fluorescence detectors such as the FluorImager sold by Molecular Dynamics are ideally suited to monitoring the fluorescence of modified nucleic acid molecules arrayed on solid surfaces. The advantage of this system is the large number of electron transfer probes that can be scanned at once using chips covered with thousands of distinct nucleic acid probes.

Many transition metal complexes display fluorescence with large Stokes shifts. Suitable examples include bis- and trisphenanthroline complexes and bis- and trisbipyridyl complexes of transition metals such as ruthenium (see Juris, A., Balzani, V., et. al. Coord. Chem. Rev., V. 84, p. 85-277, 1988). Preferred examples display efficient fluorescence (reasonably high quantum yields) as well as low reorganization energies. These include $Ru(4,7-biphenyl_2-phenanthroline)_3^{2+}$, $Ru(4,4'-diphenyl-2,2'-bipyridine)_3^{2+}$ and platinum complexes (see Cummings et al., J. Am. Chem. Soc. 118:1949-1960 (1996), incorporated by reference).

Alternatively, a reduction in fluorescence associated with hybridization can be measured using these systems. An electron transfer "donor" molecule that fluoresces readily when on single stranded nucleic acid (with an "acceptor" on the other end) will undergo a reduction in fluorescent intensity when complementary nucleic acid binds the probe allowing efficient transfer of the excited state electron. This drop in fluorescence can be easily monitored as an indicator of the presence of a target sequence using the same methods as those above.

In a further embodiment, electrochemiluminescence is used as the basis of the electron transfer detection. With some electron transfer moieties such as $Ru^{2+}(bpy)_3$, direct luminescence accompanies excited state decay. Changes in this property are associated with nucleic acid hybridization and can be monitored with a simple photomultiplier tube arrangement (see Blackburn, G. F. Clin. Chem. 37: 1534-1539 (1991); and Juris et al., supra.

In a preferred embodiment, electronic detection is used, including amperommetry, voltammetry, capacitance, and impedance. Suitable techniques include, but are not limited to, electrogravimetry; coulometry (including controlled potential coulometry and constant current coulometry); voltametry (cyclic voltametry, pulse voltametry (normal pulse voltametry, square wave voltametry, differential pulse voltametry, Osteryoung square wave voltametry, and coulostatic pulse techniques); stripping analysis (anodic stripping analysis, cathiodic stripping analysis, square wave stripping voltammetry); conductance measurements (electrolytic conductance, direct analysis); time-dependent electrochemical analyses (chronoamperometry, chronopotentiometry, cyclic chronopotentiometry and amperometry, AC polography, chronogalvametry, and chronocoulometry); AC impedance measurement; capacitance measurement; AC voltametry; and photoelectrochemistry.

In a preferred embodiment, monitoring electron transfer through nucleic acid is via amperometric detection. This method of detection involves applying a potential (as compared to a separate reference electrode) between the nucleic acid-conjugated electrode and a reference (counter) electrode in the sample containing target genes of interest. Electron transfer of differing efficiencies is induced in samples in the presence or absence of target nucleic acid; that is, the presence or absence of the target nucleic acid alters the impedance of the nucleic acid (i.e. double stranded versus single stranded) system which can result in different currents.

The device for measuring electron transfer amperometrically involves sensitive current detection and includes a means of controlling the voltage potential, usually a potentiostat. This voltage is optimized with reference to the potential of the electron donating complex on the nucleic acid. Possible electron donating complexes include those previously mentioned with complexes of iron, osmium, platinum, cobalt, rhenium and ruthenium being preferred and complexes of iron being most preferred.

In a preferred embodiment, alternative electron detection modes are utilized. For example, potentiometric (or voltammetric) measurements involve non-faradaic (no net current flow) processes and are utilized traditionally in pH and other ion detectors. Similar sensors are used to monitor electron transfer through nucleic acid. In addition, other properties of insulators (such as resistance) and of conductors (such as conductivity, impedance and capacitance) could be used to monitor electron transfer through nucleic acid. Finally, any system that generates a current (such as electron transfer) also generates a small magnetic field, which may be monitored in some embodiments.

It should be understood that one benefit of the fast rates of electron transfer observed in the compositions of the invention is that time resolution can greatly enhance the signal-tonoise results of monitors based on absorbance, fluorescence and electronic current. The fast rates of electron transfer of the present invention result both in high signals and stereotyped delays between electron transfer initiation and completion. By amplifying signals of particular delays, such as through the use of pulsed initiation of electron transfer and "lock-in" amplifiers of detection, between two and four orders of magnitude improvements in signal-to-noise may be achieved.

In a preferred embodiment, electron transfer is initiated using alternating current (AC) methods. Without being bound by theory, it appears that nucleic acids, bound to an electrode, generally respond similarly to an AC voltage resistor and capacitor in series. Basically, any methods which enable the determination of the nature of these complexes, which act as a resistor and capacitor, can be used as the basis of detection. Surprisingly, traditional electrochemical theory, such as exemplified in Laviron et al., J. Electroanal. Chem. 97:135 (1979) and Laviron et al., J. Electroanal. Chem. 105:35 (1979), both of which are incorporated by reference, do not accurately model the systems described herein, except for very small $E_{AC}$ (less than 10 mV). That is, the AC current (I) is not accurately described by Laviron's equation. This may be due in part to the fact that this theory assumes an unlimited source and sink of electrons, which is not true in the present systems.

Accordingly, alternate equations were developed, using the Nernst equation and first principles to develop a model which more closely simulates the results. This was derived as follows. The Nernst equation, Equation 1 below, describes the ratio of oxidized (O) to reduced (R) molecules (number of molecules=n) at any given voltage and temperature, since not every molecule gets oxidized at the same oxidation potential.

Equation 1

$$E_{DC} = E_0 + \frac{RT}{nF} \ln \frac{[O]}{[R]} \quad (1)$$

$E_{DC}$ is the electrode potential, $E_0$ is the formal potential of the metal complex, R is the gas constant, T is the temperature in degrees Kelvin, n is the number of electrons transferred, F is faraday's constant, [O] is the concentration of oxidized molecules and [R] is the concentration of reduced molecules.

The Nernst equation can be rearranged as shown in Equations 2 and 3:

Equation 2

$$E_{DC} - E_0 = \frac{RT}{nF} \ln \frac{[O]}{[R]} \quad (2)$$

$E_{DC}$ is the DC component of the potential.

Equation 3

$$\exp^{\frac{nF}{RT}(E_{DC}-E_0)} = \frac{[O]}{[R]} \quad (3)$$

Equation 3 can be rearranged as follows, using normalization of the concentration to equal 1 for simplicity, as shown in Equations 4, 5 and 6. This requires the subsequent multiplication by the total number of molecules.

$[O]+[R]=1$ \hfill Equation 4

$[O]=1-[R]$ \hfill Equation 5

$[R]=1-[O]$ \hfill Equation 6

Plugging Equation 5 and 6 into Equation 3, and the fact that nF/RT equals 38.9 V$^{-1}$, for n=1, gives Equations 7 and 8, which define [O] and [R], respectively:

Equation 7

$$[O] = \frac{\exp^{38.9(E-E_0)}}{1 + \exp^{38.9(E-E_0)}} \quad (4)$$

Equation 8

$$[R] = \frac{1}{1 + \exp^{38.9(E-E_0)}} \quad (5)$$

Taking into consideration the generation of an AC faradaic current, the ratio of [O]/[R] at any given potential must be evaluated. At a particular $E_{DC}$ with an applied $E_{AC}$, as is generally described herein, at the apex of the $E_{AC}$ more molecules will be in the oxidized state, since the voltage on the surface is now ($E_{DC}+E_{AC}$); at the bottom, more will be reduced since the voltage is lower. Therefore, the AC current at a given $E_{DC}$ will be dictated by both the AC and DC voltages, as well as the shape of the curve. Specifically, if the number of oxidized molecules at the bottom of the AC cycle is subtracted from the amount at the top of the AC cycle, the total change in a given AC cycle is obtained, as is generally described by Equation 9. Dividing by 2 then gives the AC amplitude.

$i_{AC}$=(electrons at $E_{DC}+E_{AC}$)−(electrons at $E_{DC}-E_{AC}$) \hfill Equation 9

Equation 10 thus describes the AC current which should result:

$i_{AC}=C_0F\omega^{1/2}([O]_{E_{DC}+E_{AC}}-[O]_{E_{DC}-E_{AC}})$ (6) \hfill Equation 10

As depicted in Equation 11, the total AC current will be the number of redox molecules C), times faraday's constant (F), times the AC frequency ($\omega$), times 0.5 (to take into account the AC amplitude), times the ratios derived above in Equation 7. The AC voltage is approximated by the average, $E_{AC}2/\pi$.

Equation 11

$$i_{AC} = \frac{C_0 F \omega}{2} \left( \frac{\exp^{38.9\left[E_{DC}+\frac{E_{AC}2}{\pi}-E_0\right]}}{1+\exp^{38.9\left[E_{DC}+\frac{E_{AC}2}{\pi}-E_0\right]}} \right) - \frac{\exp^{38.9\left[E_{DC}+\frac{E_{AC}2}{\pi}-E_0\right]}}{1+\exp^{38.9\left[E_{DC}+\frac{E_{AC}2}{\pi}-E\right]}} \quad (7)$$

Using Equation 11, simulations were generated using increasing overpotential. FIG. 22A shows one of these simulations, while FIG. 22B depicts a simulation based on traditional theory. FIGS. 23A and 23B depicts actual experimental data using the Fc-wire of Example 7 plotted with the simulation, and shows that the model fits the experimental data very well. In some cases the current is smaller than predicted, however this has been shown to be caused by ferrocene degradation which may be remedied in a number of ways. However, Equation 11 does not incorporate the effect of electron transfer rate nor of instrument factors. Electron transfer rate is important when the rate is close to or lower than the applied frequency. Thus, the true $i_{AC}$ should be a function of all three, as depicted in Equation 12.

$i_{AC}=f$(Nernst factors)$f(k_{ET})f$(instrument factors) \hfill Equation 12

These equations can be used to model and predict the expected AC currents in systems which use input signals comprising both AC and DC components. As outlined above, traditional theory surprisingly does not model these systems at all, except for very low voltages.

In general, a single stranded probe nucleic acid system has a high impedance, and a double stranded nucleic acid system (i.e. probe hybridized to target to form a hybridization complex) has a lower impedance. This difference in impedance serves as the basis of a number of useful AC detection techniques, as outlined below, but as will be appreciated by those in the art, a wide number of techniques may be used. In addition, the use of AC input and output signals enables the identification of different species based on phase shifting between the AC voltage applied and the voltage or current response. Thus, AC detection gives several advantages as is generally discussed below, including an increase in sensitivity, the ability to monitor changes using phase shifting, and the ability to "filter out" background noise.

Accordingly, when using AC initiation and detection methods, the frequency response of the system changes as a result of hybridization to form a double-stranded nucleic acid. By "frequency response" herein is meant a modification of signals as a result of electron transfer between the electrode and the second electron transfer moiety. This modification is different depending on signal frequency. A frequency response includes AC currents at one or more frequencies, phase shifts, DC offset voltages, faradaic impedance, etc.

In a preferred embodiment, a target sequence is added to a probe single stranded nucleic acid. Preferably, the probe single stranded nucleic acid comprises a covalently attached first electron transfer moiety comprising an electrode, and a covalently attached second electron transfer moiety as described above. However, as outlined herein, it is also possible to use a variety of other configurations in the system, including a second electron transfer moiety attached to the target nucleic acid, a second probe nucleic acid containing a second electron transfer moiety, intervening nucleic acids, etc.

In a preferred embodiment, the single stranded nucleic acid is covalently attached to the electrode via a spacer. By "spacer" herein is meant a moiety which holds the nucleic acid off the surface of the electrode. In a preferred embodiment, the spacer is a conductive oligomer as outlined herein, although suitable spacer moieties include passayation agents and insulators as outlined above. The spacer moieties may be substantially non-conductive, although preferably (but not required) is that the rate of electron transfer through the spacer is faster than the rate through single stranded nucleic acid, although substantially non-conductive spacers are generally preferred. In general, the length of the spacer is as outlined for conductive polymers and passayation agents. Similarly, spacer moieties are attached as is outlined above for conductive oligomers, passayation agents and insulators, for example using the same "A" linker defined herein.

The target sequence is added to the composition under conditions whereby the target sequence, if present, will bind to the probe single stranded nucleic acid to form a hybridization complex, as outlined above.

A first input electrical signal is then applied to the system, preferably via at least the sample electrode (containing the complexes of the invention) and the counter electrode, to initiate electron transfer between the electrode and the second electron transfer moiety. Three electrode systems may also be used, with the voltage applied to the reference and working electrodes. The first input signal comprises at least an AC component. The AC component may be of variable amplitude and frequency. Generally, for use in the present methods, the AC amplitude ranges from about 1 mV to about 1.1 V, with from about 10 mV to about 800 mV being preferred, and from about 10 mV to about 500 mV being especially preferred. The AC frequency ranges from about 0.01 Hz to about 10 MHz, with from about 1 Hz to about 1 MHz being preferred, and from about 1 Hz to about 100 kHz being especially preferred.

Surprisingly, the use of combinations of AC and DC signals allows the differentiation between single-stranded nucleic acid and double stranded nucleic acid, as is outlined herein. In addition, signals comprised of AC and DC components also allow surprising sensitivity and signal maximization.

In a preferred embodiment, the first input signal comprises a DC component and an AC component. That is, a DC offset voltage between the sample and counter electrodes is swept through the electrochemical potential of the second electron transfer moiety (for example, when ferrocene is used, the sweep is generally from 0 to 500 mV). The sweep is used to identify the DC voltage at which the maximum response of the system is seen. This is generally at or about the electrochemical potential of the second electron transfer moiety. Once this voltage is determined, either a sweep or one or more uniform DC offset voltages may be used. DC offset voltages of from about −1 V to about +1.1 V are preferred, with from about −500 mV to about +800 mV being especially preferred, and from about −300 mV to about 500 mV being particularly preferred. In a preferred embodiment, the DC offset voltage is not zero. On top of the DC offset voltage, an AC signal component of variable amplitude and frequency is applied. If the nucleic acid has a low enough impedance to respond to the AC perturbation, an AC current will be produced due to electron transfer between the electrode and the second electron transfer moiety.

For defined systems, it may be sufficient to apply a single input signal to differentiate between single stranded and double stranded (i.e. the presence of the target sequence) nucleic acid. Alternatively, a plurality of input signals are applied. As outlined herein, this may take a variety of forms, including using multiple frequencies, multiple DC offset voltages, or multiple AC amplitudes, or combinations of any or all of these.

Thus, in a preferred embodiment, multiple DC offset voltages are used, although as outlined above, DC voltage sweeps are preferred. This may be done at a single frequency, or at two or more frequencies.

In a preferred embodiment, the AC amplitude is varied. Without being bound by theory, it appears that increasing the amplitude increases the driving force. Thus, higher amplitudes, which result in higher overpotentials give faster rates of electron transfer. Thus, generally, the same system gives an improved response (i.e. higher output signals) at any single frequency through the use of higher overpotentials at that frequency. Thus, the amplitude may be increased at high frequencies to increase the rate of electron transfer through the system, resulting in greater sensitivity. In addition, this may be used, for example, to induce responses in slower systems such as single stranded nucleic acids for identification, calibration and/or quantification. Thus, the amount of unhybridized single stranded nucleic acid on an electrode may be compared to the amount of hybridized double stranded nucleic acid to quantify the amount of target sequence in a sample. This is quite significant to serve as an internal control of the sensor or system. This allows a measurement either prior to the addition of target or after, on the same molecules that will be used for detection, rather than rely on a similar but different control system. Thus, the actual molecules that will be used for the detection can be quantified prior to any experiment. For example, a preliminary run at 1 Hz or less, for example, will quantify the actual number of molecules that are on the surface of the electrode. The sample can then be added, an output signal determined, and the ratio of bound/unbound molecules determined. This is a significant advantage over prior methods.

In a preferred embodiment, measurements of the system are taken at least two separate amplitudes or overpotentials, with measurements at a plurality of amplitudes being preferred. As noted above, changes in response as a result of changes in amplitude may form the basis of identification, calibration and quantification of the system. In addition, one or more AC frequencies can be used as well.

In a preferred embodiment, the AC frequency is varied. At different frequencies, different molecules respond in different ways. As will be appreciated by those in the art, increasing the frequency generally increases the output current. However, when the frequency is greater than the rate at which electrons may travel between the electrode and the second electron transfer moiety, higher frequencies result in a loss or decrease of output signal. For example, as depicted in FIG. 11, a response may be detected at 1 Hz for both single stranded nucleic acid and double stranded nucleic acid. However, at the higher frequencies, such as 200 Hz and above, the response of the single stranded nucleic acid is absent, while the response of the double stranded nucleic acid continues to increase. At some point, the frequency will be greater than the rate of electron transfer through even double-stranded nucleic acid, and then the output signal will also drop. Thus, the different frequency responses of single stranded and double stranded nucleic acids, based on the rate at which electrons may travel through the nucleic acid (i.e. the impedance of the nucleic acid), forms the basis of selective detection of double stranded nucleic acids versus single stranded nucleic acids.

In one embodiment, detection utilizes a single measurement of output signal at a single frequency. That is, the frequency response of a single stranded nucleic acid can be previously determined to be very low at a particular high frequency. Using this information, any response at a high frequency, for example such as 10 to 100 kHz, where the frequency response of the single stranded nucleic acid is very low or absent, will show the presence of the double stranded hybridization complex. That is, any response at a high frequency is characteristic of the hybridization complex. Thus, it may only be necessary to use a single input high frequency, and any frequency response is an indication that the hybridization complex is present, and thus that the target sequence is present.

In addition, the use of AC techniques allows the significant reduction of background signals at any single frequency due to entities other than the covalently attached nucleic acids, i.e. "locking out" or "filtering" unwanted signals. That is, the frequency response of a charge carrier or redox active molecule in solution will be limited by its diffusion coefficient and charge transfer coefficient. Accordingly, at high frequencies, a charge carrier may not diffuse rapidly enough to transfer its charge to the electrode, and/or the charge transfer kinetics may not be fast enough. This is particularly significant in embodiments that do not utilize a passayation layer monolayer or have partial or insufficient monolayers, i.e. where the solvent is accessible to the electrode. As outlined above, in DC techniques, the presence of "holes" where the electrode is accessible to the solvent can result in solvent charge carriers "short circuiting" the system. However, using the present AC techniques, one or more frequencies can be chosen that prevent a frequency response of one or more charge carriers in solution, whether or not a monolayer is present. This is particularly significant since many biological fluids such as blood contain significant amounts of redox active molecules which can interfere with amperometric detection methods.

In a preferred embodiment, measurements of the system are taken at least two separate frequencies, with measurements at a plurality of frequencies being preferred. A plurality of frequencies includes a scan. For example, measuring the output signal, e.g., the AC current, at a low input frequency such as 1-20 Hz, and comparing the response to the output signal at high frequency such as 10-100 kHz will show a frequency response difference between double stranded nucleic acids with fast electron transfer rates and single stranded nucleic acids with slow electron transfer rates. In a preferred embodiment, the frequency response is determined at least two, preferably at least about five, and more preferably at least about ten frequencies.

After transmitting the input signal to initiate electron transfer, an output signal is received or detected. The presence and magnitude of the output signal will depend on the overpotential/amplitude of the input signal; the frequency of the input AC signal; the composition of the intervening medium, i.e. the impedance, between the electron transfer moieties (i.e. single stranded versus double stranded, etc.); the DC offset; the environment of the system; the nature of the second electron transfer moiety; and the solvent. At a given input signal, the presence and magnitude of the output signal will depend in general on the impedance of the medium between the two electron transfer moieties and the character of the input signal. Double stranded nucleic acids, i.e. hybridization complexes, have relatively low impedance as compared to single stranded nucleic acids, and thus result in greater output signals. However, as noted herein, single stranded nucleic acids, in the absence of the complementary target, can result in electron transfer between the electron transfer moieties. Thus, upon transmitting the input signal, comprising an AC component and a DC offset, electrons are transferred between the first electron moiety, i.e. the electrode, and the second electron moiety covalently attached to the nucleic acid, when the impedance is low enough, the frequency is in range, and the amplitude is sufficient, resulting in an output signal.

In a preferred embodiment, the output signal comprises an AC current. As outlined above, the magnitude of the output current will depend on a number of parameters. By varying these parameters, the system may be optimized in a number of ways.

In general, AC currents generated in the present invention range from about 1 femtoamp to about 1 milliamp, with currents from about 50 femtoamps to about 100 microamps being preferred, and from about 1 picoamp to about 1 microamp being especially preferred.

In a preferred embodiment, the output signal is phase shifted in the AC component relative to the input signal. Without being bound by theory, it appears that surprisingly, the systems of the present invention are sufficiently uniform to allow phase-shifting based detection. That is, the complex biomolecules of the invention through which electron transfer occurs react to the AC input in a homogeneous manner, similar to standard electronic components, such that a phase shift can be determined. This may serve as the basis of detection between single-stranded and double stranded nucleic acids, but more importantly, may allow the detection of mismatches, since small changes in impedance, such as would be assumed from a mismatch present in the hybridization complex, may effect the output AC phase in a greater manner than the frequency response.

The output signal is characteristic of electron transfer through the hybridization complex; that is, the output signal is characteristic of the presence of double stranded nucleic acid. In a preferred embodiment, the basis of the detection is a difference in the faradaic impedance of the system as a result of the formation of the hybridization complex. Faradaic impedance is the impedance of the system between the two electron transfer moieties, i.e. between the electrode and the second electron transfer moiety. Faradaic impedance is quite different from the bulk or dielectric impedance, which is the impedance of the bulk solution between the electrodes. Many factors may change the faradaic impedance which may not effect the bulk impedance, and vice versa. Thus, nucleic acids in this system have a certain faradaic impedance, that will depend on the distance between the electron transfer moieties, their electronic properties, and the composition of the intervening medium, among other things. Of importance in the methods of the invention is that the faradaic impedance between the electron transfer moieties is significantly different depending on whether the intervening nucleic acid is single stranded or double stranded. Thus, the faradaic impedance of the system changes upon the formation of a hybridization complex, and it is this change which is characteristic of the hybridization complex.

Accordingly, the present invention further provides apparatus for the detection of nucleic acids using AC detection methods. The apparatus includes a test chamber which has at least a first measuring or sample electrode, and a second measuring or counter electrode. Three electrode systems are also useful. The first and second measuring electrodes are in contact with a test sample receiving region, such that in the presence of a liquid test sample, the two electrodes may be in electrical contact.

In a preferred embodiment, the first measuring electrode comprises a single stranded nucleic acid covalently attached via a spacer, and preferably via a conductive oligomer, such as are described herein. In one embodiment, the second electron transfer moiety may be attached to the probe single stranded nucleic acid, or it may be attached to a second probe nucleic acid, the target nucleic acid, or may be added separately, for example as an intercalator. In a preferred embodiment, the second electron transfer moiety is covalently attached to the probe single stranded nucleic acid.

The apparatus further comprises an AC voltage source electrically connected to the test chamber; that is, to the measuring electrodes. Preferably, the AC voltage source is capable of delivering DC offset voltage as well.

In a preferred embodiment, the apparatus further comprises a processor capable of comparing the input signal and the output signal. The processor is coupled to the electrodes and configured to receive an output signal, and thus detect the presence of the target nucleic acid.

Thus, the compositions of the present invention may be used in a variety of research, clinical, quality control, or field testing settings.

In a preferred embodiment, the probes are used in genetic diagnosis. For example, probes can be made using the techniques disclosed herein to detect target sequences such as the gene for nonpolyposis colon cancer, the BRCA1 breast cancer gene, P53, which is a gene associated with a variety of cancers, the Apo E4 gene that indicates a greater risk of Alzheimer's disease, allowing for easy presymptomatic screening of patients, mutations in the cystic fibrosis gene, or any of the others well known in the art.

In an additional embodiment, viral and bacterial detection is done using the complexes of the invention. In this embodiment, probes are designed to detect target sequences from a variety of bacteria and viruses. For example, current blood-screening techniques rely on the detection of anti-HIV antibodies. The methods disclosed herein allow for direct screening of clinical samples to detect HIV nucleic acid sequences, particularly highly conserved HIV sequences. In addition, this allows direct monitoring of circulating virus within a patient as an improved method of assessing the efficacy of anti-viral therapies. Similarly, viruses associated with leukemia, HTLV-I and HTLV-II, may be detected in this way. Bacterial infections such as tuberculosis, chlamydia and other sexually transmitted diseases, may also be detected.

In a preferred embodiment, the nucleic acids of the invention find use as probes for toxic bacteria in the screening of water and food samples. For example, samples may be treated to lyse the bacteria to release its nucleic acid, and then probes designed to recognize bacterial strains, including, but not limited to, such pathogenic strains as, *Salmonella, Campylobacter, Vibrio cholerae*, enterotoxic strains of *E. coli*, and Legionnaire's disease bacteria. Similarly, bioremediation strategies may be evaluated using the compositions of the invention.

In a further embodiment, the probes are used for forensic "DNA fingerprinting" to match crime-scene DNA against samples taken from victims and suspects.

In an additional embodiment, the probes in an array are used for sequencing by hybridization.

The present invention also finds use as a unique methodology for the detection of mutations or mismatches in target nucleic acid sequences. As a result, if a single stranded nucleic acid containing electron transfer moieties is hybridized to a target sequence with a mutation, the resulting perturbation of the base pairing of the nucleosides will measurably affect the electron transfer rate. This is the case if the mutation is a substitution, insertion or deletion. Alternatively, two single stranded nucleic acids each with a covalently attached electron transfer species that hybridize adjacently to a target sequence may be used. Accordingly, the present invention provides for the detection of mutations in target sequences.

Thus, the present invention provides for extremely specific and sensitive probes, which may, in some embodiments, detect target sequences without removal of unhybridized probe. This will be useful in the generation of automated gene probe assays.

In an alternate embodiment the electron transfer moieties are on separate strands. In this embodiment, one single stranded nucleic acid has an electrode covalently attached via a conductive oligomer. The putative target sequences are labelled with a second electron transfer moiety as is generally described herein, i.e. by incorporating an electron transfer moiety to individual nucleosides of a PCR reaction pool. Upon hybridization of the two single-stranded nucleic acids, electron transfer is detected.

Alternatively, the compositions of the invention are useful to detect successful gene amplification in PCR, thus allowing successful PCR reactions to be an indication of the presence or absence of a target sequence. PCR may be used in this manner in several ways. For example, in one embodiment, the PCR reaction is done as is known in the art, and then added to a composition of the invention comprising the target nucleic acid with a second ETM, covalently attached to an electrode via a conductive oligomer with subsequent detection of the target sequence. Alternatively, PCR is done using nucleotides labelled with a second ETM, either in the presence of, or with subsequent addition to, an electrode with a conductive oligomer and a target nucleic acid. Binding of the PCR product containing second ETMs to the electrode composition will allow detection via electron transfer. Finally, the nucleic acid attached to the electrode via a conductive polymer may be one PCR primer, with addition of a second primer labelled with an ETM. Elongation results in double stranded nucleic acid with a second ETM and electrode covalently attached. In this way, the present invention is used for PCR detection of target sequences.

In an additional embodiment, the present invention provides novel compositions comprising metallocenes covalently attached via conductive oligomers to an electrode, such as are generally depicted in Structure 35:

Structure 35

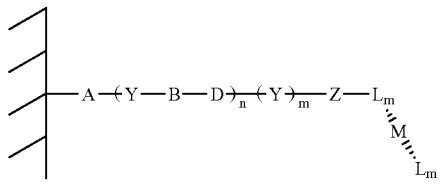

Structure 35 utilizes a Structure 4 conductive oligomer, although as will be appreciated by those in the art, other conductive oligomers such as Structures 2, 3, 9 or 10 types may be used. Preferred embodiments of Structure 35 are depicted below.

Structure 36

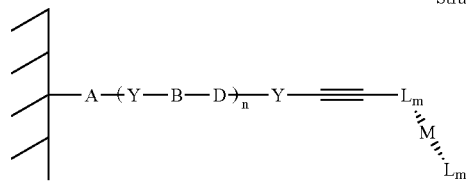

Structure 37

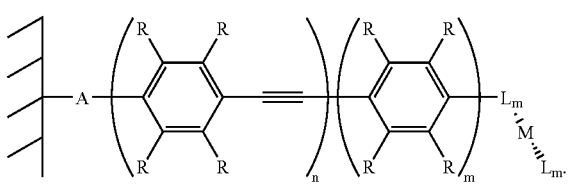

Preferred R groups of Structure 37 are hydrogen.

Structure 38

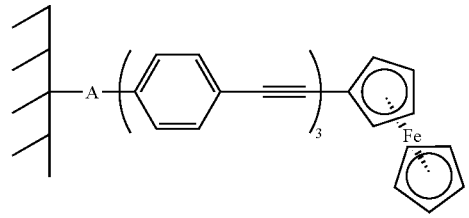

These compositions are synthesized as follows. The conductive oligomer linked to the metallocene is made as described herein; see also, Hsung et al., Organometallics 14:4808-4815 (1995); and Bumm et al., Science 271:1705 (1996), both of which are expressly incorporated herein by reference. The conductive oligomer is then attached to the electrode using the novel ethylpyridine protecting group, as outlined herein.

Once made, these compositions have unique utility in a number of applications, including photovoltaics, and infrared detection. A preferred embodiment utilizes these compounds in calibrating a potentiostat, serving as an internal electrochemistry reference in an array of the invention.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Example 1

Synthesis of Conductive Oligomer Linked Via an Amide to a Nucleoside

This synthesis is depicted in FIG. 1, using uridine as the nucleoside and a Structure 4 phenyl-acetylene conductive oligomer.

Compound #1: To a solution of 10.0 gm (40 mmol) of 4-iodothioanisole in 350 mL of dichloromethane cooled in an ice-water bath was added 10.1 gm of mCPBA. The reaction mixture was stirred for half hour and the suspension was formed. To the suspension was added 4.0 gm of powered $Ca(OH)_2$, the mixture was stirred at room temperature for 15 min and filtered off and the solid was washed once with 30 mL of dichloromethane. To the combined filtrate was added 12 mL of trifluoroacetic anhydride and the reaction mixture was refluxed for 1.5 h under Argon. After removing the solvents, the residue was dissolved in 200 mL of a mixture of TEA and methanol (ratio=50:50) and concentrated to dryness. The residue was dissolved in 100 mL of dichloromethane and the solution was washed once with 60 mL of the saturated ammonim chloride solution. The aqueous layer was extracted twice with dichloromethane (2×70 mL). The organic extracts were combined and dried over anhydrous sodium sulfate and immediately concentrated to dryness as quickly as possible. The residue was dissolved in 120 mL of benzene, followed by adding 5.3 mL of 4-vinylpyridine. The reaction mixture was refluxed under Argon overnight. The solvent was removed and the residue was dissolved in dichloromethane for column chromatography. Silica gel (150 gm) was packed with 20% ethyl acetate/hexane mixture. The crude product solution was loaded and the column was eluted with 20 to 60% ethyl acetate/hexane mixture. The fractions was identified by TLC (EtOAc:Hexane=50:50, Rf=0.24) and pooled and concentrated to dryness to afford 7.4 gm (54.2%) of the solid title compound.

Compound #2: To a solution of 3.4 gm (9.97 mmol) of Compound #1 in 70 mL of diethylamine was added 200 mg of bis(triphenylphosphine)palladium (II) chloride, 100 mg of cuprous iodide and 1.9 mL of trimethylsilylacetylene under Argon. The reaction mixture was stirred for 2 h. After removing the diethylamine, the residue was dissolved in dichloromethane for column chromatography. Silica gel (120 gm) was packed with a cosolvent of 50% ethyl acetate/50% hexane. The crude sample solution was loaded and the column was eluted with the same cosolvent. After removing the solvents, the liquid title compound (2.6 gm, 83.7%) was obtained.

Compound #3: To a solution of 2.6 gm of Compound #2 in 150 mL of dichloromethane cooled in an ice-water bath was added 9.0 mL of 1 N tetrabutylammonium fluoride THF solution. The reaction mixture was stirred for 1 h. and washed once with water and dried over anhydrous $Na_2SO_4$. After removing the solvent, the residue was used for column separation. Silica gel (50 gm) was packed with a cosolvent of 50% ethyl acetate 150% hexane. The crude product solution was loaded and the column was eluted with the same solvents. The removal of the solvents gave the solid title compound (1.87 gm, 94.1%).

Compound #4: To a glass bottle were added 1.80 gm (7.52 mmol) of Compound #3, 160 mg of bis(triphenylphosphine) palladium (II) chloride, 80 mg of cuprous iodide and 2.70 gm (9.0 mmol) of 1-trimethylsilyl-2-(4-iodophenyl)acetylene. The bottle was sealed and bubbled with Argon. Diethylamine was introduced by a syringe. The reaction mixture was heated at 50° C. under Argon for 1 h. The amine was removed and the residue was dissolved in dichloromethane for the separation. Silica gel (100 gm) was packed with 60% ethyl acetate/hexane. The crude mixture was loaded and the column was eluted with the same solvents. The fractions were identified by TLC (EtOAc:Hexane=50:50, the product emitted blue light) and pooled. The removal of the solvents gave the solid title product (2.47 gm, 79.8%).

Compound #5: To a solution of 2.47 gm of Compound #4 in 130 mL of dichloromethane cooled in an ice-water bath was added 8.0 mL of 1 N tetrabutylammonium fluoride THF solution. The reaction mixture was stirred for 1 h. and washed once with water and dried over anhydrous $Na_2SO_4$. After removing the solvent, the residue was used for column separation. Silica gel (60 gm) was packed with a cosolvent of 50% ethyl acetate/50% $CH_2Cl_2$. The crude solution was loaded and the column was eluted with the same solvents. The removal of solvents gave the solid title product (1.95 gm, 95.7%).

Compound #6: To a glass bottle were added 0.23 gm (0.68 mmol) of Compound #5, 0.5 gm (0.64 mmol) of 2'-deoxy-2'-(4-iodophenylcarbonyl) amino-5'-O-DMT uridine, 60 mg of bis(triphenylphosphine)palladium (II) chloride, 30 mg of cuprous iodide. The bottle was sealed and bubbled with Argon. Pyrrodine (15 mL) and DMF (15 mL) were introduced by a syringe. The reaction mixture was heated at 85° C. overnight. The solvents were removed in vacuo and the residue was dissolved in 300 mL of dichloromethane. The solution was washed three times with water and dried over sodium sulfate. After removing the solvent, the residue was subjected to column purification. Silica gel (30 gm) was packed with 1% TEA/1% methanol/$CH_2Cl_2$ and the sample solution was loaded. The column was eluted with 1% TEA/1% methanol/$CH_2Cl_2$ and 1% TEA/2% methanol/$CH_2Cl_2$. The fractions were identified and concentrated to dryness. The separated product was subjected to another reverse-phase column purification. Reverse-phase silica gel (C-18, 120 gm) was packed with 60% $CH_3CN$/40% $H_2O$ and the sample was dissolved in very small amount of THF and loaded. The column was eluted with 100 mL of 60% $CH_3CN$/40% $H_2O$, 100 mL of 70% $CH_3CN$/30% $H_2O$, 100 mL of 60% $CH_3CN$/10% THF/30% $H_2O$, 200 mL of 50% $CH_3CN$/20% THF/30% $H_2O$ and 500 mL of 35% $CH_3CN$/35% THF/30% $H_2O$. The fractions were identified by HPLC (0.1 mM TEAA: CH3CN=20:80, flow rate=1.0 mL/min). and concentrated to dryness to afford a pure title compound.

Compound #7: To a solution of 100 mg (0.1 mmol) of pure compound # 6 in 40 mL of pyridine were added 50 mgm of DMAP and 1.0 gm (10 mmol) of succinic anhydride. The reaction mixture was stirred under Argon for 40 h. After removing pyridine, the residue was dissolved in 300 mL of dichloromethane, followed by adding 150 mL of 5% aqueous $NaHCO_3$ solution. The mixture was vigorously stirred for 3 h and separated. The organic layer was washed once with 1% citric acid solution and dried over anhydrous sodium sulfate and concentrated to dryness to give 110 mgm of Compound #7. Without further purification, the Compound #7 was used for the preparation of the corresponding CPG.

Conductive oligomer-Uridine-CPG: To 1.4 gm of LCAA-CPG (500) in 100 mL round bottom flask were added 110 mgm (101 µmol) of the Compound #7, 100 mgm (230 µmol) of BOP reagent, 30 mgm (220 µmol) of HBT, 70 mL of dichloromethane and 2 mL of TEA. The mixture was shaken for three days. The CPG was filtered off and washed twice with dichloromethane and transferred into another 100 mL flask. Into CPG were added 50 mL of pyridine, 10 mL of acetic anhydride and 2 mL of N-methylimidazole. The CPG was filtered off, washed twice with pyridine, methanol, dichloromethane and ether, and dried over a vacuum. The loading of the nucleoside was measured according to the standard procedure to be 7.1 µmol/gm.

2'-Deoxy-2'-(4-iodophenylcarbonyl)amino-5'-O-DMT uridine: To a solution of 5.1 gm (9.35 mmol) of 2'-deoxy-2'-amino-5'-O-DMT uridine in 250 mL of pyridine cooled in an ice-water bath was added 3 mL of chlorotrimethylsilane. The reaction mixture was warmed up to room temperature and stirred for 1 h. To the prepared solution were added 0.1 gm of DMAP and 3.0 gm (10.9 mmol) 4-iodobezoyl chloride and the reaction mixture was stirred overnight. To this solution was added 30 mL of concentrated ammonium hydroxide solution and the mixture was stirred for exact 15 min. The solvents were removed in vacuo. The residue was dissolved in 15 mL of dichloromethane for column separation. Silica gel (125 gm) was packed with 1% TEA/2% $CH_3OH/CH_2Cl_2$. After loading the sample, the column was eluted with 300 mL of 1% TEA/2% $CH_3OH/CH_2Cl_2$, and 500 mL of 1% TEA/4% $CH_3OH/CH_2Cl_2$. The fractions were identified by TLC ($CH_3OH:CH_2Cl_2$=10:90) and pooled and concentrated to dryness to give 6.2 gm (85.5%) of the pure title compound.

Synthesis of the Phosphoramidite (Compound # 8).

To a solution of 0.2 gm of Compound #6 and 30 mg of diisopropylammonium tetrazolide in 10 mL of dry dichloromethane is added 0.12 gm of 2-cyanoethyl N,N, N',N'-tetraisopropylphosphane under Argon. The solution was stirred for 5 h and diluted by adding 60 mL of dichloromethane. The solution was washed twice with 2.5% w/v sodium bicarbonate solution, once with the brine and dried over sodium sulfate. After removing the solvent, residue was dissolved in 5 mL of dichloromethane, followed by adding slowly 100 mL of hexane. The suspension was stored at −20° C. for 1 h. The supernatant was decanted and the residue was dried over a high vacuum overnight to afford 0.19 gm (79.0%) of the title product, which will be used for DNA synthesis.

Example 2

Synthesis of Conductive Oligomers Linked to the Ribose of a Nucleoside Via an Amine Linkage Example 2A Synthesis of 2'-(4-iodophenyl)amino-2'-deoxy-5'-O-DMT-uridine (Product 4): This synthesis is depicted in FIG. 2, and reference is made to the labelling of the products on the figure. To a solution of 5.0 gm of 5'-O-DMT-uridine (Product 1) and 2.7 gm of dimethylaminopyridine in 200 mL of acetonitrile was added 3.3 gm of p-iodophenyl isocyalide dichloride portion by portion under Argon. The reaction mixture was stirred overnight. The mixture was diluted by adding 550 mL of dichloromethane and washed twice with 5% sodium bicarbonate aqueous solution and once with the brine solution, and then dried over sodium sulfate. The removal of the solvent in vacuo gave the crude Product 2. Without further purification, Product 2 was dissolved in 50 mL of dry DMF and the solution was heated at 150° C. foe 2 h. After distillation of DMF, the residue was dissolved in 300 mL of dichloromethane, washed once with 5% sodium bicarbonate solution, once with the brine solution and dried over sodium sulfate. The removal of the solvent gave the crude Product 3. Without purification, the Product 3 was dissolved 100 mL of a mixture of 50% Dioxane and 50% Methanol. To this solution was added 43 mL of 1N NaOH solution. The reaction mixture was stirred overnight. The mixture was diluted by adding 800 mL of dichloromethane and washed twice water and dried over $Na_2SO_4$. After removing the solvent, the residue was dissolved in 15 mL of dichloromethane for the column separation. Silica gel (100 gm) of packed with 1% TEA/ 2% Ethanol/$CH_2Cl_2$, after loading the sample solution, the column was eluted with 1% TEA/2-3% Ethanol/$CH_2Cl_2$. The fractions were identified by TLC (CH3OH:CH2Cl2=1:9) and pooled and concentrated to give 2.0 gm (29.2%) of the Product 4.

Additional conductive oligomer units can then be added to product 4 as outlined herein, with additional nucleotides added and attachment to an electrode surface as described herein.

Example 2B

Benzylamino-uridine was synthesized as shown in FIG. 16.

Synthesis of Compound C2: To a solution of 8.3 gm (15.7 mmol) of cyclonucleoside C1 in 200 mL of dichloromethane was added 2.80 gm of carbonyldiimidazole under Argon. After the solution was stirred for 7 h, into this solution were added 4.3 gm of 4-iodobenzylamine and 10 mL of diisopropylethylamine. The mixture was stirred overnight under Argon atmosphere. The solution was washed twice with 5% Citric acid solution and dried over sodium sulfate. After concentration, the residue was dissolved in a small amount of dichloromethane for the column separation. Silica gel (150 gm) was packed with 1% TEA/2% $CH_3OH/CH_2Cl_2$, upon loading the sample solution, the column was eluted with 1% TEA/2-10% $CH_3OH/CH_2Cl_2$. The fractions were identified by TLC ($CH_3OH:CH_2Cl_2$ 7:93) and pooled and concentrated to afford 9.75 gm (78.8%) of the product C2.

Synthesis of Compound C3: A mixture of 9.75 gm (12.4 mmol) of the compound C2 and 1.0 mL of DBU in 250 mL of dry THF was stirred at 50° C. under Argon for two days. THF was removed by a rotavapor and the residue was dissolved 20 mL of dichloromethane for the purification. Silica gel (130 gm) was packed with 1% TEA/25% EtOAc/$CH_2Cl_2$, after loading the sample solution, the column was eluted with same solvent mixture. The fractions containing the desired product was pooled and concentrated to give 6.46 gm (66.3%) of the product C3.

Synthesis of the Final Compound C4: The compound C3 (6.46 gm) was dissolved in a mixture of 150 mL of 1,4-dioxane and 100 mL of methanol, followed by adding 100 mL of 4.0 M aqueous sodium hydroxide. The mixture was stirred at room temperature overnight. The solution was diluted by adding 500 mL of dichloromethane and 500 mL of the brine solution. The mixture was shaken well and the organic layer was separated and washed once with the 500 mL of the brine solution and dried over sodium sulfate. The dichloromethane was removed by a rotavapor and the dioxane was removed by a high vacuum. The residue was dissolved in 20 mL of dichloromethane for the separation. Silica gel (80 gm) was packed with 1% TEA/25% EtOAc/$CH_2Cl_2$ and the sample solution was loaded. The column was eluted with 1% TEA/25-50% EtOAc/$CH_2Cl_2$. The right fractions were combined and concentrated to give 4.1 gm (65.7%) of the final product C4.

Example 3

Synthesis of a Conductive Oligomer with an R Group Attached to the Y Aromatic Group This synthesis is depicted in FIG. 6.

Synthesis of 2-Acetyl-5-iodotoluene (P 1). To a suspension of 20 gm of aluminum trichloride in 500 mL of dichloromethane was added 10.2 mL of acetyl chloride under Argon. After the reaction mixture was stirred for 15 min, 3-iodotoluene (20 gm) was added through a syringe. The mixture was stirred overnight under Argon and poured into 500 gm of ice-water. Organic layer was separated and washed once with the saturated ammonium chloride solution, and washed once with 10% sodium thiosulfate solution and dried over sodium sulfate. After removing the solvent, the residue was dissolved in hexane for the column purification. Silica gel (260 gm) was packed with hexane, after loading the sample solution, the column was eluted with 750 mL of hexane, 750 mL of 1% v/v ether/hexane, 750 mL of 2% v/v ether/hexane and 1500 mL of 3% v/v ether/hexane. The fractions containing the right isomer were identified by GC-MS and $^1$H NMR and pooled and concentrated to dryness to afford 12.2 gm (51.2%) of the title product (P 1).

Iodo-3-methyl-4-(ehynyl trimethylsilyl)benzene (P2). Under inert atmosphere 500 ml bound bottom flask was charged with 25 ml of dry THF, cooled to −78° C. and 14 ml of 2.0 M LDA solution (heptane/ethylbenzene/THF solution) was added by syringe. To this solution 6.34 gr (24.38 mmole) of iodo-3-methyl-4-acetyl benzene in 25 ml of THF was added dropwise and the reaction mixture was stirred for 1 hr at −78° C., then 4.0 ml (19.42 mmole) of diethychlorophosphate were added by syringe. After 15 min cooling bath was removed and the reaction mixture was allowed to heat up to RT and stirred for 3 hrs. The resulted mixture was cooled again to −78° C. and 29 ml of 2.0 M LDA solution were added dropwise. At the end of the addition the reaction mixture was allowed to warm up to RT and stirred for additional 3 hrs. After that period of time it was cooled again to −20° C., 9.0 ml (70.91 mmole) of trimethylsilyl chloride were injected and the stirring was continued for 2 hrs at RT. The reaction mixture was poured into 200 ml of ice/sodium bicarbonate saturated aqueous solution and 300 ml of ether were added to extract organic compounds. The aqueous phase was separated and extracted again with 2×100 ml of ether. The ether fractions were combined, dried over sodium sulfate and evaporated. The resulted liquid residue was purified by silica gel chromatography (100% n-hexane as eluent). 4.1 gr (54% yield) were obtained.

Synthesis of Product (P 3). To a solution of 1.14 gm of Compound #3 (as described above) and 1.60 gm of P 2 in 100 mL of diethylamine were added 0.23 gm of [1,1'-bis(diphenylphosphino)ferrocene]palladium (II) chloride and 0.1 gm of copper (I) iodide under Argon. The reaction mixture was stirred at 55° C. for 1 h and stirred at room temperature overnight. After removing the solvent, the residue was dissolved in dichloromethane for column separation. Silica gel (120 gm) was packed with 20% ethyl acetate/$CH_2Cl_2$. The sample solution was loaded and the column was eluted with 20-50% ethyl acetate/$CH_2Cl_2$. The fractions were identified by TLC (EtOAC: CH2Cl2=50: 50) and pooled and concentrated to give 1.70 gm (84.0%) of TMS-derivative of P 3.

To a solution of 0.74 gm of TMS-derivative of P 3 in 70 mL of dichloromethane at 0° C. was added 2.2 mL of 1.0 M (nBu)$_4$NF THF solution. After stirring for 30 min, the solution was washed once with water and dried over sodium sulfate. The solvent was removed, the residue was used for column separation. Silica gel (20 gm) was packed with 20% ethyl acetate/CH$_2$Cl$_2$, the column was eluted with 20-40% ethyl acetate/CH$_2$Cl$_2$. The fractions containing the fluorescent compound were combined and concentrated to dryness to afford 0.5 gm (81.3%) of the pure P 3.

Synthesis of P 4: To a solution of 0.5 gm of P 3 and 0.63 gm of P 2 in 50 mL of dry DMF and 10 mL of TEA were added 100 mgm of [1,1'-bis(diphenylphosphino)ferrocene]palladium (II) chloride and 50 mgm of copper (I) iodide under Argon. The reaction mixture was stirred at 55° C. for 1 h and stirred at 35° C. overnight. The solvents were removed in vacuo and the residue was dissolved in 10 mL of CH$_2$Cl$_2$ for column separation. Silica gel (100 gm) was packed with 20% ethyl acetate/CH$_2$Cl$_2$, after loading the sample, the column was eluted with 20-40% ethyl acetate/CH$_2$Cl$_2$. The fractions were identified by TLC (EtOAC:CH$_2$Cl$_2$=50:50) and pooled and concentrated to give 0.47 gm (61.3%) of TMS-derivative of P 4.

To a solution of 0.47 gm of TMS-derivative of P 4 in 70 mL of dichloromethane at 0° C. was added 1.0 mL of 1.0 M (nBu)$_4$NF THF solution. After stirring for 30 min, the solution was washed once with water and dried over sodium sulfate. The solvent was removed, the residue was used for column separation. Silica gel (20 gm) was packed with 20% ethyl acetate/CH$_2$Cl$_2$, the column was eluted with 20-40% ethyl acetate/CH$_2$Cl$_2$. The fractions containing the fluorescent compound were combined and concentrated to dryness to afford 0.32 gm (78.7%) of the pure P 4.

Other conductive oligomers with R groups are depicted in FIG. 17, which were made using the techniques outlined herein.

Example 4

Synthesis of a Nucleoside with a Metallocene Second Electron Transfer Moiety Attached Via a Ribose Synthesis of 5'-O-DMT-2'-deoxy-2'-(ferrocenecarbonyl) amino Uridine (UAF): To a solution of 2.5 gm (10.9 mmol) of ferrocene monocarboxylic acid in 350 mL of dichloromethane were added 2.25 gm (10.9 mmol) of DCC and 1.27 gm (10.9 mmol) of N-hydroxysuccinimide. The reaction mixture was stirred for 3 h and the precipitate was formed. The precipitate was filtered off and washed once with dichloromethane. The combined filtrate was added into 4.5 gm (8.25 mmol) of 2'-deoxy-2'-amino-5'-O-DMT uridine, followed by adding 2 mL of triethylamine. The reaction mixture was stirred at room temperature for 8 days. After removing the solvent, the residue was dissolved in dichloromethane for separation. Silica gel (120 gm) was packed with 1% TEA/2% CH$_3$OH/CH$_2$Cl$_2$. After loading the sample solution, the column was eluted with 2-7% CH$_3$OH/1% TEA/CH$_2$Cl$_2$. The fraction was identified by TLC(CH$_3$OH:CH$_2$Cl$_2$=1:9) and pooled and concentrated to dryness to afford 1.3 gm (22.0%) of the title compound.

Synthesis of UAF Phosphoramidite:

Preparation of Diisopropylaminochloro(β-cyano)ethoxyphosphine: To a solution of 0.54 mL (4.0 mmol) of dichloro (β-cyano)ethoxyphosphine in 40 mL of dichloromethane cooled in an ice-water bath was added 10 mL of diisopropylethylamine, followed by adding 0.64 mL (4.0 mmol) of diisopropylamine under Argon. The reaction mixture was warmed up to room temperature and stirred for 2 h. After adding 0.1 gm of DMAP into the solution, the reaction mixture is ready for the next step reaction.

Preparation of UAF phosphoramidite: To a solution of 1.30 gm (1.72 mmol) of 5'-O-DMT-5-ferrocenylacetylenyl-2'-deoxy uridine in 40 mL of dichloromethane cooled in an ice-water bath was added 10 mL of diisopropylethylamine. The prepared phosphine solution was transferred into the nucleoside solution through a syringe. The reaction mixture was warmed up to room temperature and stirred overnight. The solution was diluted by adding 100 mL of dichloromethane and washed once with 200 mL od 5% aqueous NaHCO$_3$ solution, and once with the brine (200 mL) and dried over Na$_2$SO$_4$ and concentrated to dryness. Silica gel (47 gm) was packed with 2% TEA/1% CH$_3$OH/CH$_2$Cl$_2$. The residue was dissolved in 10 mL of dichloromethane and loaded. The column was eluted with 150 mL of 1% TEA/1% CH$_3$OH/ CH$_2$Cl$_2$ and 250 mL of 1% TEA/2% CH$_3$OH/CH$_2$Cl$_2$. The fractions were pooled and concentrated to give 0.5 gm (30.3%) of the title compound.

Nucleotides containing conductive oligomers and second electron transfer moieties were incorporated into nucleic acids using standard nucleic acid synthesis techniques; see "Oligonucleotides and Analogs, A Practical Approach", Ed. By F. Eckstein, Oxford University Press, 1991, hereby incorporated by reference.

Example 5

Synthesis of a Nucleoside with a Metallocene Second Electron Transfer Moiety Attached Via the Base Synthesis of 5'-O-DMT-5-ferrocenylacetylenyl-2'-deoxy uridine (UBF): In a flask were added 4.8 gm (13.6 mmol) of 5-iodo-2'-deoxy uridine, 400 mg of bis(triphenylphosphine) palladium (II) chloride, 100 mg of cuprous iodide, 95 mL of DMF and 10 mL of TEA. The solution was degassed by Argon and the flask was sealed. The reaction mixture was stirred at 50° C. overnight. After removing solvents in vacuo, the residue was dissolved in 140 mL of dry pyridine, followed by adding 0.2 gm of DMAP and 5.0 gm (14.8 mmol) of DMT-Cl. The reaction mixture was stirred at RT overnight. After removing the solvent, the residue was dissolved in 300 mL of dichlormethane and washed twice with 5% aqueous NaHCO$_3$ (2×200 mL), twice with the brine (2×200 mL) and dried over sodium sulfate. The solvent was removed and the residue was coevaporated twice with toluene and dissolved in 15 mL of dichloromethane for column separation. Silica gel (264 gm) was packed 0.5% TEA/CH$_2$Cl$_2$. After loading the crude product solution, the column was eluted with 300 mL of 1% TEA/2% CH$_3$OH/CH$_2$Cl$_2$, 400 mL of 1% TEA/5% CH$_3$OH/CH$_2$Cl$_2$, and 1.2 L of 1% TEA/7% CH$_3$OH/CH$_2$Cl$_2$. The fractions were identified by TLC(CH$_3$OH:CH$_2$Cl$_2$=10: 90) and pooled and concentrated to dryness to give 7.16 gm (71.3%) of the title compound.

Synthesis of UBF Phosphoramidite:

Preparation of Diisopropylaminochloro(β-cyano)ethoxyphosphine: To a solution of 1.9 mL (13.8 mmol) of dichloro (β-cyano)ethoxyphosphine in 40 mL of dichloromethane cooled in an ice-water bath was added 10 mL of diisopropylethylamine, followed by adding 2.3 mL (13.8 mmol) of diisopropylamine under Argon. The reaction b mixture was warmed up to room temperature and stirred for 2 h. After adding 0.1 gm of DMAP into the solution, the reaction mixture is ready for next step reaction.

Preparation of UBF phosphoramidite: To a solution of 3.42 gm (4.63 mmol) of 5'-O-DMT-5-ferrocenylacetylenyl-2'-deoxy uridine in 40 mL of dichloromethane cooled in an ice-water bath was added 10 mL of diisopropylethylamine. The prepared phosphine solution was transferred into the nucleoside solution through a syringe. The reaction mixture was warmed up to room temperature and stirred overnight. The solution was diluted by adding 150 mL of dichloromethane and washed once with 200 mL of 5% aqueous $NaHCO_3$ solution, and once with the brine (200 mL) and dried over $Na_2SO_4$ and concentrated to dryness. Silica gel (92 gm) was packed with 2% TEA/1% $CH_3OH/CH_2Cl_2$. The residue was dissolved in 10 mL of dichloromethane and loaded. The column was eluted with 500 mL of 1% TEA/2% $CH_3OH/CH_2Cl_2$. The fractions were pooled and concentrated to give 3.0 gm (69.0%) of the title compound.

Nucleotides containing conductive oligomers and second electron transfer moieties were incorporated into nucleic acids using standard nucleic acid synthesis techniques; see "Oligonucleotides and Analogs, A Practical Approach", Ed. By F. Eckstein, Oxford University Press, 1991, hereby incorporated by reference.

Example 6

Synthesis of an Electrode Containing Nucleic Acids Containing Conductive Oligomers with a Monolayer of $(CH_2)_{16}$ Using the above techniques, and standard nucleic acid synthesis, the uridine with the phenyl-acetylene conductive polymer of Example 1 was incorporated at the 3' position to form the following nucleic acid: ACCATGGACTCAGCU (SEQ ID NO: 1)-conductive polymer of Example 1 (hereinafter "wire-1").

HS—(CH2)16-OH (herein "insulator-2") was made as follows.

16-Bromohexadecanoic acid. 16-Bromohexadecanoic acid was prepared by refluxing for 48 hrs 5.0 gr (18.35 mmole) of 16-hydroxyhexadecanoic acid in 24 ml of 1:1 v/v mixture of HBr (48% aqueous solution) and glacial acetic acid. Upon cooling, crude product was solidified inside the reaction vessel. It was filtered out and washed with 3×100 ml of cold water. Material was purified by recrystallization from n-hexane, filtered out and dried on high vacuum. 6.1 gr (99% yield) of the desired product were obtained.

16-Mercaptohexadecanoic acid. Under inert atmosphere 2.0 gr of sodium metal suspension (40% in mineral oil) were slowly added to 100 ml of dry methanol at 0° C. At the end of the addition reaction mixture was stirred for 10 min at RT and 1.75 ml (21.58 mmole) of thiolacetic acid were added. After additional 10 min of stirring, 30 ml degassed methanolic solution of 6.1 gr (18.19 mmole) of 16-bromohexadecanoic acid were added. The resulted mixture was refluxed for 15 hrs, after which, allowed to cool to RT and 50 ml of degassed 1.0 M NaOH aqueous solution were injected. Additional refluxing for 3 hrs required for reaction completion. Resulted reaction mixture was cooled with ice bath and poured, with stirring, into a vessel containing 200 ml of ice water. This mixture was titrated to pH=7 by 1.0 M HCl and extracted with 300 ml of ether. The organic layer was separated, washed with 3×150 ml of water, 150 ml of saturated NaCl aqueous solution and dried over sodium sulfate. After removal of ether material was purified by recrystallization from n-hexane, filtering out and drying over high vacuum. 5.1 gr (97% yield) of the desired product were obtained.

16-Bromohexadecan-1-ol. Under inert atmosphere 10 ml of $BH_3$.THF complex (1.0 M THF solution) were added to 30 ml THF solution of 2.15 gr (6.41 mmole) of 16-bromohexadecanoic acid at −20° C. Reaction mixture was stirred at this temperature for 2 hrs and then additional 1 hr at RT. After that time the resulted mixture was poured, with stirring, into a vessel containing 200 ml of ice/saturated sodium bicarbonate aqueous solution. Organic compounds were extracted with 3×200 ml of ether. The ether fractions were combined and dried over sodium sulfate. After removal of ether material was dissolved in minimum amount of dichloromethane and purified by silica gel chromatography (100% dichloromethane as eluent). 1.92 gr (93% yield) of the desired product were obtained.

16-Mercaptohexadecan-1-ol. Under inert atmosphere 365 mg of sodium metal suspension (40% in mineral oil) were added dropwise to 20 ml of dry methanol at 0° C. After completion of addition the reaction mixture was stirred for 10 min at RT followed by addition of 0.45 ml (6.30 mmole) of thiolacetic acid. After additional 10 min of stirring 3 ml degassed methanolic solution of 1.0 gr (3.11 mmole) of 16-bromohexadecan-1-ol were added. The resulted mixture was refluxed for 15 hrs, allowed to cool to RT and 20 ml of degassed 1.0 M NaOH aqueous solution were injected. The reaction completion required additional 3 hr of reflux. Resulted reaction mixture was cooled with ice bath and poured, with stirring, into a vessel containing 200 ml of ice water. This mixture was titrated to pH=7 by 1.0 M HCl and extracted with 300 ml of ether. The organic layer was separated, washed with 3×150 ml of water, 150 ml of saturated NaCl aqueous solution and dried over sodium sulfate. After ether removal material was dissolved in minimum amount of dichloromethane and purified by silica gel chromatography (100% dichloromethane as eluent). 600 mg (70% yield) of the desired product were obtained.

A clean gold covered microscope slide was incubated in a solution containing 100 micromolar HS—$(CH_2)_{16}$—COOH in ethanol at room temperature for 4 hours. The electrode was then rinsed thoroughly with ethanol and dried. 20-30 microliters of wire-1 solution (1 micromolar in 1×SSC buffer at pH 7.5) was applied to the electrode in a round droplet. The electrode was incubated at room temperature for 4 hours in a moist chamber to minimize evaporation. The wire-1 solution was then removed from the electrode and the electrode was immersed in 1×SSC buffer followed by 4 rinses with 1×SSC. The electrode was then stored at room temperature for up to 2 days in 1×SSC.

Alternatively, and preferably, either a "two-step" or "three-step" process is used. The "two-step" procedure is as follows. The wire-1 compound, in water at ~5-10 micromolar concentration, was exposed to a clean gold surface and incubated for ~24 hrs. It was rinsed well with water and then ethanol. The gold was then exposed to a solution of ~100 micromolar insulator thiol in ethanol for ~12 hrs, and rinsed well. Hybridization was done with complement for over 3 hrs. Generally, the hybridization solution was warmed to 50° C., then cooled in order to enhance hybridization.

The "three-step" procedure uses the same concentrations and solvents as above. The clean gold electrode was incubated in insulator solution for ~1 hr and rinsed. This procedure presumably results in an incomplete monolayer, which has areas of unreacted gold. The slide was then incubated with wire-1 solution for over 24 hrs (generally, the longer the better). This wire-1 still had the ethyl-pyridine protecting group on it. The wire-1 solution was 5% NH4OH, 15% ethanol in water. This removed the protecting group from the wire and allowed it to bind to the gold (an in situ deprotection). The slide was then incubated in insulator again for ~12 hrs, and hybridized as above.

In general, a variety of solvent can be used including water, ethanol, acetonitrile, buffer, mixtures etc. Also, the input of energy such as heat or sonication appears to speed up all of the deposition processes, although it may not be necessary. Also, it seems that longer incubation periods for the wire-1 addition step, for example as long as a week, the better the results.

Hybridization efficiency was determined using $^{32}P$ complementary and noncomplementary 15 mers corresponding to the wire-1 sequence. The electrodes were incubated with 50 microliters of each of the labelled non-complementary (herein "A5") or complementary (herein "S5") target sequences applied over the entire electrode in 1×SSC as depicted in Table 1. The electrodes were then incubated for 1-2 hours at room temperature in a moist chamber, and rinsed as described above. The amount of radiolabelled DNA was measured for each electrode in a scintillation counter, and the electrodes were dried and exposed to X-ray film for 4 hours.

TABLE 1

| hybridized with: | total $^{32}P$ counts added | $^{32}P$ counts hybridized to surface |
|---|---|---|
| A5, 20% specific activity, DNA concentration 1 nM, 1 hour incubation | 46,446 | 152 |
| S5, 30% specific activity, DNA concentration 1 nM, 1 hour incubation | 39,166 | 10,484 (27% hybridized) |
| A5, 14% specific activity, DNA concentration 5 nM, 2 hour incubation | 182,020 | 172 |
| S5, 20% specific activity, DNA concentration 5 nM, 2 hour incubation | 96,284 | 60,908 (63% hybridized) |

Example 7

Synthesis of Compositions Containing Ferrocene Linked to an Electrode

It has been shown in the literature that cyclic voltametry can be used to determine the electron transfer rate of surface bound molecules. Surface bound molecules should show perfectly symmetric oxidation and reduction peaks if the scan speed of the voltammagram is sufficiently slow. As the scan rate is increased, these peaks are split apart due to the kinetics of electron transfer through the molecules. At a given scan speed, a poorly conducting molecule should exhibit greater splitting than a good conductor. As the speed is increased, the poor conductor will be split even more.

Accordingly, to test the conductivity of the conductive polymer as compared to a traditional insulator, two molecules were tested. The synthesis of ferrocene attached via a conductive oligomer to an electrode (herein "wire-2") was made as follows, as depicted in FIG. 7.

Synthesis of compound #11 was as follows. 2.33 gr (5.68 nmole) of compound #10 (made as described in Hsung et al., Organometallics 14:4808-4815 (1995), incorporated by reference), 90 mg (0.47 mmole) of CuI and 80 mg (0.11 mmole) of $PdCl_2(PPh_3)_2$ were dissolved in 100 ml of pyrrolidine under inert atmosphere and heated for 20 hrs at 50° C. All volatile components were removed on high vacuum and resulted crude residue was dissolved in minimum amount of dichloromethane. The desired compound was purified by silica gel chromatography (50% ethyl acetate+50% dichloromethane as eluent). 3.2 gr (90% yield) of the pure product were obtained.

Compound #12. To 200 mg (0.32 mmole) of suspension of MG#1 in 200 ml of acetone (sonication was applied in order to get better results) 3 ml of MeI were added and the reaction mixture was stirred for 20 hrs at RT. After that time volume of the resulted solution was reduced by rotovap evaporation to 50 ml and then 400 ml of n-hexane were added. Formed precipitate was filtered out, washed with 3×200 ml of n-hexane and dried on high vacuum. Quantitative yield of the desired compound was obtained.

Compound #13. To 100 mg (0.13 mmole) of suspension of MG#2 in 200 ml of acetone (sonication was applied in order to get better results) 10 ml of triethyl amine were added and the reaction mixture was stirred for 20 hrs at RT. After that time volume of the resulted solution was reduced by rotovap evaporation to 50 ml and then 400 ml of n-hexane were added. Formed precipitate was filtered out, washed with 3×200 ml of n-hexane and dried on high vacuum. The desired compound was extracted from this precipitate with 3×50 ml of THF. Evaporation of the THF fractions gave 35 mg (52%) of the compound #13. This was then added to a gold electrode as known in the art.

HS—(CH2)15NHCO-Fc (herein "insulator-1") was made as described in Ward et al., Anal. Chem. 66:3164-3172 (1994), hereby incorporated by reference (note: the FIG. 1 data has been shown to be incorrect, although the synthesis of the molecule is correct).

Monolayers of each were made as follows. Insulator: Gold covered microscope slides were immersed in a mixture of insulator-1 and HS—(CH2)15-OH (insulator-2) in neat ethanol. Insulator-2 molecule is added to the mixture to prevent the local concentration of ferrocene at any position from being too high, resulting in interactions between the ferrocene molecules. The final solution was 0.1 mM insulator-1 and 0.9 mM insulator-2. The mixture was sonicated and heated (60-80° C.) for 1-10 hours. The electrodes were rinsed thoroughly with ethanol, water and ethanol. The electrodes were immersed in a 1 mM thiol solution in neat ethanol and let stand at room temperature for 2-60 hours. The electrodes were then rinsed again. This procedure resulted in 1-10% coverage of insulator-1 as compared to calculated values of close packed ferrocene molecules on a surface. More or less coverage could easily be obtained by altering the mixture concentration and/or incubation times.

Wires: The same procedure was followed as above, except that the second step coating required between 10 and 60 hours, with approximately 24 hours being preferable. This resulted in lower coverages, with between 0.1 and 3% occurring.

Cyclic voltametry was run at 3 scan speeds for each compound: 1 V/sec, 10 V/ec, and 50 V/sec. Even at 1 V/sec, significant splitting occurs with insulator-1, with roughly 50 mV splitting occuring. At higher speeds, the splitting increases. With wire-2, however, perfectly symmetrical peaks are observed at the lower speeds, with only slight splitting occurring at 50 V/sec.

It should be noted that despite a significant difference in electron transfer rate, electron transfer does still occur even in poorly conducting oligomers such as $(CH_2)_{15}$, traditionally called "insulators". Thus the terms "conductive oligomer" and "insulator" are somewhat relative.

Example 8

Synthesis and Analysis of Nucleic Acid with Both a Conductive Oligomer and a Second Electron Transfer Moiety The following nucleic acid composition was made using the techniques above: 5'-ACCATGGAC[UBF]CAGCU(SEQ ID NO:2)-conductive polymer (Structure 5 type, as outlined above) herein "wire-3", with UBF made as described above. Thus, the second electron transfer moiety, ferrocene, is on the sixth base from the conductive oligomer.

Mixed monolayers of wire-3 and insulator-2 were constructed using the techniques outlined above. The compositions were analyzed in 0.2 M $NaClO_4$ in water using cyclic voltametry (CV) and square wave voltametry (SW), in the absence (i.e. single stranded) and presence (i.e. double stranded) of complementary target sequence.

The results of SW show the absence of a peak prior to hybridization, i.e. in the absence of double stranded nucleic acid. In the presence of the complementary target sequence, a peak at ~240 mV, corresponding to ferrocene, was seen.

A mediator as described herein was also used. 6 mM ferricyanide ($Fe(CN)_6$) was added to the solution. Ferricyanide should produce a peak at 170 mV in a SW experiment. However, no peak at 170 mV was observed, but the peak at 240 mV was greatly enhanced as compared to the absence of ferricyanide.

Alternatively, CV was done. No peaks were observed in the absence of target sequence. Once again, the chip was incubated with perfectly complimentary nucleic acid in order to hybridize the surface nucleic acid. Again, the chip was scanned under the same conditions. An increased signal was observed. Finally, the chip was soaked in buffer at 70° C. in order to melt the compliment off the surface. Previous experiments with radioactive probes have shown that 15-mers hybridized on a very similar surface melted at approximately 45° C. Repeating the scan after the heat treatment shows a reduced signal, as in the first scan prior to hybridization.

Example 9

AC Detection Methods

Electrodes containing four different compositions of the invention were made and used in AC detection methods. In general, all the electrodes were made by mixing a ratio of insulator-2 with the sample as is generally outlined above.

Sample 1, labeled herein as "Fc-alkane", contained a mixed monolayer of insulator-2 and insulator-1. Sample 2, labeled herein as "Fc-amido-alkane", contained a mixed monolayer of insulator-2 and a derivative of insulator-1 which has an amido attachment of the ferrocene to the alkane. Sample 3, labeled herein as "Fc-wire", contained a mixed monolayer of insulator-2 and wire-2. Sample 4 was the same as Sample 3, with the exception that a new in situ deprotection step was used, described below. Sample 5, labeled herein as "ssDNA", contained a mixed monolayer of insulator-2 and wire-3.

Sample 6, labeled herein as "dsDNA", contained a mixed monolayer of insulator-2 and wire-3, wherein the complement of wire-3 was hybridized to form a double stranded wire-3. Sample 7 was a solution of ferrocene in solution. As is shown herein, the rate of electron transfer, from fast to slower, is as follows: Sample 3>Sample 5>Sample 1>Sample 4. Generally, Sample 1 models ssDNA, and Sample 3 models dsDNA.

The experiments were run as follows. A DC offset voltage between the working (sample) electrode and the reference electrode was swept through the electrochemical potential of the ferrocene, typically from 0 to 500 mV. On top of the DC offset, an AC signal of variable amplitude and frequency was applied. The AC current at the excitation frequency was plotted versus the DC offset.

FIG. 8 depicts an experiment with Sample 1, at 200 mV AC amplitude and frequencies of 1, 5 and 100 Hz. Sample 1 responds at all three frequencies, and higher currents result from higher frequencies, which is simply a result of more electrons per second being donated by the ferrocene at higher frequencies. The faster the rate, the higher the frequency response, and the better the detection limit. FIG. 9 shows overlaid AC voltammograms of an electrode coated with Sample 3. Four excitation frequencies were applied: 10 Hz, 100 Hz, 1 kHz, 10 kHz, all at 25 mV overpotential. FIG. 10, shows the frequency response of the system by measuring the peak currents. Sample 3 response to increasing frequencies through 10 kHz (the detector system limit), while Sample 1 lose its responses at between 20 and 200 Hz. Thus, to discriminate between Sample 1 and Sample 3, one would only have to analyze it at 1 Hz and 1000 Hz and compare the responses. This should be similar to the dsDNA and ssDNA system. FIG. 11 shows Sample 5 and Sample 6, plotted as a function of normalized current (with the highest current being 1 for both cases; the actual current of dsDNA is much higher than that of ssDNA, so the graph was normalized to show both). The lines are modeled RC circuits, as described above, and not a fit to the data. At 1 Hz, both ssDNA and dsDNA respond; at 200 Hz, the ssDNA signal is gone. FIG. 12 shows that increasing the overpotential will increase the output signal. FIGS. 13A and 13B show that the overpotential and frequency can be tuned to increase the selectivity and sensitivity. For example, a low overpotential and high frequence can be used to minimize the slower species (Sample 1 or Sample 5). Then the overpotential can be increased to induce a response in the slower species for calibration and quantification.

FIG. 14 shows that the ferrocene added to the solution (Sample 7) has a frequency response related to diffusion that is easily distinguishable from the frequency response of attached ferrocene. This indicates that by varying frequency, signals from bound molecules, particular fast bound molecules such as dsDNA, can be easily distinguished from any signal generated by contaminating redox molecules in the sample.

FIGS. 15A and 15B shows the phase shift that results with different samples. FIG. 15A shows the model compounds, and 15B shows data with dsDNA and ssDNA. While at this frequency, the phase shift is not large, a frequency can always be found that results in a 90° shift in the phase.

Example 10

Synthesis of Conductive Oligomers Attached Via a Base

Figure 19B:
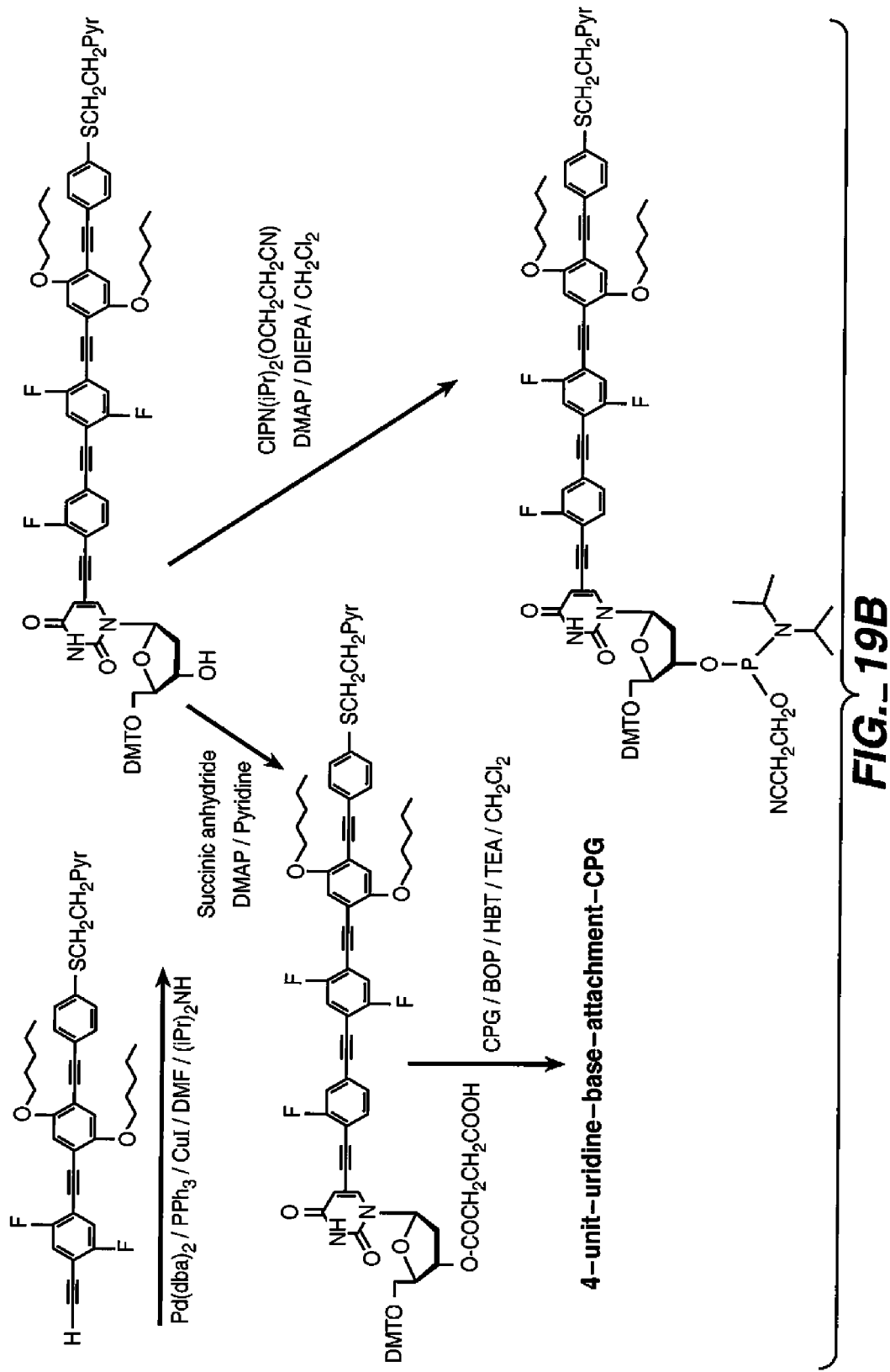
FIG. 19 depicts a synthetic scheme for a four unit conductive oligomer attached to the base.

Representative syntheses are depicted in FIGS. 18 and 19. When using palladium coupling chemistry, it appears that protecting groups are required on the base, in order to prevent significant dimerization of conductive oligomers instead of coupling to the iodinated base. In addition, changing the components of the palladium reaction may be desirable also. Also, for longer conductive oligomers, R groups are preferred to increase solubility.

Example 11

The Use of Trimethylsilylethyl Protecting Groups

The use of an alternate protecting group for protection of the sulfur atom prior to attachment to the gold surface was explored.

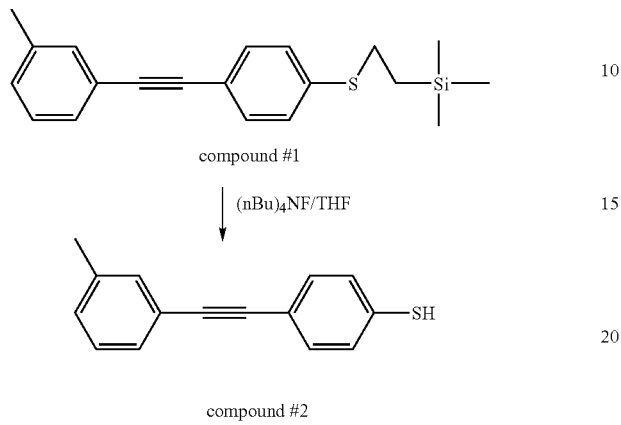

compound #1

↓ (nBu)₄NF/THF compound #2

To 0.5 gm of molecular sieve (3 Å) was added 3 ml of dry THF and 2.5 ml of 1.0 tetrabutylammonium fluoride. After stirring for 20 minutes, 100 mg of compound #1 was added under Argon. The reaction mixture was stirred for 1 hour and poured into 100 ml of 5% citric acid solution and the aqueous solution was shaken well and extracted twice with either (2×100 ml). The combined ether solution was dried over $Na_2SO_4$ and concentrated. The residue was purified by column chromatography using 10% $CH_2Cl_2$/Hexane as eluent. The purified product was analyzed by ¹HNMR which should 50% of compound #2 and 50% of the corresponding disulfide.

Figure 20B:
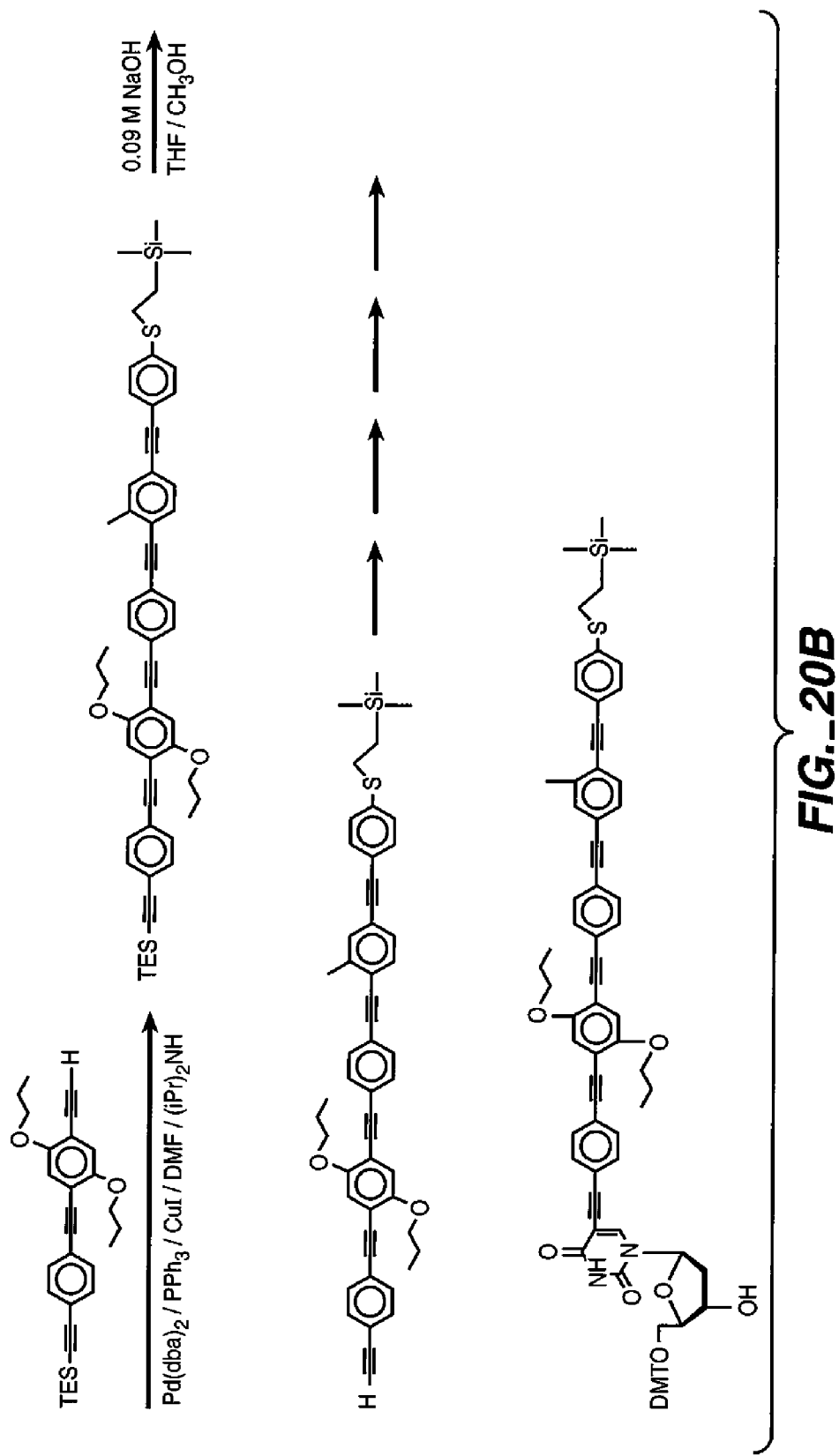
FIG. 20 depicts the use of a trimethylsilylethyl protecting group in synthesizing a five unit wire attached via the base.

The use of this protecting group in synthesizing base-attached conductive oligomers is depicted in FIGS. 20 and 21.

We claim:

1. An apparatus for the detection of target nucleic acids in a test sample, comprising:
   a) a test chamber comprising a first and a second electrode, wherein said first electrode comprises:
      i. a single stranded nucleic acid covalently attached to said electrode via an insulator, wherein said insulator is an alkyl oligomer wherein each monomer of said alkyl oligomer is independently selected from the group consisting of: —$(CH_2)_n$—, —$(CRH)_n$—, —$(CR2)_n$—, ethylene glycol and ethylene glycol derivatives using other heteroatoms in place of oxygen; wherein n is from 1 to 16; and wherein R is selected from the group consisting of hydrogen, alkyl, alcohol, aromatic amino, amido, nitro, ethers, esters, aldehydes, sulfonyl, silicon moieties, halogens, sulfur containing moieties, phosphorous containing moieties, and
      ii. a passivation agent monolayer; and
   b) an AC/DC voltage source electrically connected to said first and second electrodes.

2. An apparatus accordingly to claim 1 further comprising,
   c) a second nucleic acid covalently attached to an electron transfer moiety.

3. An apparatus for the detection of target nucleic acids in a test sample, comprising:
   a) a test chamber comprising a first and a second electrode, wherein said first electrode comprises:
      i. a covalently attached single stranded nucleic acid attached to said first electrode via an insulator, wherein said insulator is an alkyl oligomer wherein each monomer of said alkyl oligomer is independently selected from the group consisting of: —$(CH_2)_n$—, —$(CRH)_n$—, ethylene glycol and ethylene glycol derivatives using other heteroatoms in

SEQUENCE LISTING

```
<160> NUMBER OF SEQ ID NOS:  2

<210> SEQ ID NO 1
<211> LENGTH: 20
<212> TYPE: DNA
<213> ORGANISM: Artificial Sequence
<220> FEATURE:
<223> OTHER INFORMATION: Description of Combined DNA/RNA Molecule:
      Combined
<223> OTHER INFORMATION: Description of Artificial Sequence: Synthetic

<400> SEQUENCE: 1
accatggact ggactcagcu                                                 20

<210> SEQ ID NO 2
<211> LENGTH: 14
<212> TYPE: DNA
<213> ORGANISM: Artificial Sequence
<220> FEATURE:
<223> OTHER INFORMATION: Description of Combined DNA/RNA Molecule:
      Combined
<223> OTHER INFORMATION: Description of Artificial Sequence:  Synthetic

<400> SEQUENCE: 2
accatggacc agcu                                                       14
``` place of oxygen; wherein n is from 1 to 16; and wherein R is selected from the group consisting of hydrogen, alkyl alcohol, aromatic amino, amido, nitro, ethers, esters, aldehydes, sulfonyl, silicon moieties, halogens, sulfur containing moieties, phosphorous containing moieties;

ii. a passivation agent monolayer; and iii. a covalently attached first electron transfer moiety; and b) an AC/DC voltage source electrically connected to said test chamber.

4. An apparatus for the detection of target nucleic acids in a test sample, comprising:

a. a test chamber comprising a first and a second electrode, wherein said first electrode comprises:

i. a covalently attached first single stranded nucleic acid attached to said first electrode via an insulator, wherein said insulator is an alkyl oligomer wherein each monomer of said alkyl oligomer is independently selected from the group consisting of: $-(CH_2)_n-$, $-(CRH)_n-$, $-(CR2)_n-$, ethylene glycol and ethylene glycol derivatives using other heteroatoms in place of oxygen; wherein n is from 1 to 16; and wherein R is selected from the group consisting of hydrogen, alkyl, alcohol, aromatic amino, amido, nitro, ethers, esters, aldehydes, sulfonyl, silicon moieties, halogens, sulfur containing moieties, phosphorous containing moieties; and ii. a passivation agent monolayer; and b) a second nucleic acid covalently attached to an electron transfer moiety; and c) an AC/DC voltage source electrically connected to said test chamber.

5. An apparatus according to claim 1, 3 or 4, further comprising:

a processor coupled to said electrodes.

6. An apparatus according to claim 1, 3 or 4, wherein said AC/DC voltage source is capable of delivering frequencies from between about 1 Hz to about 100 kHz.

7. An apparatus according to claim 1, 3 or 4 wherein said passivation agent monolayer comprises conductive oligomers.

8. An apparatus according to claim 1, 3 or 4 wherein said passivation agent monolayer comprises insulators.

9. An apparatus according to claims 1, 3 or 4 wherein said passivation agent monolayer comprises alkyl chains.

10. An apparatus according to claim 9 wherein said alkyl chains have the formula $C_nH_x$, where n is 1 to 30, and x is 2(n).

11. An apparatus according to claims 1, 3 or 4 wherein said passivation agent monolayer comprises terminal groups chosen from the group consisting of $-(CH_2)_n-$, $-(CRH)_n-$, $-(CR2)_n-$, ethylene glycol and ethylene glycol derivatives using other heteroatoms in place of oxygen; wherein n is from 1 to 16, and wherein R is selected from the group consisting of hydrogen, alkyl, alcohol, aromatic amino, amido, nitro, ethers, esters, aldehydes, sulfonyl, silicon moieties, halogens, sulfur containing moieties, phosphorous containing moieties, and ethylene glycol moieties.

12. An apparatus according to claims 1, 3 or 4 wherein said passivation agent monolayer comprises both conductive oligomers and insulators.

13. An apparatus for the detection of target nucleic acids in a test sample, comprising:

a) a test chamber comprising an array of electrodes, each electrode comprising i. a covalently attached single stranded nucleic acid, attached to said electrodes via an insulator, wherein said insulator is an alkyl oligomer wherein each monomer of said alkyl oligomer is independently selected from the group consisting of: $-(CH_2)_n-$, $-(CRH)_n-$, $-(CR2)_n-$, ethylene glycol and ethylene glycol derivatives using other heteroatoms in place of oxygen; wherein n is from 1 to 16; and wherein R is selected from the group consisting of hydrogen, alkyl, alcohol, aromatic amino, amido, nitro, ethers, esters, aldehydes, sulfonyl, silicon moieties, halogens, sulfur containing moieties, phosphorous containing moieties; and ii. a passivation agent monolayer; and b) an AC/DC voltage source electrically connected to said test chamber.

14. An apparatus according to claim 13 wherein said passivation agent monolayer comprises conductive oligomers.

15. An apparatus according to claim 13 wherein said passivation agent monolayer comprises insulators.

* * * * *

UNITED STATES PATENT AND TRADEMARK OFFICE
CERTIFICATE OF CORRECTION

| | | |
|---|---|---|
| PATENT NO. | : 7,381,525 B1 | Page 1 of 1 |
| APPLICATION NO. | : 08/873597 | |
| DATED | : June 3, 2008 | |
| INVENTOR(S) | : Jon Faiz Kayyem and Stephen D. O'Connor | |

It is certified that error appears in the above-identified patent and that said Letters Patent is hereby corrected as shown below:

In Col. 64, claim 3, line 34, after "-(CRH)$_n$-," insert -- (CR2)$_n$-, --.

In Col. 65, claim 3, line 3, after "alkyl" insert -- , --.

Signed and Sealed this

Sixteenth Day of March, 2010

David J. Kappos
*Director of the United States Patent and Trademark Office*